United States Patent
Akahata et al.

(10) Patent No.: US 9,637,532 B2
(45) Date of Patent: May 2, 2017

(54) VIRUS LIKE PARTICLE COMPRISING PD-1 ANTIGEN OR PD-1 LIGAND ANTIGEN

(71) Applicant: VLP THERAPEUTICS, LLC, Wilmington, DE (US)

(72) Inventors: Wataru Akahata, Kensington, MD (US); Ryuji Ueno, St Michaels, MD (US)

(73) Assignee: VLP Therapeutics, LLC, Wilmington, DE (US)

( * ) Notice: Subject to any disclaimer, the term of this patent is extended or adjusted under 35 U.S.C. 154(b) by 0 days.

(21) Appl. No.: 14/328,268

(22) Filed: Jul. 10, 2014

(65) Prior Publication Data
US 2015/0017194 A1    Jan. 15, 2015

Related U.S. Application Data

(60) Provisional application No. 61/845,712, filed on Jul. 12, 2013.

(51) Int. Cl.
| | |
|---|---|
| A61K 39/12 | (2006.01) |
| C07K 14/005 | (2006.01) |
| C07K 14/705 | (2006.01) |
| C12N 7/00 | (2006.01) |
| A61K 39/00 | (2006.01) |

(52) U.S. Cl.
CPC ........ *C07K 14/70503* (2013.01); *A61K 39/12* (2013.01); *C07K 14/005* (2013.01); *C07K 14/705* (2013.01); *C07K 14/70596* (2013.01); *C12N 7/00* (2013.01); *A61K 39/00* (2013.01); *A61K 2039/5256* (2013.01); *A61K 2039/5258* (2013.01); *C07K 2319/40* (2013.01); *C07K 2319/735* (2013.01); *C12N 2770/36122* (2013.01); *C12N 2770/36123* (2013.01); *C12N 2770/36134* (2013.01)

(58) Field of Classification Search
CPC .... A61K 2039/5256; A61K 2039/5258; A61K 39/12; A61K 39/39; A61K 2039/5154; A61K 2039/55516; A61K 2039/58; A61K 39/00; C12N 2770/26023; C12N 2760/16134; C12N 2770/36123; C12N 2770/36134; G01N 2333/02; G01N 33/576; Y10S 435/81; Y10S 436/82
See application file for complete search history.

(56) References Cited

U.S. PATENT DOCUMENTS

| | | | |
|---|---|---|---|
| 5,439,809 A | 8/1995 | Haynes et al. | |
| 5,580,773 A | 12/1996 | Kang et al. | |
| 5,629,204 A | 5/1997 | Honjo et al. | |
| 5,698,520 A | 12/1997 | Honjo et al. | |
| 7,101,550 B2* | 9/2006 | Wood ............... | C07K 14/70503 424/130.1 |
| 7,595,048 B2 | 9/2009 | Honjo et al. | |
| 2005/0214321 A1 | 9/2005 | Rasochova et al. | |
| 2007/0122378 A1 | 5/2007 | Freeman et al. | |
| 2009/0298955 A1 | 12/2009 | Handa et al. | |
| 2009/0305950 A1 | 12/2009 | Minato et al. | |
| 2011/0081341 A1 | 4/2011 | Honjo et al. | |
| 2011/0207223 A1 | 8/2011 | Tang et al. | |
| 2012/0003266 A1 | 1/2012 | Nable et al. | |
| 2013/0251744 A1 | 9/2013 | Ueno et al. | |
| 2014/0127247 A1* | 5/2014 | Dubensky, Jr. ...... | C07K 14/005 424/186.1 |
| 2014/0363458 A1 | 12/2014 | Ueno et al. | |
| 2016/0040134 A1 | 2/2016 | Akahata et al. | |
| 2016/0200775 A1 | 7/2016 | Akahata et al. | |

FOREIGN PATENT DOCUMENTS

| | | |
|---|---|---|
| CN | 102321639 A | 1/2012 |
| JP | 04-506301 A | 11/1992 |
| JP | 2007-512842 A | 5/2007 |
| JP | 2008-543774 A | 12/2008 |
| WO | 9310152 A1 | 5/1993 |
| WO | 97/12048 A1 | 4/1997 |
| WO | 2004043399 A2 | 5/2004 |
| WO | 2006040334 A1 | 4/2006 |
| WO | 2006/088229 A1 | 8/2006 |
| WO | 2007003384 A1 | 1/2007 |
| WO | 2007/100098 A1 | 9/2007 |
| WO | 2008025067 A1 | 3/2008 |
| WO | 2009/079185 A2 | 6/2009 |
| WO | 2010/062396 A2 | 6/2010 |
| WO | 2011035004 A1 | 3/2011 |
| WO | 2012/006180 A1 | 1/2012 |
| WO | 2012023995 A1 | 2/2012 |
| WO | 2012/106356 A2 | 8/2012 |
| WO | 2012/123755 A1 | 9/2012 |
| WO | 2013/122262 A1 | 8/2013 |

OTHER PUBLICATIONS

A. Roldão et al., "Virus-like particles in vaccine development", Expert Rev. Vaccines, 2010, vol. 9, No. 10, pp. 1149-1176.
Y. Agata et al., "Expression of the PD-1 antigen on the surface of stimulated mouse T and B lymphocytes", International Immunology, 1996, vol. 8, No. 5, pp. 765-772.
W. Akahata et al., "A VLP vaccine for epidemic Chikungunya virus protects non-human primates against infection", Nat Med., Mar. 2010, vol. 16, No. 3, 12 total pages.
U.S. Appl. No. 14/820,785, filed Aug. 7, 2015 (Inventors: Wataru Akahata and Ryuji Ueno).
F. Notka et al., "Accelerated clearance of SHIV in rhesus monkeys by virus-like particle vaccines is dependent on induction of neutralizing antibodies", Vaccine, 2000, vol. 18, No. 3-4, p. 291-301.
U. Arora et al., "Virus-like particles displaying envelope domain III of dengue virus type 2 induce virus-specific antibody response in mice", Vaccine, Jan. 2013, vol. 31, No. 6, p. 873-878.

(Continued)

*Primary Examiner* — Bao Li
(74) *Attorney, Agent, or Firm* — Sughrue Mion, PLLC

(57) ABSTRACT

The present invention provides a virus like particle comprising a virus structural protein and an antigen derived from PD-1 or a ligand of PD-1, and a composition or kit comprising thereof, its use in immune response etc.

22 Claims, 1 Drawing Sheet

(56) References Cited

OTHER PUBLICATIONS

International Search Report and Written Opinion of the ISA dated Oct. 21, 2014, issued by the International Searching Authority in counterpart International application No. PCT/JP2014/069122.

Ira Mellman et al., "Cancer immunotherapy comes of age", Nature, 2011, 480: 480-489.

Search Report issued in corresponding International Application No. PCT/JP2013/054422 on May 28, 2013.

Gunther Spohn et al., "A Virus-Like Particle-Based Vaccine Selectively Targeting Soluble TNF-alpha Protects from Arthritis without Inducing Reactivation of Latent Tuberculosis", The Journal of Immunology, 2007, 178: 7450-7457.

Elizabeth V.L. Grgacic et al., "Virus-like particles: Passport to immune recognition", Methods, 2006, 40: 60-65.

Gary T. Jennings et al., "Immunodrugs: Therapeutic VLP-Based Vaccines for Chronic Diseases", Annu. Rev. Pharmacol. Toxicol., 2009, 49: 303-326.

Heinz Leibl et al., "Adjuvant/carrier activity of inactivated tick-borne encephalitis virus", Vaccine, 1998, 16(4): 340-345.

Bryce Chackerian et al., "Determinants of Autoantibody Induction by Conjugated Papillomavirus Virus-Like Particles", The Journal of Immunology, 2002, 169: 6120-6126.

Maria Lia Palomba et al., "CD8+ T-Cell-Dependent Immunity Following Xenogeneic DNA Immunization against CD20 in a Tumor Challenge Model of B-Cell Lymphoma", Clinical Cancer Research, 2005, 370(11): 370-379.

Wendy K. Roberts et al., "Vaccination with CD20 peptides induces a biologically active, specific immune response in mice", Blood, 2002, 99: 3748-3755.

Kathy D. McCoy et al., "Cytotoxic T Lymphocyte-associated Antigen 4 (CTLA-4) Can Regulate Dendritic Cell-induced Activation and Cytotoxicity of CD8+ T Cells Independently of CD4+ T Cell Help", J. Exp. Med., 1999, 189(7): 1157-1162.

Gregory J. Atkins et al., "Therapeutic and prophylactic applications of alphavirus vectors", Expert Reviews in Molecular Medicine, 2008, 10(e33): 1-17.

Akahata, W., and G. J. Nabel, 2012, A specific domain of the Chikungunya virus E2 protein regulates particle formation in human cells: implications for alphavirus vaccine design, J. Virol. 86(16):8879-8883.

Kuo, S.-C., et al., 2012, Cell-based analysis of Chikungunya virus El protein in membrane fusion, J. Biomed. Sci. 19(44):1-12.

Communication, dated Sep. 16, 2015, issued by the European Patent Office in counterpart European Patent Application No. 13749307.8.

Communication, dated Oct. 2, 2015, issued by the European Patent Office in counterpart European Patent Application No. 13749307.8.

Siyang Sun et al: "Structural analyses at pseudo atomic resolution of Chikungunya virus and antibodies show mechanisms of neutralization", eLIFE, Apr. 2, 2013, vol. 2, pp. 1-27.

Carvalho et al., "Malaria Vaccine: Candidate Antigens, Mechanisms, Constraints and Prospects", Scand. J. Immunol., Blackwell Science Ltd., Jul. 1, 2002, vol. 56, pp. 327-343.

Crompton et al, "Advances and challenges in malaria vaccine development", Science in medicine, The Journal of Clinical Investigation, Dec. 2010, vol. 120, No. 12, pp. 4168-4178.

Malaria Vaccine Program, http://www.globalvaccines.org/content/malaria+vaccine+program/19614, 4 pages total (2012).

Rodriguez D et al., Vaccine Efficacy against malaria by the Combination of Porcine Parvovirus-Like Particles and Vaccinia Virus Vectors Expressing CS of Plasmodium, PLoS One, Apr. 17, 2012, vol. 7, No. 4, e34445.

Oliveira GA et al., Safety and enhanced immunogenicity of a Hepatitis B core particle Plasmodium falciparum Malaria vaccine formulated in adjuvant montanide ISA 720 in a Phase I Trial, Infect. Immun., 2005, vol. 73, No. 6, pp. 3587-3597.

Jones RM et al., A plant-produced Pfs25 VLP Malaria Vaccine Candidate Induces Persistent Transmission Blocking Antibodies against Plasmodium falciparum in immunized mice, PLoS One, Nov. 18, 2013, vol. 8, No. 11, e79538, doi:10.1371/journal.pone. 0079538.

Rodrigues M et al., Influenza and Vaccinia viruses expressing Malaria CD8+T and B Cell epitopes. Comparison of their immunogenicity and capacity to induce protective immunity, J. Immunol., 1994, vol. 153, No. 10, pp. 4636-4648.

Pfeiffer B et al., A virosome-mimotope approach to synthetic vaccine design and optimization: synthesis, conformation, and immune recognition of a potential Malaria-vaccine candidate, Angew. Chem. Int. Ed., 2003, vol. 42, No. 21, pp. 2368-2371.

Ghasparian A et al., Engineered synthetic virus-like particles and their use in vaccine delivery, Chembiochem, 2011, vol. 12, No. 1, pp. 100-109.

Dobano C et al., Alphavirus replicon particles are highly immunogenic in the murine Malaria model by homologous or heterologous immunization, Open Vaccine Journal, vol. 1, 2008, pp. 27-37.

Lechner F et al., Virus-like particles as a modular system for novel vaccines, Intervirology, 2002, vol. 45, No. 4-6, pp. 212-217.

Gilbert SC et al., A protein particle vaccine containing multiple Malaria epitopes, Nat. Biotechnol., 1997, vol. 15, No. 12, pp. 1280-1284.

Allsopp CE et al., Comparison of numerous delivery systems for the induction of cytotoxic T lymphocytes by immunization, Eur. J. Immunol., 1996, vol. 26, No. 8, pp. 1951-1959.

International Search Report and Written Opinion dated Sep. 16, 2014, issued by the International Searching Authority in counterpart International Application No. PCT/JP2014/065166.

Oliveira-Ferreira et al. Immunogenicity of Ty-VLP bearing a CD8(+) T cell epitope of the CS protein of P. yoelii: enhanced memory response by boosting with recombinant vaccinia virus. Vaccine. Mar. 6, 2000;18(17):1863-9.

GenBank: AAW78190.1. circumsporozoite protein, partial [Plasmodium falciparum]. Dec. 29, 2006. http://www.ncbi.nlm.nih.gov/protein/58429573?report=genbank&log$=protalign&blast_rank=18&RID=P92 DMO5R01 R.

Gregson et al. Phase I Trial of an Alhydrogel Adjuvanted Hepatitis B Core Virus-Like Particle Containing Epitopes of Plasmodium falciparum Circumsporozoite Protein. PLoS One. Feb. 2008 | vol. 3 | Issue 2 | e1556.

Adams et al. The expression of hybrid HIV:Ty virus-like particles in yeast. Nature. Sep. 3-9, 1987;329(6134):68-70.

GenBank: ADG95942.1 structural polyprotein [Chikungunya virus] http://www.ncbi.nlm.nih.gov/protein/296124572?report=genbank &log$=protalign&blast_rank=2&RID=PBR 7NT0U015. Dec. 28, 2010.

Calvo-Calle et al. A Linear Peptide Containing Minimal T- and B-Cell Epitopes of Plasmodium falciparum Circumsporozoite Protein Elicits Protection against Transgenic Sporozoite Challenge. Infection and Immunity, Dec. 2006, p. 6929-6939. vol. 74, No. 12.

Federico M. Virus-like particles show promise as candidates for new vaccine strategies. Future Virol. (2010) 5(4), 371-374.

Communication, dated Jul. 5, 2016, issued by the European Patent Office in counterpart European Application No. 14807026.1.

Birkett A et al. "A Modified Hepatitis B Virus Core Particle Containing Multiple Epitopes of the Plasmodium falciparum Circumsporozoite Protein Provides a Highly Immunogenic Malaria Vaccine in Preclinical Analyses in Rodent and Primate Hosts", Infection and Immunity, American Society for Microbiology, US, vol. 70, No. 12; Dec. 1, 2002, pp. 6860-6870.

Milich D R et al. "Conversion of poorly immunogenic malaria repeat sequences into a highly immunogenic vaccine candidate", Vaccine, Elsevier Ltd, GB; vol. 20, No. 5-6; Dec. 12, 2001; pp. 771-788.

Shiratsuchi T. et al. "Replacing adenoviral vector HVR1 with a malaria B cell epitope improves immunogenicity and circumvents preexisting immunity to adenovirus in mice", Journal of Clinical Investigation; vol. 120, No. 10; Oct. 2010; pp. 3688-3701.

Office Action dated Nov. 19, 2014 in U.S. Appl. No. 13/768,801.

Office Action dated Apr. 1, 2015 in U.S. Appl. No. 13/768,801.

Notice of Allowance dated Nov. 6, 2015 in U.S. Appl. No. 13/768,801.

Office Action dated Jun. 9, 2015 in U.S. Appl. No. 14/294,968.

(56) References Cited

OTHER PUBLICATIONS

Office Action dated Dec. 3, 2015 in U.S. Appl. No. 14/294,968.
Advisory Action dated Mar. 29, 2016 in U.S. Appl. No. 14/294,968.
Notice of Allowance dated Jul. 26, 2016 in U.S. Appl. No. 14/294,968.
Communication dated Jan. 2, 2017, from the European Patent Office in corresponding European Application No. 14823398.4.

* cited by examiner

VIRUS LIKE PARTICLE COMPRISING PD-1 ANTIGEN OR PD-1 LIGAND ANTIGEN

CROSS REFERENCE TO RELATED APPLICATIONS

This application claims the benefit of U.S. Provisional Patent Application No. 61/845,712 filed on Jul. 12, 2013, the entire contents of which are incorporated by reference herein.

TECHNICAL FIELD

The present invention relates to a virus like particle comprising a virus structural protein and an antigen derived from PD-1 or a ligand of PD-1, and a composition or a kit comprising thereof, its use in immune response etc.

BACKGROUND ART

Programmed Cell Death 1 or PD-1 (also referred to as PDCD1) is a 50 to 55 kDa type I transmembrane receptor of the CD28 superfamily that negatively regulates T cell antigen receptor signaling by interacting with the specific ligands and is suggested to play a role in the maintenance of self-tolerance.

PD-1 antigen relates to almost every aspect of immune responses including autoimmunity, tumor immunity, infectious immunity, transplantation immunity, allergy and immunological privilege.

PD-1 is expressed on the surface of activated T cells, B cells, and macrophages, (Y. Agata et al., International Immunology vol. 8, No. 5 p 765-772, 1996) suggesting that compared to CTLA-4 that also plays an important regulatory role in the immune system, PD-1 more broadly negatively regulates immune responses.

In general, a need exists to provide safe and effective therapeutic methods for immune disorders such as, for example, autoimmune diseases, inflammatory disorders, allergies, transplant rejection, cancer, immune deficiency, and other immune system-related disorders. Modulation of the immune responses involved in these disorders can be accomplished by manipulation of the PD-1 pathway.

PD-1 has two ligands, PD-L1 (Programmed Death Ligand for PDCD1 L1 or B7-H1) and PD-L2 (Programmed Death Ligand 2 or PDCD1 L2 or B7-DC), which are members of the B7 family ligands.

In one approach, blocking the interaction of PD-1 as well as its ligand (PD-L1, PD-L2 or both) may provide an effective way for tumor and viral immunotherapy.

U.S. Pat. No. 5,629,204 and U.S. Pat. No. 5,698,520 relate to a membrane protein related to human PD-1 and DNA encoding the said protein, and indicates that PD-1 protein may be useful for the treatment of various infections, immunological depression or acceleration, or tumors etc.

U.S. Pat. No. 7,595,048 and US 2011/0081341 relate to immunopotentiation characterized by inhibiting immunosuppressive signals induced by PD-1, PD-L1 or PD-L2, compositions for cancer or infection treatment, and therapies that use them.

Several big pharmaceutical companies are pitting their PD-1 antibodies against each other in a race to be first to market. Here are 3 monoclonal antibodies such as Merck's Lambrolizumab (MK-3475) which is a humanized monoclonal IgG4 antibody that acts against PD-1, Bristol-Myers Squibb's Nivolumab (BMS-936558) which is fully anti human PD-1 antibody and Roche Genentech's MPDL3280A which doesn't block PD-1, but rather blocks PD-L1.

However, more potent and safe compound targeting PD-1 is strongly desired.

Virus-like particles (VLPs) are multiprotein structures that mimic the organization and conformation of authentic native viruses but lack the viral genome, potentially yielding safer and cheaper vaccine candidates. A handful of prophylactic VLP-based vaccines is currently commercialized worldwide: GlaxoSmithKline's Engerix® (hepatitis B virus) and Cervarix® (human papillomavirus), and Merck and Co., Inc.'s Recombivax HB® (hepatitis B virus) and Gardasil® (human papillomavirus) are some examples. Other VLP-based vaccine candidates are in clinical trials or undergoing preclinical evaluation, such as, influenza virus, parvovirus, Norwalk and various chimeric VLPs. Many others are still restricted to small-scale fundamental research, despite their success in preclinical tests. The implications of large-scale VLP production are discussed in the context of process control, monitorization and optimization. The main up- and down-stream technical challenges are identified and discussed accordingly. Successful VLP-based vaccine blockbusters are briefly presented concomitantly with the latest results from clinical trials and the recent developments in chimeric VLP-based technology for either therapeutic or prophylactic vaccination (Expert Rev. Vaccines 9(10), 1149-1176, 2010).

Chikungunya virus (CHIKV) has infected millions of people in Africa, Europe and Asia since this alphavirus reemerged from Kenya in 2004. The severity of the disease and the spread of this epidemic virus present a serious public health threat in the absence of vaccines or antiviral therapies. It is reported that a VLP vaccine for epidemic Chikungunya virus protects non-human primates against infection (Nat Med. 2010 March; 16(3): 334-338). US patent publication No. 2012/0003266 discloses a virus-like particle (VLP) comprising one or more Chikungunya virus structural proteins which is useful for formulating a vaccine or antigenic composition for Chikungunya that induces immunity to an infection or at least one symptom thereof. WO2012/106356 discloses modified alphavirus or flavivirus virus-like particles (VLPs) and methods for enhancing production of modified VLPs for use in the prevention or treatment of alphavirus and flavivirus-mediated diseases. (these cited references are herein incorporated by reference).

SUMMARY OF INVENTION

In a first aspect, the present invention provides a particle comprising a virus structural protein and an antigen selected from the group consisting of an antigen derived from PD-1 and an antigen derived from a ligand of PD-1.

In a second aspect, the present invention provides a nucleic acid molecule comprising a nucleotide sequence for expressing a particle which comprises a virus structural protein and an antigen selected from the group consisting of an antigen derived from PD-1 and an antigen derived from a ligand of PD-1.

In a third aspect, the present invention provides a pharmaceutical composition and a kit comprising a pharmaceutical composition, wherein the pharmaceutical composition comprises a particle comprising a virus structural protein and an antigen selected from the group consisting of an antigen derived from PD-1 and an antigen derived from a ligand of PD-1; or a nucleic acid molecule comprising a nucleotide sequence for expressing a particle which comprises a virus structural protein and an antigen selected from the group consisting of an antigen derived from PD-1 and an antigen derived from a ligand of PD-1; and a pharmaceutically acceptable carrier.

In a forth aspect, the present invention provides a use of a particle comprising a virus structural protein and an antigen selected from the group consisting of an antigen derived from PD-1 and an antigen derived from a ligand of PD-1; or a nucleic acid molecule comprising a nucleotide sequence for expressing a particle which comprises a virus structural protein and an antigen selected from the group consisting of an antigen derived from PD-1 and an antigen derived from a ligand of PD-1 for the manufacture of a pharmaceutical composition or a kit for modulating an immuno response, treating cancer or treating an infectious disease in a subject.

Figure 1:
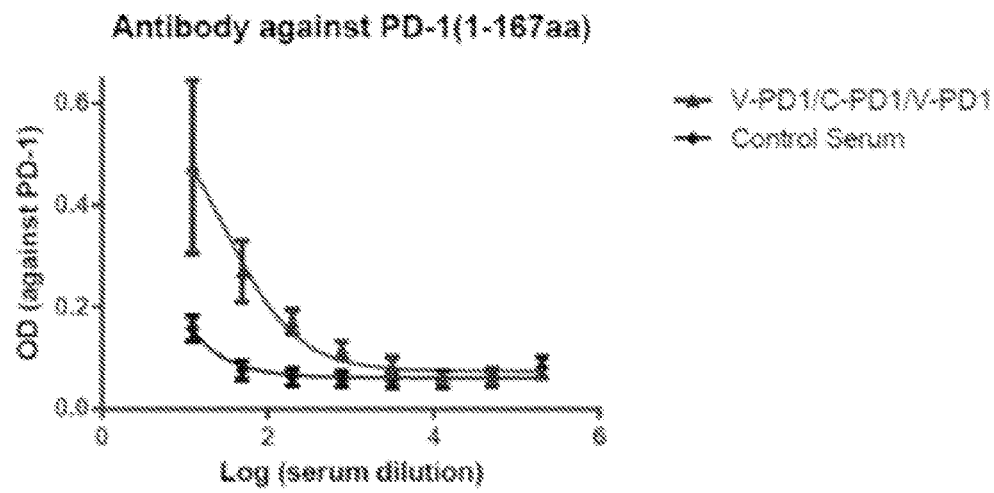
FIG. 1 shows results of ELISA where an antibody which binds to N-terminal PD-1 (1-167aa) was detected.

DESCRIPTION OF EMBODIMENT (1) Particle Comprising a Virus Structural Protein and an Antigen Selected from the Group Consisting of an Antigen Derived from PD-1 and an Antigen Derived from a Ligand of PD-1

In a first aspect, the present invention provides a particle comprising a virus structural protein and an antigen selected from the group consisting of an antigen derived from PD-1 and an antigen derived from a ligand of PD-1.

A derivative of the above-described particle which can be prepared by modulating the above-described particle is also provided by the present invention. Examples of the modification include, but are not limited to, addition, deletion or replacement of one or more amino acid residues.

The particle provided by the present invention may be a particle which consists of or comprises i) at least one virus structural protein and ii) at least one antigen derived from PD-1 or at least one antigen derived from a ligand of PD-1. The at least one virus structural protein may consist of one or more kinds of protein or peptide and spontaneously assembled to form the particle provided by the present invention. In one embodiment, the particle provided by the present invention has a diameter of at least 10 nm, for example, at least 20 nm, preferably at least 50 nm. In one embodiment, molecular weight of the particle is from 100 kDa to 100,000 kDa, preferably from 400 kDa to 30,000 kDa.

Preferably, a virus structural protein used for the present invention may be a virus structural protein derived from Alphavirus or Flavivirus. Thus, the particle provided by the present invention may be a virus like particle including a virus like particle derived from Alphavirus or Flavivirus. Examples of Alphavirus and Flavivirus include, but not limited to, Aura virus, Babanki virus, Barmah Forest virus (BFV), Bebaru virus, Cabassou virus, Chikungunya virus (CHIKV), Eastern equine encephalitis virus (EEEV), Eilat virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus (RRV), Salmon pancreas disease virus, Semliki Forest virus, Sindbis virus, Southern elephant seal virus, Tonate virus, Trocara virus, Una virus, Venezuelan equine encephalitis virus (VEEV), Western equine encephalitis virus (WEEV), Whataroa virus, West Nile virus, dengue virus, tick-borne encephalitis virus and yellow fever virus.

Virus structural protein may be a capsid protein, an envelope protein, a fragment thereof or a complex thereof. Thus, virus structural protein used for the present invention may consist of or comprise a capsid protein and/or an envelope protein and/or a fragment thereof. In one embodiment, the virus like particle provided by the present invention consists of or comprises capsid, E2 and E1. An antigen may be inserted into E2. For example, the virus like particle provided by the present invention may be formed by assembling 240 capsids, 240 E1 proteins and 240 E2 proteins where a PD-1 antigen is inserted into each of E2 proteins.

As used herein, the term "PD-1 antigen" refers to an antigen derived from PD-1. Preferably, PD-1 is a human PD-1. An antigen derived from PD-1 may be a fragment of PD-1 or a derivative of a fragment of PD-1.

As used herein, the term "PD-1 ligand antigen" refers to an antigen derived from a ligand of PD-1. Examples of a ligand of PD-1 include, but are not limited to, PD-L1 and PD-L2. Preferably, a ligand of PD-1 is human PD-L1 or human PD-L2. An antigen derived from PD-L1 may be a fragment of PD-L1 or PD-L2; or a derivative of a fragment of PD-L1 or PD-L2.

A fragment of PD-1, PD-L1 or PD-L2 for use in an antigen contained in the particle provided by the present invention may be selected based on the amino acid sequence of PD-1, PD-L1 or PD-L2 and/or tertiary structure thereof.

For example, a fragment for use in the antigen may consist of or comprise a fragment located in the surface of PD-1, PD-L1 or PD-L2. Preferably, an antibody against an antigen contained in the particle provided by the present invention blocks an interaction between PD-1 and PD-L1 or PD-1 and PD-L2. A fragment of PD-1, PD-L1 or PD-L2 for use in the antigen may be 10-300 amino acid residues (e.g. 10-120, 10-30 or 15-30 amino acid residues) in length.

In one embodiment, a fragment for use in the antigen may be selected so that spatial distance between the N-terminal residue and C-terminal residue of the antigen is 30 Å or less when the distance is determined in a crystal of the antigen or a naturally occurring protein containing the antigen or modified protein therefrom. For example, an antigen used for the particle provided by the present invention can be designed using a free software including PyMOL (e.g. PyMOL v0.99: http:/www.pymol.org). In one embodiment, a spatial distance between N-terminal residue and C-terminal residue of the antigen is 30 Å (angstrom) or less, 20 Å or less, or 10 Å or less (e.g. from 5 Å to 15 Å, from 5 Å to 12 Å, from 5 Å to 11 Å, from 5 Å to 10 Å, from 5 Å to 8 Å, from 8 Å to 15 Å, from 8 Å to 13 Å, from 8 Å to 12 Å, from 8 Å to 11 Å, from 9 Å to 12 Å, from 9 Å to 11 Å, from 9 Å to 10 Å or from 10 Å to 11 Å).

Examples of a fragment of PD-1 for use in the antigen include, but are not limited to, lnwyrmspsnqtdklaaf (SEQ ID No.:4), mlnwyrmspsnqtdklaafs (SEQ ID No.:5), vlnwyrmspsnqtdklaafp (SEQ ID No.:6), gaislhpkakiees (SEQ ID No.:7), cgaislhpkakieec (SEQ ID No.:8), VLNWYRMSPSNQTDKLAAF (SEQ ID No.:9), GAISLAPKAQIKES (SEQ ID No.:10), RNDSGTYLCGAISLAPKAQIKESL-RAELRVT (SEQ ID No.:11) and RNDSGIYLCGAISLHP-KAKIEESPGAELVVT (SEQ ID No.:12). Examples of a fragment of PD-L1 for use in the antigen include, but are not limited to, ciisyggadyc (SEQ ID No.:13), CMISYGGADYC (SEQ ID No.:14), LQDAGVYRCMISYGGADYKRITVKVN (SEQ ID No.:15), LQDAGVYRAMISYGGADYKRITVKVN (SEQ ID No.:16), DLAALIVYWEMEDKNIIQFVH (SEQ ID No.:17), DLAALIVYWEMEDKNIIQFVHGG (SEQ ID No.:18), FTVTVPKDLYVVEYGSNMTIECKFPVE (SEQ ID No.: 19), Lqdagvycciisyggadykritlkvn (SEQ ID No.: 20), Iqdagvyaaiisyggadykritlkvn (SEQ ID No.:21), dllalvvywekedeqviqfva (SEQ ID No.: 22), dllalvvywekedeqviqfvagg (SEQ ID No.: 23) and ftitapkdlyvveygsnvtmecrfpve (SEQ ID No.: 24).

A derivative of a fragment of PD-1, PD-L1 or PD-L2 may be prepared by addition, deletion or replacement of one or several amino acid residues in the fragment of PD-1, PD-L1 or PD-L2. In one embodiment, a derivative of a fragment of PD-1, PD-L1 or PD-L2 has at least 70%, 75%, 80%, 85%, 90%, 95% or 98% amino acid sequence identity to the corresponding fragment of a naturally occurring PD-1, PD-L1 or PD-L2. In one embodiment, a derivative of a fragment of PD-1, PD-L1 or PD-L2 is a mutant where at most 10% of the amino acids are deleted, substituted, and/or added based on the corresponding fragment of naturally occurring PD-1, PD-L1 or PD-L2.

In the particle as provided by the present invention, a virus structural protein and an antigen may be linked through at least one first attachment site which is present in the virus structural protein and at least one second attachment site which is present in the antigen.

As used herein, each of "a first attachment site" and "a second attachment site" refers to a site where more than one substance is linked each other.

In one embodiment, a virus structural protein and an antigen are directly fused. In one embodiment, one or two linkers may intervene between N-terminal residue of an antigen and a virus structural protein and/or between C-terminal residue of an antigen and a virus structural protein.

An antigen or a virus structural protein can be truncated and replaced by short linkers. In some embodiments, an antigen or a virus structural protein include one or more peptide linkers. Typically, a linker consists of from 2 to 25 amino acids. Usually, it is from 2 to 15 amino acids in length, although in certain circumstances, it can be only one, such as a single glycine residue.

In one embodiment, a nucleic acid molecule, in which polynucleotide encoding the virus structural protein is genetically fused with polynucleotide encoding the antigen, is expressed in a host cell so that the first attachment site and the second attachment site are linked through a peptide bond. In this case, the virus structural protein and the antigen are linked through a peptide bond. Relating to this embodiment, the first attachment site and/or the second attachment site may be genetically modified from the original protein or antigen. For example, the first attachment site is modified from the virus structural protein so that through a linker peptide including SG, GS, SGG, GGS and SGSG, the protein is conjugated with the antigen.

When the virus structural protein are chemically conjugated with the antigen, the first attachment site and the second attachment site may be linked through a chemical cross-linker which is a chemical compound.

Examples of the cross-linker include, but are not limited to, SMPH, Sulfo-MBS, Sulfo-EMCS, Sulfo-GMBS, Sulfo-SIAB, Sulfo-SMPB, Sulfo-SMCC, SVSB, SIA and other cross-linkers available from the Pierce Chemical Company.

Preferably, an antigen may be linked to the Chikungunya virus structural protein or Venezuelan equine encephalitis virus structural protein as a fusion protein produced by way of genetic engineering.

A Chikungunya virus structural protein or Venezuelan equine encephalitis virus structural protein used in the present invention may be a Chikungunya or Venezuelan equine encephalitis virus envelope protein or a capsid or a complex of one or more envelope proteins and/or a capsid protein.

Examples of Chikungunya virus include, but are not limited to, strains of 37997 and LR2006 OPY-1. Examples of Venezuelan equine encephalitis virus include, but are not limited to, TC-83.

Chikungunya virus structural protein or Venezuelan equine encephalitis virus structural protein used in the present invention may naturally occurring virus structural protein or modified protein thereof. The modified protein may be a fragment of the naturally occurring virus structural protein. In one embodiment, the modified protein has at least 70%, 75%, 80%, 85%, 90%, 95% or 98% amino acid sequence identity to a naturally occurring viral capsid and/or envelope protein. In one embodiment, the modified protein is a mutant where at most 10% of the amino acids are deleted, substituted, and/or added based on a naturally occurring viral capsid and/or envelope protein. For example, K64A or K64N mutatation may be introduced into a capsid of Venezuelan equine encephalitis virus structural protein used in the present invention.

Chikungunya or Venezuelan equine encephalitis virus structural protein may consist of or comprise a capsid, E2 and E1.

Examples of Chikungunya virus structural protein include, but are not limited to, Capsid-E2-E1 of Chikungunya virus Strain 37997, and Capsid-E2-E1 of Chikungunya virus LR2006 OPY-1.

Examples of Venezuelan equine encephalitis virus structural protein include, but are not limited to, Capsid-E2-E1 of Venezuelan equine encephalitis virus Strain TC-83.

An exemplary Chikungunya virus structural protein sequence is provided at Genbank Accession No. ABX40006.1, which is described below (SEQ ID No: 1):

```
mefiptqtfynrryqprpwtprptiqvirprprpqrqagqlaqlisavnk ltmravpqqkprrnrknkkqkqkqqapqnntnqkkqppkkkpaqkkkkpg rrermcmkiendcifevkhegkvtgyaclvgdkvmkpahvkgtidnadla klafkrsskydlecaqipvhmksdaskfthekpegyynwhhgavqysggr ftiptgagkpgdsgrpifdnkgrvvaivlgganegartalsvvtwnkdiv tkitpegaeewslaipvmcllanttfpcsqppctpccyekepeetlrmle dnvmrpgyyqllqasltcsphrqrrstkdnfnvykatrpylahcpdcgeg hschspvalerirneatdgtlkiqvslqigiktddshdwtklrymdnhmp adaeraglfvrtsapctitgtmghfilarcpkgetltvgftdsrkishsc thpfhhdppvigrekfhsrpqhgkelpcstyvqstaatteeievhmppdt pdrtlmsqqsgnvkitvngqtvrykcncggsnegltttdkvinnckvdqc haavtnhkkwqynsplvprnaelgdrkgkihipfplanvtcrvpkarnpt vtygknqvimllypdhptllsyrnmgeepnyqeewvmhkkevvltvpteg levtwgnnepykywpqlstngtahghpheiilyyyelyptmtvvvvsvat
```

-continued

```
fillsmvgmaagmcmcarrrcitpyeltpgatvpfllsliccirtakaat yqeaaiylwneqqplfwlqaliplaalivlcnclrllpcccktlaflavm svgahtvsayehvtvipntvgvpyktlvnrpgyspmvlemellsvtlept lsldyitceyktvipspyvkccgtaeckdknlpdysckvftgvypfmwgg aycfcdaentqlseahveksescktefasayrahtasasaklrvlyqgnn itvtayangdhavtvkdakfivgpmssawtpfdnkivvykgdvynmdypp fgagrpgqfgdiqsrtpeskdvyantqlvlqrpavgtvhvpysqapsgfk ywlkergaslqhtapfgcqiatnpvravncavgnmpisidipeaaftrvv dapsltdmscevpacthssdfggvaiikyaaskkgkcavhsmtnavtire aeievegnsqlqisfstalasaefrvqvcstqvhcaaechppkdhivnyp ashttlgvqdisatamswvqkitggvglvvavaalilivvlcvsfsrh
```

Another exemplary Chikungunya virus structural protein sequence is provided at Genbank Accession No. ABX40011.1, which is described below (SEQ ID No: 2):

```
mefiptqtfynrryqprpwaprptiqvirprprpqrgagqlaqlisavnk ltmravpqqkprrnrknkkgrqkkqapqndpkqkkqppqkkpaqkkkkpg rrermcmkiendcifevkhegkvmgyaclvgdkvmkpahvkgtidnadla klafkrsskydlecaqipvhmksdaskfthekpegyynwhhgavqysggr ftiptgagkpgdsgrpifdnkgrvvaivlgganegartalsvvtwnkdiv tkitpegaeewslalpvlcllanttfpcsqppctpccyekepestlrmle dnvmrpgyyqllkasltcsphrqrrstkdnfnvykatrpylahcpdcgeg hschspialerirneatdgtlkiqvslqigiktddshdwtklrymdshtp adaeragllvrtsapctitgtmghfilarcpkgetltvgftdsrkishtc thpfhheppvigrerfhsrpqhgkelpcstyvqstaataeeievhmppdt pdrtlmtqqsgnvkitvngqtvrykcncggsneglttttdkvinnckidqc haavtnhknwqynsplvprnaelgdrkgkihipfplanvtcrvpkarnpt vtygknqvtmllypdhptllsyrnmgqepnyheewvthkkevtltypteg levtwgnnepykywpqmstngtahghpheiilyyyelyptmtvvivsvas fvllsmvgtavgmcvcarrrcitpyeltpgatvpfllsllccvrttkaat yyeaaaylwneqqplfwlqaliplaalivlcnclkllpcccktlaflavm sigahtvsayehvtvipntvgvpyktivnrpgyspmvlemelqsvtlept lsldyitceyktvipspyvkccgtaeckdkslpdysckvftgvypfmwgg aycfcdaentqlseahveksescktefasayrahtasasaklrvlyqgnn itvaayangdhavtvkdakfvvgpmssawtpfdnkivvykgdvynmdypp fgagrpgqfgdiqsrtpeskdvyantqlvlqrpaagtvhvpysqapsgfk ywlkergaslqhtapfgcqiatnpvravncavgnipisidipdaaftrvv dapsvtdmscevpacthssdfggvaiikytaskkgkcavhsmtnavtire advevegnsqlqisfstalasaefrvqvcstqvhcaaachppkdhivnyp ashttlgvqdisttamswvqkitggvglivavaalilivvlcvsfsrh
```

An exemplary Venezuelan equine encephalitis virus structural protein is described below (SEQ ID No: 3):

```
mfpfqpmypmqpmpyrnpfaaprrpwfprtdpflamqvqeltrsmanitf kqrrdappegpsaakpkkeasqkqkgggqgkkkknqgkkkaktgppnpka qngnkkktnkkpgkrqrmvmklesdktfpimlegkingyacvvggklfrp mhvegkidndvlaalktkkaskydleyadvpqnmradtfkythekpqgyy swhhgavqyengrftvpkgvgakgdsgrpildnqgrvvaivlggvnegsr talsvvmwnekgvtvkytpenceqwslvttmcllanvtfpcaqppicydr kpaetlamlsvnvdnpgydelleaavkcpgrkrrsteelfneykltrpym arcircavgschspiaieavksdghdgyvrlqtssqygldssgnlkgrtm rydmhgtikeiplhqvslytsrpchivdghgyfllarcpagdsitmefkk dsvrhscsvpyevkfnpvgrelythppehgveqacqvyandaqnrgayve mhlpgsevdsslvslsgssvtvtppdgtsalvececggtkisetinktkq fsqctkkeqcrayrlqndkwvynsdklpkaagatlkgklhvpflladgkc tvplapepmitfgfrsyslklhpknptylitrqladephythelisepav rnftvtekgwefvwgnhppkrfwaqetapgnphglphevithyyhrypms tilglsicaaiatvsvaastwlfcrsrvacltpyrltpnaripfclavlc cartaraettwesldhlwnnnqqmfwiqlliplaalivvtrllrcvccvv pflvmagaagagayehattmpsqagisyntivnragyaplpisitptkik liptvnleyvtchyktgmdspaikccgsqectptyrpdeqckvftgvypf mwggaycfcdtentqvskayvmksddcladhaeaykahtasvqaflnitv gehsivttvyvngetpvnfngvkitagplstawtpfdrkivqyageiyny dfpeygagqpgafgdiqsrtvsssdlyantnlvlqrpkagaihvpytqap sgfeqwkkdkapslkftapfgceiytnpiraencavgsiplafdipdalf trvsetptlsaaectlnecvyssdfggiatvkysasksgkcavhvpsgta tlkeaavelteggsatihfstanihpefrlqictsyvtckgdchppkdhi vthpqyhaqtftaavsktawtwltsllggsaviiiiglvlativamyvlt nqkhn
```

In one embodiment, a first attachment site comprises an amino group, preferably an amino group of a lysine residue. In one embodiment, the second attachment site comprises sulfhydryl group, preferably, a sulfhydryl group of a cysteine.

According to the present invention, a Chikungunya virus like particle or Venezuelan equine encephalitis virus like particle comprising a Chikungunya or Venezuelan equine encephalitis virus structural protein and an antigen selected from the group consisting of an antigen derived from PD-1 and an antigen derived from a ligand of PD-1 (e.g. PD-L1, PD-L2), wherein the Chikungunya virus structural protein or Venezuelan equine encephalitis virus structural protein and the antigen are expressed as a fusion protein can be provided.

An antigen selected from the group consisting of an antigen derived from PD-1 and an antigen derived from a ligand of PD-1 (e.g. PD-L1, PD-L2) can be fused with any site of the Chikungunya virus structural protein or Venezuelan equine encephalitis virus structural protein. For example, an antigen selected from the group consisting of an antigen derived from PD-1 and an antigen derived from a ligand of PD-1 (e.g. PD-L1, PD-L2) may be directly or indirectly linked to N- or C-terminal of a Chikungunya virus structural protein or Venezuelan equine encephalitis virus structural protein, or an antigen selected from the group consisting of an antigen derived from PD-1 and an antigen derived from a ligand of PD-1 (e.g. PD-L1, PD-L2) may be inserted into Chikungunya virus structural protein or Venezuelan equine encephalitis virus structural protein.

In one embodiment, at least one antigen selected from the group consisting of an antigen derived from PD-1 and an antigen derived from a ligand of PD-1 (e.g. PD-L1, PD-L2) is inserted into E2 of Chikungunya virus structural protein or Venezuelan equine encephalitis virus structural protein. For example, regarding Chikungunya virus structural protein, at least one antigen selected from the group consisting of an antigen derived from PD-1 and an antigen derived from a ligand of PD-1 (e.g. PD-L1, PD-L2) is inserted between residues 519 and 520 of SEQ ID Nos.:1 or 2 (i.e. between G at 519-position and Q at 520-position of SEQ ID Nos.:1 or 2); between residues 530 and 531 of SEQ ID Nos.:1 or 2 (i.e. between G at 530-position and S at 531-position of SEQ ID Nos.:1 or 2); between residues 531 and 532 of SEQ ID Nos.:1 or 2 (i.e. between S at 531-position and N at 532-position of SEQ ID Nos.:1 or 2); between residues 529 and 530 of SEQ ID Nos.:1 or 2 (i.e. between G at 529-position and G at 530-position of SEQ ID Nos.:1 or 2); or between residues 510 and 511 of SEQ ID Nos.:1 or 2 (i.e. between S at 510-position and G at 511-position of SEQ ID Nos.:1 or 2); or between residues 511 and 512 of SEQ ID Nos.:1 or 2 (i.e. between G at 511-position and N at 512-position of SEQ ID Nos.:1 or 2); or between residues 509 and 510 of SEQ ID Nos.:1 or 2 (i.e. between Q at 509-position and S at 510-position of SEQ ID Nos.:1 or 2). VLP_CHI 532 vector (SEQ ID No.: 25) may be used for preparing Chikungunya virus like particle where the antigen is inserted between residues 531 and 532 of SEQ ID Nos. 1 or 2.

For example, regarding Venezuelan equine encephalitis virus structural protein, at least one antigen selected from the group consisting of an antigen derived from PD-1 and an antigen derived from a ligand of PD-1 (e.g. PD-L1, PD-L2) is inserted between residues 517 and 518 of SEQ ID No.:3 (i.e. between G at 517-position and S at 518-position of SEQ ID No.:3); between residues 518 and 519 of SEQ ID No.:3 (i.e. between S at 518-position and S at 519-position of SEQ ID No.:3); between residues 519 and 520 of SEQ ID No.:3 (i.e. between S at 519-position and V at 520-position of SEQ ID No.:3); between residues 515 and 516 of SEQ ID No.:3 (i.e. between L at 515-position and S at 516-position of SEQ ID No.:3); between residues 516 and 517 of SEQ ID No.:3 (i.e. between S at 516-position and G at 517-position of SEQ ID No.:3); between residues 536 and 537 of SEQ ID No.:3 (i.e. between C at 536-position and G at 537-position of SEQ ID No.:3); between residues 537 and 538 of SEQ ID No.:3 (i.e. between G at 537-position and G at 538-position of SEQ ID No.:3); between residues 538 and 539 of SEQ ID No.:3 (i.e. between G at 538-position and T at 539-position of SEQ ID No.:3). VLP_VEEV VLP 518 vector (SEQ ID No.:26) may be used for preparing Venezuelan equine encephalitis virus like particle where the antigen is inserted between residues 517 and 518 of SEQ ID No. 3.

The fusion protein may be expressed using a conventional technique in the art. A variety of expression systems can be used for the expression of the fusion protein. For example, the fusion protein can be expressed in 293 cells, Sf9 cells or *E. coli*.

A protein derived from Chikungunya virus (CHIKV) or Venezuelan equine encephalitis virus (VEEV) may be a naturally occurring viral protein or modified protein thereof.

When a protein derived from a virus is conjugated with a protein derived from an antigen, a linker peptide including SG, GS, SGG, GGS SGSG and TRGGS may be used. Examples of conjugation of the protein derived from a virus (referred to as "PFV" below) with the protein derived from the antigen (referred to as "PFA" below) include, but not limited to: PFV-SG-PFA-GS-PFV; PFV-SG-PFA-GGS-PFV; PFV-SSG-PFA-GS-PFV; PFV-SGG-PFA-GGS-PFV; PFV-SGSG-PFA-GS-PFV; and PFA-SGG-PFA-TRGGS-PFV.

In one embodiment, the present invention provides a virus like particle comprising a fusion protein of a protein derived from Chikungunya virus (CHIKV) or Venezuelan equine encephalitis virus (VEEV) and a protein derived from PD-1 or PD-L1, wherein the virus like particle is prepared by transfecting an expression vector comprising a nucleic acid molecule comprising a nucleotide sequence represented by SEQ ID Nos.:27-32 into a mammalian cell (e.g. 293F cell). Regarding this embodiment, modified fusion protein can be also used for a virus like particle provided by the present invention, which can be prepared by transfecting an expression vector comprising a nucleic acid molecule comprising a nucleotide sequence having at least 70%, 75%, 80%, 85%, 90%, 95% or 98% amino acid sequence identity to SEQ ID Nos.: 27-32 into a mammalian cell (e.g. 293F cell).

In one embodiment, the present invention provides a virus like particle comprising or consisting of:
one or more capsid of Chikungunya virus (CHIKV) or Venezuelan equine encephalitis virus (VEEV);
one or more E1 of Chikungunya virus (CHIKV) or Venezuelan equine encephalitis virus (VEEV); and
one or more E2 of Chikungunya virus (CHIKV) or Venezuelan equine encephalitis virus (VEEV), wherein an antigen selected from the group consisting of an antigen derived from PD-1 and an antigen derived from a ligand of PD-1 (e.g. PD-L1, PD-L2) is inserted into E2 of Chikungunya virus (CHIKV) or Venezuelan equine encephalitis virus (VEEV). For example, present invention provides a virus like particle comprising or consisting of:
240 capsids of Chikungunya virus (CHIKV) or Venezuelan equine encephalitis virus (VEEV);
240 E1s of Chikungunya virus (CHIKV) or Venezuelan equine encephalitis virus (VEEV); and
240 E2s of Chikungunya virus (CHIKV) or Venezuelan equine encephalitis virus (VEEV), wherein an antigen selected from the group consisting of an antigen derived from PD-1 and an antigen derived from a ligand of PD-1 (e.g. PD-L1, PD-L2) is inserted into each of E2s of Chikungunya virus (CHIKV) or Venezuelan equine encephalitis virus (VEEV).

In this embodiment, the E2 into which the antigen is inserted may consist of an amino acid sequence represented by SEQ ID Nos.:33-36; the E1 may consist of an amino acid sequence represented by SEQ ID No.:37; and the capsid may consist of an amino acid sequence represented by SEQ ID No.: 38; or
the E2 into which the antigen is inserted may consist of an amino acid sequence represented by SEQ ID Nos.:39-42; the E1 may consist of an amino acid sequence represented by SEQ ID No.:43; and the capsid may consist of an amino acid sequence represented by SEQ ID No.:44.

Further, regarding this embodiment, modified capsid of Chikungunya virus (CHIKV) or Venezuelan equine encephalitis virus (VEEV), modified E1 of Chikungunya virus (CHIKV) or Venezuelan equine encephalitis virus (VEEV) and modified E2 of Chikungunya virus (CHIKV) or Venezuelan equine encephalitis virus (VEEV) may be used for the virus like particle. For example, the modified capsid of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID No.:38 or SEQ ID No.:44; the modified E1 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID No.:37 or SEQ ID No.:43; and/or the modified E2 of Chikungunya virus (CHIKV) or Venezuelan equine encephalitis virus (VEEV) may have at least 70%, 75%, 80%, 85%, 90%, 95% or 98% amino acid sequence identity to the amino acid sequence represented by SEQ ID Nos.:33-36 or SEQ ID Nos.:39-42. Also, the modified capsid, E1 or E2 may be a mutant where at most 10% of the amino acids are deleted, substituted, and/or added based on the capsid consisting of an amino acid sequence represented by SEQ ID No.:38 or SEQ ID No.:44; E1 consisting of an amino acid sequence represented by SEQ ID No.:37 or SEQ ID No.:43; and/or E2 consisting of consisting of an amino acid sequence represented by SEQ ID Nos.:33-36 or SEQ ID Nos.:39-42.

Virus like particle may be prepared by introducing an expression vector comprising a DNA molecule having a nucleotide sequence encoding the virus like particle into a cell (e.g. 293 cell) and recovering the virus like particle from the conditioned medium using ultracentrifugal method.

(2) Nucleotide, Vector, Host Cell

In a second aspect, the present invention provides a nucleic acid molecule comprising a nucleotide sequence for expressing the disclosed particle which comprises a virus structural protein and an antigen selected from the group consisting of an antigen derived from PD-1 and an antigen derived from a ligand of PD-1.

The nucleic acid molecule provided by the present invention may be an isolated nucleic acid molecule for expressing a Chikungunya virus like particle or Venezuelan equine encephalitis virus like particle which comprises a virus structural protein and an antigen selected from the group consisting of an antigen derived from PD-1 and an antigen derived from a ligand of PD-1.

One skilled in the art may prepare the nucleic acid molecule provided by the present invention described above based on an exemplary nucleotide sequences that encode capsid and/or envelope represented by SEQ ID Nos.:63-64.

For example, one skilled in the art may introduce a nucleotide sequence encoding an antigen derived from PD-1 or PD-L1 into nucleotide sequence encoding E2 of Chikungunya or Venezuelan equine virus structural protein for preparing a nucleic acid molecule which is introduced into a vector to express Chikungunya virus like particle or Venezuelan equine virus like particle which comprises a virus structural protein and an antigen selected from the group consisting of an antigen derived from PD-1 and an antigen derived from a ligand of PD-1. Examples of the nucleotide sequence where antigen-derived sequence is introduced into E2 as described above include, but are not limited to, nucleotide sequence represented by SEQ ID Nos.:27 or 29 (for expressing Chikungunya virus like particle comprising PD-1 antigen); nucleotide sequence represented by SEQ ID No.:31 (for expressing Chikungunya virus like particle comprising PD-L1 antigen); nucleotide sequence represented by SEQ ID Nos.:28 or 30 (for expressing Venezuelan equine encephalitis virus like particle comprising PD-1 antigen); and nucleotide sequence represented by SEQ ID No.:32 (for expressing Venezuelan equine encephalitis virus like particle comprising PD-L1 antigen).

In one embodiment, the present invention provides a vector comprising the nucleic acid molecule as described above, wherein the vector optionally comprises an expression control sequence operably linked to the nucleic acid molecule.

Examples of an expression control sequence include, but are not limited to, promoter such as CMV promoter, phage lambda PL promoter, the E. coli lac, phoA and tac promoters, the SV40 early and late promoters, and promoters of retroviral LTRs.

In this embodiment, the vector comprising an expression control sequence operably linked to the nucleic acid molecule as described above can be used as an expression vector for preparing the particle provided by the present invention.

The expression vectors can be prepared by a person skilled in the art based on WO/2012/006180, the entire contents of which are incorporated by reference herein.

Examples of vectors which can be used for expressing a virus like particle comprising a fusion protein of a protein derived from Chikungunya virus (CHIKV) and an antigen derived from PD-1 include a vector shown in VLP31.11 vector (SEQ ID No.:45) and VLP274.11 vector (SEQ ID No.:46).

Examples of vectors which can be used for expressing a virus like particle comprising a fusion protein of a protein derived from Chikungunya virus (CHIKV) and an antigen derived from PD-L1 include a vector shown in VLP299.15 vector (SEQ ID No.:47).

Examples of vectors which can be used for expressing a virus like particle comprising a fusion protein of a protein derived from Venezuelan equine encephalitis virus (VEEV) and an antigen derived from PD-1 include a vector shown in VLP31.21 vector (SEQ ID No.:48) and VLP274.21 vector (SEQ ID No.:49).

Examples of vectors which can be used for expressing a virus like particle comprising a fusion protein of a protein derived from Venezuelan equine encephalitis virus (VEEV) and an antigen derived from PD-L1 include a vector shown in VLP299.25 vector (SEQ ID No.:50).

A nucleic acid molecule having at least 70%, 75%, 80%, 85%, 90%, 95% or 98% nucleotide sequence identity to the nucleic acid molecule having a nucleotide sequence represented by any one of SEQ ID Nos:45-50 and a nucleic acid molecule which may be a mutant where at most 10% of the amino acids are deleted, substituted, and/or added based on the nucleic acid molecule having a nucleotide sequence represented by any one of SEQ ID Nos.:45-50 are also provided by the present invention.

In addition, a recombinant cell prepared by introducing the above-described vector into a host cell is provided by the present invention. For example, CHO cells or 293 cells are used as host cells.

(3) Pharmaceutical Composition, Kit

In a third aspect, the present invention provides a pharmaceutical composition and a kit comprising a pharmaceutical composition, wherein the pharmaceutical composition comprises a particle comprising a virus structural protein and an antigen selected from the group consisting of an antigen derived from PD-1 and an antigen derived from a ligand of PD-1; or a nucleic acid molecule comprising a nucleotide sequence for expressing a particle which comprises a virus structural protein and an antigen selected from the group consisting of an antigen derived from PD-1 and an antigen derived from a ligand of PD-1; and a pharmaceutically acceptable carrier.

In one embodiment, the present invention provides a pharmaceutical composition or a kit comprising a pharmaceutical composition, wherein the pharmaceutical composition comprises the Alphavirus or Flavivirus virus like particle (e.g. Chikungunya virus like particle or Venezuelan equine encephalitis virus like particle) as described above or the nucleic acid molecule as described above; and a pharmaceutically acceptable carrier. The content of the Alphavirus or Flavivirus virus like particle and the content of the nucleic acid molecule may be 0.00001-1 w/w % of the pharmaceutical composition.

Dosage amount of the particle provided by the present invention (e.g. CHIKV VLP or VEEV VLP) may be 1-500 µg/day.

One or more PD-1 antigens or PD-1 ligand antigens may be used for one pharmaceutical composition provided by the present invention.

The pharmaceutical composition may further comprise adjuvant. Examples of adjuvant include, but are not limited to, Ribi solution (Sigma Adjuvant system, Sigma-Aldrich). The pharmaceutical composition provided by the present invention may contain buffering agent such as dibasic sodium phosphate hydrate, sodium dihydrogen phosphate and sodium chloride; and preserving agent such as thimerosal. In one embodiment, the pharmaceutical composition is an aqueous solution containing 0.001-1 w/w % of a particle (e.g. CHIKV VLP or VEEV VLP) comprising a virus structural protein and an antigen selected from the group consisting of an antigen derived from PD-1 or an antigen derived from a ligand of PD-1, 1-10 w/w % of buffering agent, 0.01-1 w/w % of adjuvant and 0.00001-0.001 w/w % of preserving agent.

A skilled person can prepare the pharmaceutical composition using conventional technique. For example, a particle (e.g. CHIKV VLP or VEEV VLP) comprising a virus structural protein and an antigen selected from the group consisting of an antigen derived from PD-1 or an antigen derived from a ligand of PD-1 is mixed with buffer solution having physiological pH (e.g. pH 5-9, pH7) to prepare the pharmaceutical composition provided by the present invention.

In one embodiment, the pharmaceutical composition is a vaccine or an immunostimulant comprising a particle comprising a virus structural protein and an antigen selected from the group consisting of an antigen derived from PD-1 and an antigen derived from a ligand of PD-1. For example, the vaccine composition provided by the present invention can be used for immunotherapy (e.g. treating cancer).

In one embodiment, the pharmaceutical composition is a DNA vaccine comprising a nucleic acid molecule comprising a nucleotide sequence for expressing a particle which comprises a virus structural protein and an antigen selected from the group consisting of an antigen derived from PD-1 and an antigen derived from a ligand of PD-1. In one embodiment, the DNA vaccine provided by the present invention comprises CpG containing oligonucleotide.

The pharmaceutical composition provided in the third aspect of the present invention can be administered one or more times. When the pharmaceutical composition provided in the third aspect of the present invention is administered more than one time, different particle provided in the first aspect of the present invention (e.g. CHIKV VLP or VEEV VLP) may be used for each of the administration. In one embodiment, combination of immunization using CHIKV VLP provided in the first aspect of the invention and immunization using VEEV VLP provided in the first aspect of the invention is employed. For example, CHIKV VLP provided in the first aspect of the present invention may be used for the 1st immunization and VEEV VLP provided in the first aspect of the present invention may be used for the 2nd immunization, or VEEV VLP provided in the first aspect of the present invention may be used for the 1st immunization and CHIKV VLP provided in the first aspect of the present invention may be used for the 2nd immunization.

A skilled person can determine timing of immunization using the composition or vaccine provided by the present invention. For example, 2nd immunization is performed 1, 2, 3, 4, 5, 6, 7, 8, 9 or 10 weeks after 1st immunization.

In one embodiment, the present invention provides a kit comprising
(a) a pharmaceutical composition comprising the particle provided in the first aspect of the present invention; and
(b) another pharmaceutical composition comprising the particle provided in the first aspect of the present invention, wherein the particle contained in (a) is a virus like particle which is different from the particle contained in (b). In this embodiment, the particle contained in (a) may be Chikungunya virus like particle and the particle contained in (b) may be Venezuelan equine encephalitis virus like particle.

In one embodiment, the present invention provides a kit comprising
(a) a pharmaceutical composition comprising the particle provided in the first aspect of the present invention; and
(b) another pharmaceutical composition comprising the particle provided in the first aspect of the present invention,
(c) one or more pharmaceutical composition, each of which comprises the particle provided in the first aspect of the present invention,
wherein (a) is used for priming immunization and (b) and (c) are used for boosting immunization; and the particle contained in (a) is a virus like particle which is different from the particle contained in (b); and the particle contained in (c) is different from the particle contained in (a) and (b), or the same as the particle contained in (a) or (b).

The respective pharmaceutical compositions contained in the above-described kit may be administered simultaneously, separately or sequentially.

The Alphavirus or Flavivirus virus like particle (e.g. Chikungunya virus or Venezuelan equine encephalitis virus) provided in the first aspect of the present invention or the nucleic acid molecule provided by the second aspect of the invention can be used for the pharmaceutical composition provided in the third aspect of the present invention.

For example, Chikungunya or Venezuelan equine encephalitis virus like particle comprising or consisting of:
one or more (e.g. 240) capsid of Chikungunya virus (CHIKV) or Venezuelan equine encephalitis virus (VEEV);
one or more (e.g. 240) E1 of Chikungunya virus (CHIKV) or Venezuelan equine encephalitis virus (VEEV); and
one or more (e.g. 240) E2 of Chikungunya virus (CHIKV) or Venezuelan equine encephalitis virus (VEEV), wherein PD-1 antigen is inserted into E2 of Chikungunya virus (CHIKV) or Venezuelan equine encephalitis virus (VEEV) may be used for preparing the composition or vaccine provided in the third aspect of the present invention. The E2 into which the antigen is inserted may consist of an amino acid sequence represented by SEQ ID Nos.: 33-36; the E1 may consist of an amino acid sequence represented by SEQ ID No.:37; and the capsid may consist of an amino acid sequence represented by SEQ ID No.:38; or the E2 into which the antigen is inserted may consist of an amino acid sequence represented by SEQ ID Nos.:39-42; the E1 may consist of an amino acid sequence represented by SEQ ID No.:43; and the capsid may consist of an amino acid sequence represented by SEQ ID No.:44.

(4) Use of the Disclosed Particle Etc.

In a forth aspect, the present invention provides a use of a particle comprising a virus structural protein and an antigen selected from the group consisting of an antigen derived from PD-1 and an antigen derived from a ligand of PD-1; or a nucleic acid molecule comprising a nucleotide sequence for expressing a particle which comprises a virus structural protein and an antigen selected from the group consisting of an antigen derived from PD-1 and an antigen derived from a ligand of PD-1 for the manufacture of a pharmaceutical composition or a kit for treating or preventing cancer or infectious disease; producing an antibody against PD-1 or a ligand of PD-1 in a mammal (e.g. human); modulating an immune response; immunostimulation; inhibiting an interaction between PD-1 and a ligand of PD-1; or inhibiting a PD-1 activity. A method of treating or preventing cancer or infectious disease; producing an antibody against PD-1 or a ligand of PD-1 in a mammal (e.g. human); modulating an immune response; immunostimulation; inhibiting an interaction between PD-1 and a ligand of PD-1; or inhibiting a PD-1 activity comprising administering an effective amount of the particle or the pharmaceutical composition disclosed herein to a subject in need thereof is also provided.

The pharmaceutical composition may be administered to a mammal (e.g. human) intramuscularly (i.m.), intracutaneously (i.c.), subcutaneously (s.c.), intradermally (i.d.) or intraperitoneally (i.p.).

In one embodiment, the pharmaceutical composition is a vaccine, which can be applied to immunotherapy (e.g. treating cancer).

Examples of the cancer which may be treated include, but are not limited to, melanoma, renal cancer, prostate cancer, breast cancer, colon cancer and non-small cell lung cancer. Other examples of the cancer include, but are not limited to, include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations thereof.

Examples of infectious disease which may be treated include, but are not limited to, HIV, Influenza, Herpes, Güardia, Malaria, *Leishmania*, the pathogenic infection by the virus Hepatitis (A, B and C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, *rubella* virus, parvovirus, vaccinia virus, HTLV virus, dengue virus, papillomavirus, molluscum virus, poliovirus, rabies virus, JC virus and arboviral encephalitis virus, pathogenic infection by the bacteria *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria, pathogenic infection by the fungi *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis*.

When a pharmaceutical composition comprising a virus structural protein and an antigen selected from the group consisting of an antigen derived from PD-1 or a ligand of PD-1 is administered to a mammal (e.g. human), an antibody against PD-1 or a ligand of PD-1 is produced in blood of the mammal. The produced antibody may modulate an immune response; show immunostimulating effects; inhibit an interaction between PD-1 and a ligand of PD-1 (e.g. PD-L1, PD-L2); or inhibit a PD-1 activity.

The produced antibody may be humanized using a conventional technique. Using the particle provided in a first aspect of the present invention, monoclonal antibody or polyclonal antibody can be prepared. In one embodiment, the present invention provides a method for producing an antibody against PD-1 or a ligand of PD-1 comprising administering the particle provided in a first aspect of the present invention to a non-human mammal and humanizing non-human mammal produced antibody.

As used herein, the term "antibody" refers to molecules which are capable of binding an epitope or antigenic determinant. The term is meant to include whole antibodies and antigen-binding fragments thereof, including single-chain antibodies. Such antibodies include human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies can be from any animal origin including birds and mammals. Preferably, the antibodies are mammalian e.g. human, murine, rabbit, goat, guinea pig, camel, horse and the like, or other suitable animals e.g. chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598, the disclosure of which is incorporated herein by reference in its entirety.

The term "PD-1 activity" refers to one or more immunoregulatory activities associated with PD-1. For example, PD-1 is a negative regulator of the TcR/CD28-mediated immune response. Thus, examples of modulation of immune response include, but are not limited to, enhancing the TcR/CD28-mediated immune response.

In one embodiment, the present invention provides a method for producing Chikungunya or Venezuelan equine encephalitis virus like particle provided in a first aspect of the present invention, comprising preparing a vector designed for expression of the particle; culturing a cell which is transfected with the vector to express the particle; and recovering the particle. In this embodiment, transfection can be conducted using a conventional method. Cells using for the transfection may be 293 cells. Recovering VLP may include collecting a conditioned medium after cells are transfected with a vector, and may further include purify VLP from the conditioned medium using ultracentrifugation.

The following exemplary embodiments (1)-(35) are further provided by the present invention:

(1) A particle comprising a virus structural protein and at least one antigen selected from the group consisting of an antigen derived from PD-1 and an antigen derived from a ligand of PD-1;

(2) A particle, which is a derivative of the article according to (1);

(3) The particle according to (1) or (2), wherein the antigen is an antigen derived from PD-1, PD-L1 or PD-L2;

(4) The particle according to any one of (1)-(3), wherein administration of the particle to animals induces an antibody against the antigen and the antibody blocks PD-1 and PD-L1 interaction or PD-1 and PD-L2 interaction;

(5) The particle according to any one of (1)-(4), wherein said particle is virus like particle;

(6) The particle according to any one of (1)-(5), wherein said particle is a virus like particle derived from alphavirus or flavivirus;

(7) The particle according to any one of (1)-(6), wherein said particle is a virus like particle derived from Chikungunya virus or Venezuelan equine encephalitis virus;

(8) The particle according to any one of (1)-(7), wherein the virus structural protein comprises at least one first attachment site and the at least one antigen comprises at least one second attachment site, and wherein the virus structural protein and the antigen are linked through the at least one first and the at least one second attachment site, and wherein the particle is virus like particle;

(9) The particle according to any one of (1)-(8), wherein the virus structural protein comprises the capsid and/or the envelope proteins E1 and E2;

(10) The particle according to (9), wherein at least one antigen derived from PD-1 or at least one antigen derived from PD-L1 is inserted into E2 of the envelope protein;

(11) The particle according to any one of (1)-(10), wherein the virus structural protein is a protein derived from Chikungunya virus (CHIKV) or Venezuelan equine encephalitis virus (VEEV);

(12) The particle according to any one of (1)-(11), wherein the particle is Chikungunya virus like particle consisting of one or more envelope protein E2 into which the antigen derived from PD-1 is inserted, one or more envelope protein E1 and one or more capsid, and wherein the envelope protein E2 into which the antigen derived from PD-1 is inserted consists of an amino acid sequence represented by SEQ ID Nos.:33-35; the envelope protein E1 consists of an amino acid sequence represented by SEQ ID No.:37; and the capsid consists of an amino acid sequence represented by SEQ ID No.:38;

(13) The particle according to any one of (1)-(11), wherein the particle is Venezuelan equine virus like particle consisting of one or more envelope protein E2 into which the antigen derived from PD-1 is inserted, one or more envelope protein E1 and one or more capsid, and wherein the envelope protein E2 into which the antigen derived from PD-1 is inserted consists of an amino acid sequence represented by SEQ ID Nos.:39-41; the envelope protein E1 consists of an amino acid sequence represented by SEQ ID No.:43; and the capsid consists of an amino acid sequence represented by SEQ ID No.:44;

(14) The particle according to any one of (1)-(11), wherein the particle is Chikungunya virus like particle consisting of one or more envelope protein E2 into which the antigen derived from PD-L1 is inserted, one or more envelope protein E1 and one or more capsid, and wherein the envelope protein E2 into which the antigen derived from PD-L1 is inserted consists of an amino acid sequence represented by SEQ ID No.:36; the envelope protein E1 consists of an amino acid sequence represented by SEQ ID No.:37; and the capsid consists of an amino acid sequence represented by SEQ ID No.:38;

(15) The particle according to any one of (1)-(11), wherein the particle is Venezuelan equine virus like particle consisting of one or more envelope protein E2 into which the antigen derived from PD-L1 is inserted, one or more envelope protein E1 and one or more capsid, and wherein the envelope protein E2 into which the antigen derived from PD-L1 is inserted consists of an amino acid sequence represented by SEQ ID No.:42; the envelope protein E1 consists of an amino acid sequence represented by SEQ ID No.:43; and the capsid consists of an amino acid sequence represented by SEQ ID No. 44;

(16) A particle consisting of an amino acid sequence which has a sequence identity of 90% or more (or 95% or more) with an amino acid sequence of the particle according to any one of (1)-(15).

(17) An isolated nucleic acid molecule comprising a nucleotide sequence for expressing the particle according to any one of (1)-(16);

(18) An isolated nucleic acid molecule consisting of a nucleotide sequence which has a sequence identity of 90% or more with a nucleotide sequence represented by any one of SEQ ID Nos.:27-32;

(19) The nucleic acid molecule according to (18), wherein the nucleic acid molecule consists of a nucleotide sequence represented by any one of SEQ ID Nos.:27-32;

(20) A vector comprising the nucleic acid molecule according to any one of (17)-(19), wherein the vector optionally comprises an expression control sequence operably linked to the nucleic acid molecule (e.g. a vector consisting of a nucleotide sequence represented by SEQ ID Nos. 45, 46, 47, 48, 49 or 50);

(21) A pharmaceutical composition comprising:
(a) the particle according to any one of (1)-(16), the nucleic acid molecule according to any one of (17)-(19) and/or the vector according to (20); and
(b) a pharmaceutically acceptable carrier;

(22) The pharmaceutical composition (e.g. vaccine) according to (16), wherein the pharmaceutical composition comprises the particle according to any one of (1)-(16) and a pharmaceutically acceptable carrier;
(23) Use of the particle according to any one of (1)-(16), the nucleic acid molecule according to any one of (17)-(19) and/or the vector according to (20) for the manufacture of a pharmaceutical composition or a kit for treating or preventing cancer or infectious disease; producing an antibody against PD-1 or a ligand of PD-1 in a mammal; modulating an immune response; immunostimulation; inhibiting an interaction between PD-1 and a ligand of PD-1; or inhibiting a PD-1 activity;
(24) The use according to (23), wherein the pharmaceutical composition is administered to inhibit binding of PD-L1 and/or PD-L2 to PD-1;
(25) The use according to (23) or (24), wherein the cancer is melanoma, renal cancer, prostate cancer, breast cancer, colon cancer or non-small cell lung cancer;
(26) The use according to (23) or (24), wherein the cancer is selected from the group consisting of bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations thereof;
(27) The use according to (23) or (24), wherein the infectious disease is selected from the group consisting of HIV, Influenza, Herpes, Güardia, Malaria, *Leishmania*, the pathogenic infection by the virus Hepatitis (A, B and C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, *rubella* virus, parvovirus, vaccinia virus, HTLV virus, dengue virus, papillomavirus, molluscum virus, poliovirus, rabies virus, JC virus and arboviral encephalitis virus, pathogenic infection by the bacteria *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria, pathogenic infection by the fungi *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*;
(28) A kit comprising
(a) a pharmaceutical composition comprising the particle according to any one of (1)-(16); and
(b) another pharmaceutical composition comprising the particle according to any one of (1)-(16),
wherein the particle contained in (a) is a virus like particle which is different from the particle contained in (b);
(29) The kit according to (28), wherein the particle contained in (a) is Chikungunya virus like particle and the particle contained in (b) is Venezuelan equine encephalitis virus like particle, or the particle contained in (a) is Venezuelan equine encephalitis virus like particle and the particle contained in (b) is Chikungunya virus like particle;
(30) The kit according to (28) or (29), further comprising (c) one or more pharmaceutical compositions, each of which comprises the particle according to any one of (1)-(16), wherein (a) is used for priming immunization and (b) and (c) are used for boosting immunization, and the particle contained in (c) is different from the particle contained in (a) and (b), or the same as the particle contained in (a) or (b);
(31) The kit according to any one of (28)-(30), wherein the respective pharmaceutical compositions are administered simultaneously, separately or sequentially;
(32) A method of treating or preventing cancer or infectious disease; producing an antibody against PD-1 or a ligand of PD-1 in a mammal; modulating an immune response; immunostimulation; inhibiting an interaction between PD-1 and a ligand of PD-1; or inhibiting a PD-1 activity, comprising administering an effective amount of the particle according to any one of (1)-(16), the nucleic acid molecule according to any one of (17)-(20), the vector according to (20) or the pharmaceutical composition according to (21) or (22) to a subject in need thereof;
(33) The method according to (32), wherein the cancer is selected from the cancers described in (25) or (26);
(34) The method according to (32), wherein the infectious disease is selected from the infectious disease described in (27);
(35) A method for producing Chikungunya virus like particle or Venezuelan equine encephalitis virus like particle, comprising culturing a cell which is transfected with the vector according to (20) to express the particle; and purifying the particle using ultracentrifugation.

The present invention will be described in detail with reference to the following examples, which, however, are not intended to limit the scope of the present invention.

EXAMPLES

Example 1

Preparation of Chikungunya Virus (CHIKV) Like Particle Comprising a Virus Structural Protein and a Fragment of PD-1 Antigen The following polynucleotides of PD-1 were used to be inserted into VLP_CHI 532 vector (SEQ ID No.:25). N terminal linker is SGG in amino acid sequence (TCCG- GAGGA in nuclear sequence) and C terminal linker is GGS in amino acid sequence (GGAGGATCC in nuclear sequence).

1. VLP31 (PD-1 No. 1 sequence): A sequence of a PD-1 fragment attaching linker, which was used for an antigen:

Nuclear sequence
(SEQ ID No.: 51)
Tccggaggactaaactggtaccgcatgagccccagcaaccagacggaca
agctggccgccttcggaggatcc Amino acid sequence
(SEQ ID No.: 52)
sgglnwyrmspsnqtdklaafggs 2. VLP32 (PD-1 No. 2 sequence): Another sequence of a PD-1 fragment attaching linker, which was used for an antigen:

Nuclear Sequence
(SEQ ID No.: 53)
Tccggaggaatgctaaactggtaccgcatgagccccagcaaccagacgg
acaagctggccgccttctcaggaggatcc Amino acid sequence
(SEQ ID No.: 54)
sggmlnwyrmspsnqtdklaafsggs 3. VLP33 (PD-1 No. 3 sequence): Another sequence of a PD-1 fragment attaching linker, which was used for an antigen:

Nuclear Sequence
(SEQ ID No.: 55)
Tccggaggagtgctaaactggtaccgcatgagccccagcaaccagacgg
acaagctggccgccttccccggaggatcc Amino Acid sequence
(SEQ ID No.: 56)
sggvlnwyrmspsnqtdklaafpggs The respective polynucleotides was inserted between the codons encoding Ser at 531-position and Asn at 532-position of SEQ ID No. 2 to construct a plasmid (hereinafter referred to as VLP31_11, VLP32_11 or VLP33_11) for expressing Chikungunya virus like particle where the modified PD-1-derived peptide is inserted into E2 of Chikungunya virus structural protein.

293F cells (Lifetechnology) were transfected with the plasmid using PEI (GE Healthcare) or GeneX (ATCC). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles.

The expression of VLP comprising VLP31, 32 or 33 conjugated with Chikungunya virus structural protein was confirmed by Western Blot using an antibody specific for CHIKV (ATCC: VR-1241AF).

Example 2

Preparation of Venezuelan Equine Encephalitis Virus (VEEV) Like Particle Comprising a Virus Structural Protein and a Fragment of PD-1 Antigen The same polynucleotides of PD-1 used in EXAMPLE 1 were used to be inserted into VLP_VEEV VLP 518 vector (SEQ ID No.:26). N terminal linker and C terminal linker are same in EXAMPLE 1.

The respective polynucleotides was inserted between the codons encoding Ser at 518-position and Ser at 519-position of SEQ ID No. 3 to construct a plasmid (hereinafter referred to as VLP31_21, VLP32_21 or VLP33_21) for expressing Venezuelan equine encephalitis virus like particle where the modified PD-1-derived peptide is inserted into E2 of Venezuelan equine encephalitis structural protein.

293F cells were transfected with the plasmid like Example 1. The expression of VLP comprising VLP 31, 32 or 33 conjugated with Venezuelan equine encephalitis virus structural protein was confirmed by Western Blot using an antibody specific for VEEV.

Example 3

Preparation of Chikungunya Virus (CHIKV) Like Particle and Venezuelan Equine Encephalitis Virus (VEEV) Like Particle Comprising a Virus Structural Protein and a Fragment of PD-1 Antigen or PD-L1 Antigen The following polynucleotides of mouse PD-1 and mouse PD-L1 were used to be inserted into VLP_CHI 532 vector (SEQ ID No.:25) or to be inserted into VLP_VEEV VLP 518 vector (SEQ ID No.:26). N terminal linker is SGG in amino acid sequence (TCCGGAGGA in nuclear sequence) and C terminal linker is GGS in amino acid sequence (GGAGGATCC in nuclear sequence).

1. VLP299 (mousePD-L1 sequence): A sequence of a fragment of mouse PD-L1 Domain3S attaching linker, which was used for an antigen:

Nuclear Sequence
(SEQ ID No.: 57)
Tccggaggatgcatcatcagctacggcggagccgactacggaggatcc Amino Acid sequence
(SEQ ID No.: 58)
SGG-ciisyggadyC-GGS 2. VLP274 (mousePD-1 sequence): A sequence of a fragment of mouse PD-1 domain2short attaching linker, which was used for an antigen:

Nuclear Sequence
(SEQ ID No.: 59)
Tccggaggaggcgccatcagcctgcaccccaaggccaagatcgaggaat
ctggaggatcc Amino Acid sequence
(SEQ ID No.: 60)
SGG-gaislhpkakiees-GS 3. VLP275 (mousePD-1 sequence): A sequence of a fragment of mouse PD-1 domain2short_v2 attaching linker, which was used for an antigen:

Nuclear Sequence
(SEQ ID No.: 61)
Tccggaggatgtggcgccatcagcctgcaccccaaggccaagatcgag
gaaggaggatcc Amino Acid sequence
(SEQ ID No.: 62)
SGG-cgaislhpkakieeC-GGS The respective polynucleotides was inserted between the codons encoding Ser at 531-position and Asn at 532-position of SEQ ID No. 2 to construct a plasmid (hereinafter referred to as VLP299_15, VLP299_25 for VLP299-inserted vector; VLP274_11, VLP274_15 for VLP274-inserted vector; VLP275_11, VLP275_15 for VLP275-inserted vector) for expressing Chikungunya virus like particle where the modified PD-1-derived peptide or the modified PD-L1-derived peptide is inserted into E2 of Chikungunya virus structural protein.

293F cells were transfected with the plasmid like Example 1. The expression of VLP comprising VLP299, 274 or 275 conjugated with Chikungunya virus structural protein was confirmed by Western Blot using an antibody specific for CHIKV or VEEV.

Example 4

Immunogenicity of PD-1

The following polynucleotides of human PD-1, which is also found in the mouse PD-1 gene, was used to be inserted into VLP_CHI 532 vector (SEQ ID No.:25) or to be inserted into VLP_VEEV VLP 518 vector (SEQ ID No.:26). N terminal linker is SGG in amino acid sequence (TCCG-GAGGA in nuclear sequence) and C terminal linker is GGS in amino acid sequence (GGAGGATCC in nuclear sequence).

```
Nuclear Sequence
                                      (SEQ ID No.: 51)
Tccggaggactaaactggtaccgcatgagccccagcaaccagacggaca
agctggccgccttcggaggatcc Amino Acid sequence
                                      (SEQ ID No.: 52)
SGGLNWYRMSPSNQTDKLAAFGGS
```

The polynucleotides was inserted between the codons encoding Ser at 531-position and Asn at 532-position of SEQ ID No.:2 to construct a plasmid (hereinafter referred to pCHIKV-hPD-1) for expressing Chikungunya virus like particle where the modified PD-1-derived peptide is inserted into E2 of Chikungunya virus structural protein. Also, the polynucleotides was inserted between the codons encoding Ser at 518-position and Ser at 519-position of SEQ ID No.:3 to construct a plasmid (hereinafter referred to as pVEEV-hPD-1) for expressing Venezuelan equine encephalitis virus like particle where the modified PD-1-derived peptide is inserted into E2 of Venezuelan equine encephalitis structural protein.

293F cells (Lifetechnology) were transfected with the plasmid using PEI (GE Healthcare) or GeneX (ATCC). 4 days after the transfection, the conditioned medium was collected and centrifuged at 3000 rpm for 15 minutes to separate it from cells. The supernatant was filtrated using 0.45 μm filter to obtain virus like particles. The virus like particles were concentrated using TFF column and purified using QXL column (GE Healthcare) to obtain purified virus like particles. The purified virus like particles were further concentrated using spin column (Molecular Weight-cutoff: 100 kDa) to prepare the virus like particles for the immunization (CHIKV-hPD-1 and VEEV-hPD-1).

The mice (4 week old male) were immunized with the VEEV-hPD-12 times at 0 and 8 week (20 ug VLP per mouse) by intramuscle injection with Adjuvant Ribi, and immunized with CHIKV-hPD-1 once at 4 week (20 ug VLP per mouse) by intramuscle injection with Adjuvant Ribi (Sigma Adjuvant system, Sigma-Aldrich). The blood was taken at 10 weeks after the first immunization.

96 well ELISA plate were coated with 50 ng of Recombinant N-terminal fragment of PD-1 (1-167aa) or PD-1-Fc conjugate in 100 ul PBS buffer pre well. The Plates after 2 hours incubation were washed three times TBS buffer containing 0.05% Tween-20 and blocked with TBS buffer containing 0.05% Tween-20 and 5% dry milk. The heat inactivated diluted serum from mice were added in the blocking buffer and incubated for 1 h at room temperature. After washing three times, peroxidase labeled goat anti-mouse IgG was added at 1:4000 dilution and incubated for 1 h at room temperature. After washing three times, Peroxidase substrate was added for development and incubated for 10 mins and 2N H2SO4 was added to stop the development. The data were analyzed using Gen5 (BioTek) and GraphPad Prism6 (GraphPad software Inc).

Figure 2:
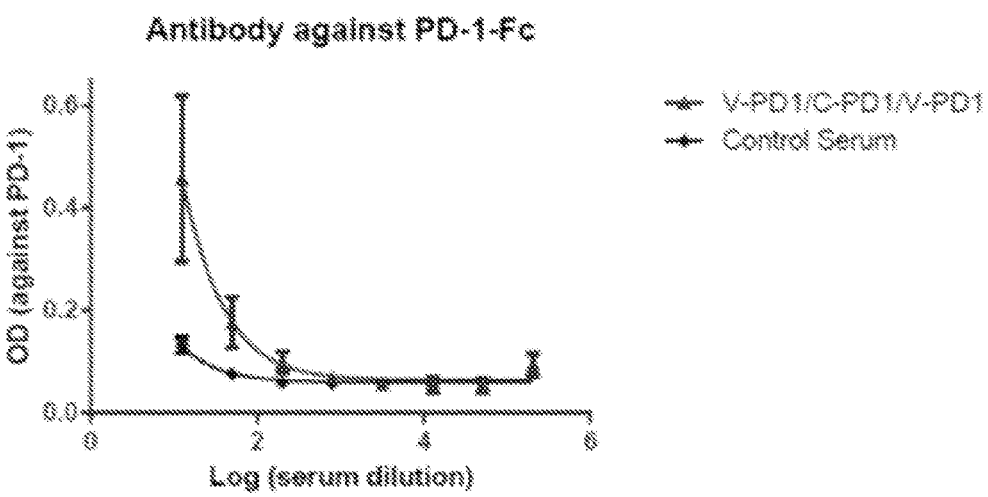
FIG. 2 shows results of ELISA where an antibody which binds to PD-1-Fc was detected.

The immunogenicities are shown in FIGS. 1 and 2. As seen from FIGS. 1 and 2, induction of antibodies against PD-1 was found in the serum of mice immunized with CHIKV-PD-1 and VEEV-PD-1.

Example 5

Preparation of a Pharmaceutical Composition Comprising Chikungunya Virus (CHIKV) Like Particle or Venezuelan Equine Encephalitis Virus (VEEV) Like Particle Comprising a Virus Structural Protein and a Fragment of PD-1 Antigen Chikungunya virus (CHIKV) like particle comprising a virus structural protein and a fragment of PD-1 antigen and Venezuelan equine encephalitis virus (VEEV) like particle a virus structural protein and a fragment of PD-1 antigen were prepared according to Example 4.

To prepare a pharmaceutical composition which is a vaccine composition, 80 μg of each of the prepared particles was mixed with 1 ml of Sucrose Phosphate Solution, pH 7.2, Endotoxin Free (Teknova, SP buffer).

The invention claimed is:

1. A virus-like particle comprising a virus structural protein of an alphavirus or a flavivirus, and an antigen selected from the group consisting of (a)-(c):
   (a) an antigen which comprises a 10-300 amino acid fragment of human Programmed Death-1 (PD-1), or which comprises an amino acid sequence having at least 90% amino acid identity to said fragment of human PD-1;
   (b) an antigen which comprises a 10-300 amino acid fragment of human Programmed Death-Ligand 1 (PD-L1), or which comprises an amino acid sequence having at least 90% amino acid identity to said fragment of human PD-L1; and
   (c) an antigen which comprises a 10-300 amino acid fragment of human Programmed Death-Ligand 2 (PD-L2), or which comprises an amino acid sequence having at least 90% amino acid identity to said fragment of human PD-L2.

2. The virus-like particle according to claim 1, wherein said virus-like particle is an alphavirus virus-like particle, and wherein said virus structural protein comprises at least one alphavirus protein selected from the group consisting of: a capsid protein, an E1 envelope protein, and an E2 envelope protein.

3. The virus-like particle according to claim 2, wherein said virus-like particle comprises an E2 envelope protein, and wherein said antigen is inserted into said E2 envelope protein to form a fusion protein.

4. The virus-like particle according to claim 1, wherein the virus-like particle is a Chikungunya virus-like particle consisting of one or more envelope protein E2 into which the antigen is inserted, one or more envelope protein E1 and one or more capsid, and
   wherein the envelope protein E2 into which the antigen is inserted consists of an amino acid sequence represented by SEQ ID NOs: 33-35; the envelope protein E1 consists of an amino acid sequence represented by SEQ ID NO: 37; and the capsid consists of an amino acid sequence represented by SEQ ID NO: 38.

5. The virus-like particle according to claim 1, wherein the virus-like particle is a Venezuelan equine encephalitis virus-like particle consisting of one or more envelope protein E2 into which the antigen is inserted, one or more envelope protein E1 and one or more capsid, and
   wherein the envelope protein E2 into which the antigen is inserted consists of an amino acid sequence represented by SEQ ID NOs: 39-41; the envelope protein E1 consists of an amino acid sequence represented by SEQ ID NO: 43; and the capsid consists of an amino acid sequence represented by SEQ ID NO: 44.

6. The virus-like particle according to claim 1, wherein the virus-like particle is a Chikungunya virus-like particle consisting of one or more envelope protein E2 into which the antigen is inserted, one or more envelope protein E1 and one or more capsid, and
   wherein the envelope protein E2 into which the antigen is inserted consists of an amino acid sequence represented by SEQ ID NO: 36; the envelope protein E1 consists of an amino acid sequence represented by SEQ ID NO: 37; and the capsid consists of an amino acid sequence represented by SEQ ID NO: 38.

7. The virus-like particle according to claim 1, wherein the virus-like particle is a Venezuelan equine encephalitis virus-like particle consisting of one or more envelope protein E2 into which the antigen is inserted, one or more envelope protein E1 and one or more capsid, and wherein the envelope protein E2 into which the antigen is inserted consists of an amino acid sequence represented by SEQ ID NO: 42; the envelope protein E1 consists of an amino acid sequence represented by SEQ ID NO: 43; and the capsid consists of an amino acid sequence represented by SEQ ID NO: 44.

8. A pharmaceutical composition comprising:
   (a) virus-like particle according to claim 1; and
   (b) a pharmaceutically acceptable carrier.

9. The virus-like particle according to claim 2, wherein said alphavirus is Chikungunya virus (CHIKV) or Venezuelan equine encephalitis virus (VEEV).

10. The virus-like particle according to claim 3, wherein said antigen is directly fused to said E2 envelope protein.

11. The virus-like particle according to claim 3, wherein one or two linkers intervene between the N-terminal residue of said antigen and said E2 envelope protein, and/or between the C-terminal residue of said antigen and said E2 envelope protein.

12. The virus-like particle according to claim 3, wherein said fusion protein comprises an amino acid sequence selected from the group consisting of SEQ ID NOs: 33-36 and 39-42.

13. The virus-like particle according to claim 3, wherein said fusion protein comprises an amino acid sequence having 90% or more sequence identity to an amino acid sequence selected from the group consisting of SEQ ID NOs: 33-36 and 39-42.

14. The virus-like particle according to claim 9, wherein said antigen is inserted into E2 of a VEEV structural protein that comprises the amino acid sequence of SEQ ID NO: 3, and wherein said antigen is inserted between residues 515 and 516 of SEQ ID NO: 3, between residues 516 and 517 of SEQ ID NO: 3, between residues 517 and 518 of SEQ ID NO: 3, between residues 518 and 519 of SEQ ID NO: 3, between residues 519 and 520 of SEQ ID NO: 3, between residues 536 and 537 of SEQ ID NO: 3, between residues 537 and 538 of SEQ ID NO: 3, or between residues 538 and 539 of SEQ ID NO: 3.

15. The virus-like particle according to claim 9, wherein said antigen is inserted into E2 of a CHIKV structural protein that comprises the amino acid sequence of SEQ ID NO: 1 or 2, and wherein said antigen is inserted between residues 519 and 520 of SEQ ID NO: 1 or 2, between residues 529 and 530 of SEQ ID NO: 1 or 2, between residues 530 and 531 of SEQ ID NO: 1 or 2, between residues 531 and 532 of SEQ ID NO: 1 or 2, between residues 509 and 510 of SEQ ID NO: 1 or 2, between residues 510 and 511 of SEQ ID NO: 1 or 2, or between residues 511 and 512 of SEQ ID NO: 1 or 2.

16. The virus-like particle according to claim 1, wherein said antigen is selected from the group consisting of (a) said antigen which comprises a 10-300 amino acid fragment of human PD-1, or which comprises an amino acid sequence having at least 90% amino acid identity to said fragment of human PD-1, and (b) said antigen which comprises a 10-300 amino acid fragment of human PD-L1, or which comprises an amino acid sequence having at least 90% amino acid identity to said fragment of human PD-L1.

17. The virus like particle of claim 1 comprising an antigen, wherein said antigen comprising a polypeptide sequence having at least 10 consecutive residues of a sequence selected from the group consisting of SEQ ID NOs: 4-6, 9-11, 14-18 and 19.

18. A kit comprising
(a) a pharmaceutical composition comprising the virus-like particle according to claim 1; and
(b) another pharmaceutical composition comprising the virus-like particle according to claim 1,
wherein the virus-like particle contained in (a) is a virus-like particle which is different from the virus-like particle contained in (b).

19. The kit according to claim 18, wherein the virus-like particle contained in (a) is a Chikungunya virus-like particle and the virus-like particle contained in (b) is a Venezuelan equine encephalitis virus-like particle, or the virus-like particle contained in (a) is a Venezuelan equine encephalitis virus-like particle and the virus-like particle contained in (b) is a Chikungunya virus-like particle.

20. A method for treating cancer or infectious disease; producing an antibody against PD-1 or a ligand of PD-1 in a mammal;
modulating an immune response; immunostimulation; inhibiting an interaction between PD-1 and a ligand of PD-1; or inhibiting a PD-1 activity, comprising administering the virus-like particle according to claim 1.

21. An isolated nucleic acid molecule comprising a nucleotide sequence that encodes the entire virus-like particle according to claim 1.

22. A vector comprising the nucleic acid molecule according to claim 21, wherein the vector optionally comprises an expression control sequence operably linked to the nucleic acid molecule.

* * * * *

SEQUENCE LISTING

```
<160> NUMBER OF SEQ ID NOS: 64

<210> SEQ ID NO 1
<211> LENGTH: 1248
<212> TYPE: PRT
<213> ORGANISM: Chikungunya virus

<400> SEQUENCE: 1

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
```

```
                        20                  25                  30
Arg Pro Gln Arg Gln Ala Gly Gln Leu Ala Gln Leu Ile Ser Ala Val
                35                  40                  45
Asn Lys Leu Thr Met Arg Ala Val Pro Gln Gln Lys Pro Arg Arg Asn
        50                  55                  60
Arg Lys Asn Lys Lys Gln Lys Gln Lys Gln Ala Pro Gln Asn Asn
65                  70                  75                  80
Thr Asn Gln Lys Lys Gln Pro Pro Lys Lys Pro Ala Gln Lys Lys
                85                  90                  95
Lys Lys Pro Gly Arg Arg Glu Arg Met Cys Met Lys Ile Glu Asn Asp
                100                 105                 110
Cys Ile Phe Glu Val Lys His Glu Gly Lys Val Thr Gly Tyr Ala Cys
                115                 120                 125
Leu Val Gly Asp Lys Val Met Lys Pro Ala His Val Lys Gly Thr Ile
                130                 135                 140
Asp Asn Ala Asp Leu Ala Lys Leu Ala Phe Lys Arg Ser Ser Lys Tyr
145                 150                 155                 160
Asp Leu Glu Cys Ala Gln Ile Pro Val His Met Lys Ser Asp Ala Ser
                165                 170                 175
Lys Phe Thr His Glu Lys Pro Glu Gly Tyr Tyr Asn Trp His His Gly
                180                 185                 190
Ala Val Gln Tyr Ser Gly Gly Arg Phe Thr Ile Pro Thr Gly Ala Gly
                195                 200                 205
Lys Pro Gly Asp Ser Gly Arg Pro Ile Phe Asp Asn Lys Gly Arg Val
                210                 215                 220
Val Ala Ile Val Leu Gly Gly Ala Asn Glu Gly Ala Arg Thr Ala Leu
225                 230                 235                 240
Ser Val Val Thr Trp Asn Lys Asp Ile Val Thr Lys Ile Thr Pro Glu
                245                 250                 255
Gly Ala Glu Glu Trp Ser Leu Ala Ile Pro Val Met Cys Leu Leu Ala
                260                 265                 270
Asn Thr Thr Phe Pro Cys Ser Gln Pro Pro Cys Thr Pro Cys Cys Tyr
                275                 280                 285
Glu Lys Glu Pro Glu Glu Thr Leu Arg Met Leu Glu Asp Asn Val Met
                290                 295                 300
Arg Pro Gly Tyr Tyr Gln Leu Leu Gln Ala Ser Leu Thr Cys Ser Pro
305                 310                 315                 320
His Arg Gln Arg Arg Ser Thr Lys Asp Asn Phe Asn Val Tyr Lys Ala
                325                 330                 335
Thr Arg Pro Tyr Leu Ala His Cys Pro Asp Cys Gly Glu Gly His Ser
                340                 345                 350
Cys His Ser Pro Val Ala Leu Glu Arg Ile Arg Asn Glu Ala Thr Asp
                355                 360                 365
Gly Thr Leu Lys Ile Gln Val Ser Leu Gln Ile Gly Ile Lys Thr Asp
                370                 375                 380
Asp Ser His Asp Trp Thr Lys Leu Arg Tyr Met Asp Asn His Met Pro
385                 390                 395                 400
Ala Asp Ala Glu Arg Ala Gly Leu Phe Val Arg Thr Ser Ala Pro Cys
                405                 410                 415
Thr Ile Thr Gly Thr Met Gly His Phe Ile Leu Ala Arg Cys Pro Lys
                420                 425                 430
Gly Glu Thr Leu Thr Val Gly Phe Thr Asp Ser Arg Lys Ile Ser His
                435                 440                 445
```

-continued

```
Ser Cys Thr His Pro Phe His His Asp Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                    485                 490                 495

Pro Pro Asp Thr Pro Asp Arg Thr Leu Met Ser Gln Gln Ser Gly Asn
                500                 505                 510

Val Lys Ile Thr Val Asn Gly Gln Thr Val Arg Tyr Lys Cys Asn Cys
            515                 520                 525

Gly Gly Ser Asn Glu Gly Leu Thr Thr Thr Asp Lys Val Ile Asn Asn
530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
                580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
                660                 665                 670

Ala His Gly His Pro His Glu Ile Ile Leu Tyr Tyr Tyr Glu Leu Tyr
            675                 680                 685

Pro Thr Met Thr Val Val Val Ser Val Ala Thr Phe Ile Leu Leu
690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
                740                 745                 750

Glu Ala Ala Ile Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
        770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860
```

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
            885                 890                 895

Met Trp Gly Gly Ala Tyr Cys Phe Cys Asp Ala Glu Asn Thr Gln Leu
        900                 905                 910

Ser Glu Ala His Val Glu Lys Ser Glu Ser Cys Lys Thr Glu Phe Ala
    915                 920                 925

Ser Ala Tyr Arg Ala His Thr Ala Ser Ala Ser Ala Lys Leu Arg Val
930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
        995                 1000                1005

Phe Gly Asp Ile Gln Ser Arg Thr Pro Glu Ser Lys Asp Val Tyr
    1010                1015                1020

Ala Asn Thr Gln Leu Val Leu Gln Arg Pro Ala Val Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Val Asn Cys Ala Val Gly
    1070                1075                1080

Asn Met Pro Ile Ser Ile Asp Ile Pro Glu Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Ala Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 2
<211> LENGTH: 1248
<212> TYPE: PRT

<213> ORGANISM: Chikungunya virus

<400> SEQUENCE: 2

```
Met Glu Phe Ile Pro Thr Gln Thr Phe Tyr Asn Arg Arg Tyr Gln Pro
  1               5                  10                  15
Arg Pro Trp Ala Pro Arg Pro Thr Ile Gln Val Ile Arg Pro Arg Pro
                 20                  25                  30
Arg Pro Gln Arg Gln Ala Gly Gln Leu Ala Gln Leu Ile Ser Ala Val
                 35                  40                  45
Asn Lys Leu Thr Met Arg Ala Val Pro Gln Gln Lys Pro Arg Arg Asn
 50                  55                  60
Arg Lys Asn Lys Lys Gln Arg Gln Lys Lys Gln Ala Pro Gln Asn Asp
 65                  70                  75                  80
Pro Lys Gln Lys Lys Gln Pro Pro Gln Lys Lys Pro Ala Gln Lys Lys
                 85                  90                  95
Lys Lys Pro Gly Arg Arg Glu Arg Met Cys Met Lys Ile Glu Asn Asp
                100                 105                 110
Cys Ile Phe Glu Val Lys His Glu Gly Lys Val Met Gly Tyr Ala Cys
                115                 120                 125
Leu Val Gly Asp Lys Val Met Lys Pro Ala His Val Lys Gly Thr Ile
                130                 135                 140
Asp Asn Ala Asp Leu Ala Lys Leu Ala Phe Lys Arg Ser Ser Lys Tyr
145                 150                 155                 160
Asp Leu Glu Cys Ala Gln Ile Pro Val His Met Lys Ser Asp Ala Ser
                165                 170                 175
Lys Phe Thr His Glu Lys Pro Glu Gly Tyr Tyr Asn Trp His His Gly
                180                 185                 190
Ala Val Gln Tyr Ser Gly Gly Arg Phe Thr Ile Pro Thr Gly Ala Gly
                195                 200                 205
Lys Pro Gly Asp Ser Gly Arg Pro Ile Phe Asp Asn Lys Gly Arg Val
                210                 215                 220
Val Ala Ile Val Leu Gly Gly Ala Asn Glu Gly Ala Arg Thr Ala Leu
225                 230                 235                 240
Ser Val Val Thr Trp Asn Lys Asp Ile Val Thr Lys Ile Thr Pro Glu
                245                 250                 255
Gly Ala Glu Glu Trp Ser Leu Ala Leu Pro Val Leu Cys Leu Leu Ala
                260                 265                 270
Asn Thr Thr Phe Pro Cys Ser Gln Pro Pro Cys Thr Pro Cys Cys Tyr
                275                 280                 285
Glu Lys Glu Pro Glu Ser Thr Leu Arg Met Leu Glu Asp Asn Val Met
                290                 295                 300
Arg Pro Gly Tyr Tyr Gln Leu Leu Lys Ala Ser Leu Thr Cys Ser Pro
305                 310                 315                 320
His Arg Gln Arg Arg Ser Thr Lys Asp Asn Phe Asn Val Tyr Lys Ala
                325                 330                 335
Thr Arg Pro Tyr Leu Ala His Cys Pro Asp Cys Gly Glu Gly His Ser
                340                 345                 350
Cys His Ser Pro Ile Ala Leu Glu Arg Ile Arg Asn Glu Ala Thr Asp
                355                 360                 365
Gly Thr Leu Lys Ile Gln Val Ser Leu Gln Ile Gly Ile Lys Thr Asp
                370                 375                 380
Asp Ser His Asp Trp Thr Lys Leu Arg Tyr Met Asp Ser His Thr Pro
385                 390                 395                 400
```

-continued

```
Ala Asp Ala Glu Arg Ala Gly Leu Leu Val Arg Thr Ser Ala Pro Cys
                405                 410                 415
Thr Ile Thr Gly Thr Met Gly His Phe Ile Leu Ala Arg Cys Pro Lys
            420                 425                 430
Gly Glu Thr Leu Thr Val Gly Phe Thr Asp Ser Arg Lys Ile Ser His
            435                 440                 445
Thr Cys Thr His Pro Phe His His Glu Pro Val Ile Gly Arg Glu
        450                 455                 460
Arg Phe His Ser Arg Pro Gln His Gly Lys Glu Leu Pro Cys Ser Thr
465                 470                 475                 480
Tyr Val Gln Ser Thr Ala Ala Thr Ala Glu Glu Ile Glu Val His Met
                485                 490                 495
Pro Pro Asp Thr Pro Asp Arg Thr Leu Met Thr Gln Gln Ser Gly Asn
            500                 505                 510
Val Lys Ile Thr Val Asn Gly Gln Thr Val Arg Tyr Lys Cys Asn Cys
            515                 520                 525
Gly Gly Ser Asn Glu Gly Leu Thr Thr Thr Asp Lys Val Ile Asn Asn
            530                 535                 540
Cys Lys Ile Asp Gln Cys His Ala Ala Val Thr Asn His Lys Asn Trp
545                 550                 555                 560
Gln Tyr Asn Ser Pro Leu Val Pro Arg Asn Ala Glu Leu Gly Asp Arg
                565                 570                 575
Lys Gly Lys Ile His Ile Pro Phe Pro Leu Ala Asn Val Thr Cys Arg
            580                 585                 590
Val Pro Lys Ala Arg Asn Pro Thr Val Thr Tyr Gly Lys Asn Gln Val
            595                 600                 605
Thr Met Leu Leu Tyr Pro Asp His Pro Thr Leu Leu Ser Tyr Arg Asn
        610                 615                 620
Met Gly Gln Glu Pro Asn Tyr His Glu Glu Trp Val Thr His Lys Lys
625                 630                 635                 640
Glu Val Thr Leu Thr Val Pro Thr Glu Gly Leu Glu Val Thr Trp Gly
                645                 650                 655
Asn Asn Glu Pro Tyr Lys Tyr Trp Pro Gln Met Ser Thr Asn Gly Thr
            660                 665                 670
Ala His Gly His Pro His Glu Ile Ile Leu Tyr Tyr Tyr Glu Leu Tyr
            675                 680                 685
Pro Thr Met Thr Val Val Ile Val Ser Val Ala Ser Phe Val Leu Leu
        690                 695                 700
Ser Met Val Gly Thr Ala Val Gly Met Cys Val Cys Ala Arg Arg Arg
705                 710                 715                 720
Cys Ile Thr Pro Tyr Glu Leu Thr Pro Gly Ala Thr Val Pro Phe Leu
                725                 730                 735
Leu Ser Leu Leu Cys Cys Val Arg Thr Thr Lys Ala Ala Thr Tyr Tyr
            740                 745                 750
Glu Ala Ala Ala Tyr Leu Trp Asn Glu Gln Gln Pro Leu Phe Trp Leu
            755                 760                 765
Gln Ala Leu Ile Pro Leu Ala Ala Leu Ile Val Leu Cys Asn Cys Leu
        770                 775                 780
Lys Leu Leu Pro Cys Cys Cys Lys Thr Leu Ala Phe Leu Ala Val Met
785                 790                 795                 800
Ser Ile Gly Ala His Thr Val Ser Ala Tyr Glu His Val Thr Val Ile
                805                 810                 815
Pro Asn Thr Val Gly Val Pro Tyr Lys Thr Leu Val Asn Arg Pro Gly
```

```
                820                 825                 830
Tyr Ser Pro Met Val Leu Glu Met Glu Leu Gln Ser Val Thr Leu Glu
            835                 840                 845
Pro Thr Leu Ser Leu Asp Tyr Ile Thr Cys Glu Tyr Lys Thr Val Ile
850                 855                 860
Pro Ser Pro Tyr Val Lys Cys Cys Gly Thr Ala Glu Cys Lys Asp Lys
865                 870                 875                 880
Ser Leu Pro Asp Tyr Ser Cys Lys Val Phe Thr Gly Val Tyr Pro Phe
            885                 890                 895
Met Trp Gly Gly Ala Tyr Cys Phe Cys Asp Ala Glu Asn Thr Gln Leu
            900                 905                 910
Ser Glu Ala His Val Glu Lys Ser Glu Ser Cys Lys Thr Glu Phe Ala
            915                 920                 925
Ser Ala Tyr Arg Ala His Thr Ala Ser Ala Ser Ala Lys Leu Arg Val
            930                 935                 940
Leu Tyr Gln Gly Asn Asn Ile Thr Val Ala Ala Tyr Ala Asn Gly Asp
945                 950                 955                 960
His Ala Val Thr Val Lys Asp Ala Lys Phe Val Val Gly Pro Met Ser
            965                 970                 975
Ser Ala Trp Thr Pro Phe Asp Asn Lys Ile Val Val Tyr Lys Gly Asp
            980                 985                 990
Val Tyr Asn Met Asp Tyr Pro Pro Phe Gly Ala Gly Arg Pro Gly Gln
            995                 1000                1005
Phe Gly Asp Ile Gln Ser Arg Thr Pro Glu Ser Lys Asp Val Tyr
    1010                1015                1020
Ala Asn Thr Gln Leu Val Leu Gln Arg Pro Ala Ala Gly Thr Val
    1025                1030                1035
His Val Pro Tyr Ser Gln Ala Pro Ser Gly Phe Lys Tyr Trp Leu
    1040                1045                1050
Lys Glu Arg Gly Ala Ser Leu Gln His Thr Ala Pro Phe Gly Cys
    1055                1060                1065
Gln Ile Ala Thr Asn Pro Val Arg Ala Val Asn Cys Ala Val Gly
    1070                1075                1080
Asn Ile Pro Ile Ser Ile Asp Ile Pro Asp Ala Ala Phe Thr Arg
    1085                1090                1095
Val Val Asp Ala Pro Ser Val Thr Asp Met Ser Cys Glu Val Pro
    1100                1105                1110
Ala Cys Thr His Ser Ser Asp Phe Gly Gly Val Ala Ile Ile Lys
    1115                1120                1125
Tyr Thr Ala Ser Lys Lys Gly Lys Cys Ala Val His Ser Met Thr
    1130                1135                1140
Asn Ala Val Thr Ile Arg Glu Ala Asp Val Glu Val Glu Gly Asn
    1145                1150                1155
Ser Gln Leu Gln Ile Ser Phe Ser Thr Ala Leu Ala Ser Ala Glu
    1160                1165                1170
Phe Arg Val Gln Val Cys Ser Thr Gln Val His Cys Ala Ala Ala
    1175                1180                1185
Cys His Pro Pro Lys Asp His Ile Val Asn Tyr Pro Ala Ser His
    1190                1195                1200
Thr Thr Leu Gly Val Gln Asp Ile Ser Thr Thr Ala Met Ser Trp
    1205                1210                1215
Val Gln Lys Ile Thr Gly Gly Val Gly Leu Ile Val Ala Val Ala
    1220                1225                1230
```

Ala Leu Ile Leu Ile Val Val Leu Cys Val Ser Phe Ser Arg His
    1235                1240                1245

<210> SEQ ID NO 3
<211> LENGTH: 1255
<212> TYPE: PRT
<213> ORGANISM: Venesuelan equine encephalitis virus

<400> SEQUENCE: 3

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Ala
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Met Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
305                 310                 315                 320

Leu Leu Glu Ala Ala Val Lys Cys Pro Gly Arg Lys Arg Arg Ser Thr
                325                 330                 335

Glu Glu Leu Phe Asn Glu Tyr Lys Leu Thr Arg Pro Tyr Met Ala Arg
            340                 345                 350

Cys Ile Arg Cys Ala Val Gly Ser Cys His Ser Pro Ile Ala Ile Glu

```
                355                 360                 365
Ala Val Lys Ser Asp Gly His Asp Gly Tyr Val Arg Leu Gln Thr Ser
    370                 375                 380

Ser Gln Tyr Gly Leu Asp Ser Ser Gly Asn Leu Lys Gly Arg Thr Met
385                 390                 395                 400

Arg Tyr Asp Met His Gly Thr Ile Lys Glu Ile Pro Leu His Gln Val
                405                 410                 415

Ser Leu Tyr Thr Ser Arg Pro Cys His Ile Val Asp Gly His Gly Tyr
            420                 425                 430

Phe Leu Leu Ala Arg Cys Pro Ala Gly Asp Ser Ile Thr Met Glu Phe
        435                 440                 445

Lys Lys Asp Ser Val Arg His Ser Cys Ser Val Pro Tyr Glu Val Lys
    450                 455                 460

Phe Asn Pro Val Gly Arg Glu Leu Tyr Thr His Pro Pro Glu His Gly
465                 470                 475                 480

Val Glu Gln Ala Cys Gln Val Tyr Ala His Asp Ala Gln Asn Arg Gly
                485                 490                 495

Ala Tyr Val Glu Met His Leu Pro Gly Ser Glu Val Asp Ser Ser Leu
            500                 505                 510

Val Ser Leu Ser Gly Ser Ser Val Thr Val Thr Pro Pro Asp Gly Thr
        515                 520                 525

Ser Ala Leu Val Glu Cys Glu Cys Gly Gly Thr Lys Ile Ser Glu Thr
    530                 535                 540

Ile Asn Lys Thr Lys Gln Phe Ser Gln Cys Thr Lys Lys Glu Gln Cys
545                 550                 555                 560

Arg Ala Tyr Arg Leu Gln Asn Asp Lys Trp Val Tyr Asn Ser Asp Lys
                565                 570                 575

Leu Pro Lys Ala Ala Gly Ala Thr Leu Lys Gly Lys Leu His Val Pro
            580                 585                 590

Phe Leu Leu Ala Asp Gly Lys Cys Thr Val Pro Leu Ala Pro Glu Pro
        595                 600                 605

Met Ile Thr Phe Gly Phe Arg Ser Val Ser Leu Lys Leu His Pro Lys
    610                 615                 620

Asn Pro Thr Tyr Leu Ile Thr Arg Gln Leu Ala Asp Glu Pro His Tyr
625                 630                 635                 640

Thr His Glu Leu Ile Ser Glu Pro Ala Val Arg Asn Phe Thr Val Thr
                645                 650                 655

Glu Lys Gly Trp Glu Phe Val Trp Gly Asn His Pro Pro Lys Arg Phe
            660                 665                 670

Trp Ala Gln Glu Thr Ala Pro Gly Asn Pro His Gly Leu Pro His Glu
        675                 680                 685

Val Ile Thr His Tyr Tyr His Arg Tyr Pro Met Ser Thr Ile Leu Gly
    690                 695                 700

Leu Ser Ile Cys Ala Ala Ile Ala Thr Val Ser Val Ala Ala Ser Thr
705                 710                 715                 720

Trp Leu Phe Cys Arg Ser Arg Val Ala Cys Leu Thr Pro Tyr Arg Leu
                725                 730                 735

Thr Pro Asn Ala Arg Ile Pro Phe Cys Leu Ala Val Leu Cys Cys Ala
            740                 745                 750

Arg Thr Ala Arg Ala Glu Thr Thr Trp Glu Ser Leu Asp His Leu Trp
        755                 760                 765

Asn Asn Asn Gln Gln Met Phe Trp Ile Gln Leu Leu Ile Pro Leu Ala
    770                 775                 780
```

```
Ala Leu Ile Val Val Thr Arg Leu Leu Arg Cys Val Cys Cys Val Val
785                 790                 795                 800

Pro Phe Leu Val Met Ala Gly Ala Ala Gly Ala Tyr Glu His
                805                 810                 815

Ala Thr Thr Met Pro Ser Gln Ala Gly Ile Ser Tyr Asn Thr Ile Val
                820                 825                 830

Asn Arg Ala Gly Tyr Ala Pro Leu Pro Ile Ser Ile Thr Pro Thr Lys
            835                 840                 845

Ile Lys Leu Ile Pro Thr Val Asn Leu Glu Tyr Val Thr Cys His Tyr
850                 855                 860

Lys Thr Gly Met Asp Ser Pro Ala Ile Lys Cys Cys Gly Ser Gln Glu
865                 870                 875                 880

Cys Thr Pro Thr Tyr Arg Pro Asp Glu Gln Cys Lys Val Phe Thr Gly
                885                 890                 895

Val Tyr Pro Phe Met Trp Gly Gly Ala Tyr Cys Phe Cys Asp Thr Glu
                900                 905                 910

Asn Thr Gln Val Ser Lys Ala Tyr Val Met Lys Ser Asp Asp Cys Leu
            915                 920                 925

Ala Asp His Ala Glu Ala Tyr Lys Ala His Thr Ala Ser Val Gln Ala
930                 935                 940

Phe Leu Asn Ile Thr Val Gly Glu His Ser Ile Val Thr Thr Val Tyr
945                 950                 955                 960

Val Asn Gly Glu Thr Pro Val Asn Phe Asn Gly Val Lys Ile Thr Ala
                965                 970                 975

Gly Pro Leu Ser Thr Ala Trp Thr Pro Phe Asp Arg Lys Ile Val Gln
                980                 985                 990

Tyr Ala Gly Glu Ile Tyr Asn Tyr  Asp Phe Pro Glu Tyr  Gly Ala Gly
            995                 1000                1005

Gln Pro  Gly Ala Phe Gly Asp  Ile Gln Ser Arg Thr  Val Ser Ser
    1010                 1015                 1020

Ser Asp  Leu Tyr Ala Asn Thr  Asn Leu Val Leu Gln  Arg Pro Lys
    1025                 1030                 1035

Ala Gly  Ala Ile His Val Pro  Tyr Thr Gln Ala Pro  Ser Gly Phe
    1040                 1045                 1050

Glu Gln  Trp Lys Lys Asp Lys  Ala Pro Ser Leu Lys  Phe Thr Ala
    1055                 1060                 1065

Pro Phe  Gly Cys Glu Ile Tyr  Thr Asn Pro Ile Arg  Ala Glu Asn
    1070                 1075                 1080

Cys Ala  Val Gly Ser Ile Pro  Leu Ala Phe Asp Ile  Pro Asp Ala
    1085                 1090                 1095

Leu Phe  Thr Arg Val Ser Glu  Thr Pro Thr Leu Ser  Ala Ala Glu
    1100                 1105                 1110

Cys Thr  Leu Asn Glu Cys Val  Tyr Ser Ser Asp Phe  Gly Gly Ile
    1115                 1120                 1125

Ala Thr  Val Lys Tyr Ser Ala  Ser Lys Ser Gly Lys  Cys Ala Val
    1130                 1135                 1140

His Val  Pro Ser Gly Thr Ala  Thr Leu Lys Glu Ala  Ala Val Glu
    1145                 1150                 1155

Leu Thr  Glu Gln Gly Ser Ala  Thr Ile His Phe Ser  Thr Ala Asn
    1160                 1165                 1170

Ile His  Pro Glu Phe Arg Leu  Gln Ile Cys Thr Ser  Tyr Val Thr
    1175                 1180                 1185
```

```
Cys Lys Gly Asp Cys His Pro Pro Lys Asp His Ile Val Thr His
    1190                1195                1200

Pro Gln Tyr His Ala Gln Thr Phe Thr Ala Ala Val Ser Lys Thr
    1205                1210                1215

Ala Trp Thr Trp Leu Thr Ser Leu Leu Gly Gly Ser Ala Val Ile
    1220                1225                1230

Ile Ile Ile Gly Leu Val Leu Ala Thr Ile Val Ala Met Tyr Val
    1235                1240                1245

Leu Thr Asn Gln Lys His Asn
    1250                1255

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Leu Asn Trp Tyr Arg Met Ser Pro Ser Asn Gln Thr Asp Lys Leu Ala
1               5                   10                  15

Ala Phe

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Met Leu Asn Trp Tyr Arg Met Ser Pro Ser Asn Gln Thr Asp Lys Leu
1               5                   10                  15

Ala Ala Phe Ser
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Val Leu Asn Trp Tyr Arg Met Ser Pro Ser Asn Gln Thr Asp Lys Leu
1               5                   10                  15

Ala Ala Phe Pro
            20

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide

<400> SEQUENCE: 7

Gly Ala Ile Ser Leu His Pro Lys Ala Lys Ile Glu Glu Ser
1               5                   10

<210> SEQ ID NO 8
<211> LENGTH: 15
<212> TYPE: PRT
```

<213> ORGANISM: Artificial Sequence
<220> FEATURE:
<223> OTHER INFORMATION: Synthetic peptide

<400> SEQUENCE: 8

Cys Gly Ala Ile Ser Leu His Pro Lys Ala Lys Ile Glu Glu Cys
1               5                   10                  15

<210> SEQ ID NO 9
<211> LENGTH: 19
<212> TYPE: PRT
<213> ORGANISM: Artificial Sequence
<220> FEATURE:
<223> OTHER INFORMATION: Synthetic peptide

<400> SEQUENCE: 9

Val Leu Asn Trp Tyr Arg Met Ser Pro Ser Asn Gln Thr Asp Lys Leu
1               5                   10                  15

Ala Ala Phe

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide

<400> SEQUENCE: 10

Gly Ala Ile Ser Leu Ala Pro Lys Ala Gln Ile Lys Glu Ser
1               5                   10

<210> SEQ ID NO 11
<211> LENGTH: 31
<212> TYPE: PRT
<213> ORGANISM: Artificial Sequence
<220> FEATURE:
<223> OTHER INFORMATION: Synthetic peptide

<400> SEQUENCE: 11

Arg Asn Asp Ser Gly Thr Tyr Leu Cys Gly Ala Ile Ser Leu Ala Pro
1               5                   10                  15

Lys Ala Gln Ile Lys Glu Ser Leu Arg Ala Glu Leu Arg Val Thr
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic peptide

<400> SEQUENCE: 12

Arg Asn Asp Ser Gly Ile Tyr Leu Cys Gly Ala Ile Ser Leu His Pro
1               5                   10                  15

Lys Ala Lys Ile Glu Glu Ser Pro Gly Ala Glu Leu Val Val Thr
            20                  25                  30

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

```
Cys Ile Ile Ser Tyr Gly Gly Ala Asp Tyr Cys
1               5                   10
```

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

```
Cys Met Ile Ser Tyr Gly Gly Ala Asp Tyr Cys
1               5                   10
```

<210> SEQ ID NO 15
<211> LENGTH: 26
<212> TYPE: PRT
<213> ORGANISM: Artificial Sequence
<220> FEATURE:
<223> OTHER INFORMATION: Synthetic peptide

<400> SEQUENCE: 15

```
Leu Gln Asp Ala Gly Val Tyr Arg Cys Met Ile Ser Tyr Gly Gly Ala
1               5                   10                  15

Asp Tyr Lys Arg Ile Thr Val Lys Val Asn
            20                  25
```

<210> SEQ ID NO 16
<211> LENGTH: 26
<212> TYPE: PRT
<213> ORGANISM: Artificial Sequence
<220> FEATURE:
<223> OTHER INFORMATION: Synthetic peptide

<400> SEQUENCE: 16

```
Leu Gln Asp Ala Gly Val Tyr Arg Ala Met Ile Ser Tyr Gly Gly Ala
1               5                   10                  15

Asp Tyr Lys Arg Ile Thr Val Lys Val Asn
            20                  25
```

<210> SEQ ID NO 17
<211> LENGTH: 21
<212> TYPE: PRT
<213> ORGANISM: Artificial Sequence
<220> FEATURE:
<223> OTHER INFORMATION: Synthetic peptide

<400> SEQUENCE: 17

```
Asp Leu Ala Ala Leu Ile Val Tyr Trp Glu Met Glu Asp Lys Asn Ile
1               5                   10                  15

Ile Gln Phe Val His
            20
```

<210> SEQ ID NO 18
<211> LENGTH: 23
<212> TYPE: PRT
<213> ORGANISM: Artificial Sequence
<220> FEATURE:
<223> OTHER INFORMATION: Synthetic peptide

<400> SEQUENCE: 18

```
Asp Leu Ala Ala Leu Ile Val Tyr Trp Glu Met Glu Asp Lys Asn Ile
1               5                   10                  15

Ile Gln Phe Val His Gly Gly
            20
```

```
<210> SEQ ID NO 19
<211> LENGTH: 27
<212> TYPE: PRT
<213> ORGANISM: Artificial Sequence
<220> FEATURE:
<223> OTHER INFORMATION: Synthetic peptide

<400> SEQUENCE: 19

Phe Thr Val Thr Val Pro Lys Asp Leu Tyr Val Val Glu Tyr Gly Ser
1               5                   10                  15

Asn Met Thr Ile Glu Cys Lys Phe Pro Val Glu
            20                  25

<210> SEQ ID NO 20
<211> LENGTH: 26
<212> TYPE: PRT
<213> ORGANISM: Artificial Sequence
<220> FEATURE:
<223> OTHER INFORMATION: Synthetic peptide

<400> SEQUENCE: 20

Leu Gln Asp Ala Gly Val Tyr Cys Cys Ile Ile Ser Tyr Gly Gly Ala
1               5                   10                  15

Asp Tyr Lys Arg Ile Thr Leu Lys Val Asn
            20                  25

<210> SEQ ID NO 21
<211> LENGTH: 26
<212> TYPE: PRT
<213> ORGANISM: Artificial Sequence
<220> FEATURE:
<223> OTHER INFORMATION: Synthetic peptide

<400> SEQUENCE: 21

Leu Gln Asp Ala Gly Val Tyr Ala Ala Ile Ile Ser Tyr Gly Gly Ala
1               5                   10                  15

Asp Tyr Lys Arg Ile Thr Leu Lys Val Asn
            20                  25

<210> SEQ ID NO 22
<211> LENGTH: 21
<212> TYPE: PRT
<213> ORGANISM: Artificial Sequence
<220> FEATURE:
<223> OTHER INFORMATION: Synthetic peptide

<400> SEQUENCE: 22

Asp Leu Leu Ala Leu Val Val Tyr Trp Glu Lys Glu Asp Glu Gln Val
1               5                   10                  15

Ile Gln Phe Val Ala
            20

<210> SEQ ID NO 23
<211> LENGTH: 23
<212> TYPE: PRT
<213> ORGANISM: Artificial Sequence
<220> FEATURE:
<223> OTHER INFORMATION: Synthetic peptide

<400> SEQUENCE: 23

Asp Leu Leu Ala Leu Val Val Tyr Trp Glu Lys Glu Asp Glu Gln Val
1               5                   10                  15

Ile Gln Phe Val Ala Gly Gly
```

<210> SEQ ID NO 24
<211> LENGTH: 27
<212> TYPE: PRT
<213> ORGANISM: Artificial Sequence
<220> FEATURE:
<223> OTHER INFORMATION: Synthetic peptide

<400> SEQUENCE: 24

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu
            20                  25

<210> SEQ ID NO 25
<211> LENGTH: 8410
<212> TYPE: DNA
<213> ORGANISM: Artificial Sequence
<220> FEATURE:
<223> OTHER INFORMATION: Synthetic polynucleotide

<400> SEQUENCE: 25

| | | | | | |
|---|---|---|---|---|---|
| gaattcccat | tgcatacgtt | gtatccatat | cataatatgt | acatttatat | tggctcatgt | 60 |
| ccaacattac | cgccatgttg | acattgatta | ttgactagtt | attaatagta | atcaattacg | 120 |
| gggtcattag | ttcatagccc | atatatggag | ttccgcgtta | cataacttac | ggtaaatggc | 180 |
| ccgcctggct | gaccgcccaa | cgacccccgc | ccattgacgt | caataatgac | gtatgttccc | 240 |
| atagtaacgc | caatagggac | tttccattga | cgtcaatggg | tggagtattt | acggtaaact | 300 |
| gcccacttgg | cagtacatca | agtgtatcat | atgccaagta | cgccccctat | tgacgtcaat | 360 |
| gacggtaaat | ggcccgcctg | gcattatgcc | cagtacatga | ccttatggga | ctttcctact | 420 |
| tggcagtaca | tctacgtatt | agtcatcgct | attaccatgg | tgatgcggtt | ttggcagtac | 480 |
| atcaatgggc | gtggatagcg | gtttgactca | cggggatttc | caagtctcca | ccccattgac | 540 |
| gtcaatggga | gtttgttttg | gcaccaaaat | caacgggact | ttccaaaatg | tcgtaacaac | 600 |
| tccgccccat | tgacgcaaat | gggcggtagg | cgtgtacggt | gggaggtcta | tataagcaga | 660 |
| gctcgtttag | tgaaccgtca | gatcgcctgg | agacgccatc | cacgctgttt | tgacctccat | 720 |
| agaagacacc | gggaccgatc | cagcctccgt | taacggtgga | gggcagtgta | gtctgagcag | 780 |
| tactcgttgc | tgccgcgcgc | gccaccagac | ataatagctg | acagactaac | agactgttcc | 840 |
| tttccatggg | tcttttctgc | agtcaccgtc | gtcgacacgt | gtgatcagat | atcgcggccg | 900 |
| ccaccatgga | gttcatcccg | acgcaaactt | tctataacag | aaggtaccaa | ccccgaccct | 960 |
| gggccccacg | ccctacaatt | caagtaatta | gacctagacc | acgtccacag | aggcaggctg | 1020 |
| ggcaactcgc | ccagctgatc | tccgcagtca | acaaattgac | catgcgcgcg | gtacctcaac | 1080 |
| agaagcctcg | cagaaatcgg | aaaaacaaga | agcaaaggca | gaagaagcag | gcgccgcaaa | 1140 |
| acgacccaaa | gcaaaagaag | caaccaccac | aaaagaagcc | ggctcaaaag | aagaagaaac | 1200 |
| caggccgtag | ggagagaatg | tgcatgaaaa | ttgaaaatga | ttgcatcttc | gaagtcaagc | 1260 |
| atgaaggcaa | agtgatgggc | tacgcatgcc | tggtggggga | taaagtaatg | aaaccagcac | 1320 |
| atgtgaaggg | aactatcgac | aatgccgatc | tggctaaact | ggcctttaag | cggtcgtcta | 1380 |
| aatacgatct | tgaatgtgca | cagataccgg | tgcacatgaa | gtctgatgcc | tcgaagttta | 1440 |
| cccacgagaa | acccgagggg | tactataact | ggcatcacgg | agcagtgcag | tattcaggag | 1500 |
| gccggttcac | tatcccgacg | ggtgcaggca | agccgggaga | cagcggcaga | ccgatcttcg | 1560 |

```
acaacaaagg acgggtggtg gccatcgtcc taggaggggc caacgaaggt gcccgcacgg    1620
ccctctccgt ggtgacgtgg aacaaagaca tcgtcacaaa attacccct gagggagccg     1680 aagagtggag cctcgccctc ccggtcttgt gcctgttggc aaacactaca ttcccctgct    1740
ctcagccgcc ttgcacaccc tgctgctacg aaaaggaacc ggaaagcacc ttgcgcatgc    1800
ttgaggacaa cgtgatgaga cccggatact accagctact aaaagcatcg ctgacttgct    1860
ctccccaccg ccaaagacgc agtactaagg acaattttaa tgtctataaa gccacaagac    1920
catatctagc tcattgtcct gactgcggag aagggcattc gtgccacagc cctatcgcat    1980
tggagcgcat cagaaatgaa gcaacggacg gaacgctgaa aatccaggtc tctttgcaga    2040
tcgggataaa gacagatgac agccacgatt ggaccaagct gcgctatatg gatagccata    2100
cgccagcgga cgcggagcga gccggattgc ttgtaaggac ttcagcaccg tgcacgatca    2160
ccgggaccat gggacacttt attctcgccc gatgcccgaa aggagagacg ctgacagtgg    2220
gatttacgga cagcagaaag atcagccaca catgcacaca cccgttccat catgaaccac    2280
ctgtgatagg taggagagg ttccactctc gaccacaaca tggtaaagag ttaccttgca     2340
gcacgtacgt gcagagcacc gctgccactg ctgaggagat agaggtgcat atgcccccag    2400
atactcctga ccgcacgctg atgacgcagc agtctggcaa cgtgaagatc acagttaatg    2460
ggcagacggt gcggtacaag tgcaactgcg gtggctccgg aagtggatcc aacgagggac    2520
tgacaaccac agacaaagtg atcaataact gcaaaattga tcagtgccat gctgcagtca    2580
ctaatcacaa gaattggcaa tacaactccc ctttagtccc cgcaacgct gaactcgggg      2640 accgtaaagg aaagatccac atcccattcc cattggcaaa cgtgacttgc agagtgccaa    2700
aagcaagaaa ccctacagta acttacggaa aaaccaagt caccatgctg ctgtatcctg      2760
accatccgac actcttgtct taccgtaaca tgggacagga accaaattac cacgaggagt    2820
gggtgacaca caagaaggag gttaccttga ccgtgcctac tgagggtctg gaggtcactt    2880
ggggcaacaa cgaaccatac aagtactggc cgcagatgtc tacgaacggt actgctcatg    2940
gtcacccaca tgagataatc ttgtactatt atgagctgta ccccactatg actgtagtca    3000
ttgtgtcggt ggcctcgttc gtgcttctgt cgatggtggg cacagcagtg ggaatgtgtg    3060
tgtgcgcacg cgcagatgc attacaccat atgaattaac accaggagcc actgttccct     3120
tcctgctcag cctgctatgc tgcgtcagaa cgaccaaggc ggccacatat tacgaggctg    3180
cggcatatct atggaacgaa cagcagcccc tgttctggtt gcaggctctt atcccgctgg    3240
ccgccttgat cgtcctgtgc aactgtctga aactcttgcc atgctgctgt aagaccctgg    3300
cttttttagc cgtaatgagc atcggtgccc acactgtgag cgcgtacgaa cacgtaacag    3360
tgatcccgaa cacggtggga gtaccgtata agactcttgt caacagaccg ggttacagcc    3420
ccatggtgtt ggagatggag ctacaatcag tcaccttgga accaacactg tcacttgact    3480
acatcacgtg cgagtacaaa actgtcatcc cctccccgta cgtgaagtgc tgtggtacag    3540
cagagtgcaa ggacaagagc ctaccagact acagctgcaa ggtctttact ggagtctacc    3600
catttatgtg gggcggcgcc tactgctttt gcgacgccga aaatacgcaa ttgagcgagg    3660
cacatgtaga gaaatctgaa tcttgcaaaa cagagtttgc atcggcctac agagcccaca    3720
ccgcatcggc gtcggcgaag ctccgcgtcc tttaccaagg aaacaacatt accgtagctg    3780
cctacgctaa cggtgaccat gccgtcacag taaaggacgc caagtttgtc gtgggcccaa    3840
tgtcctccgc ctggacacct tttgacaaca aaatcgtggt gtacaaaggc gacgtctaca    3900
```

-continued

```
acatggacta cccacctttt ggcgcaggaa gaccaggaca atttggtgac attcaaagtc    3960
gtacaccgga aagtaaagac gtttatgcca acactcagtt ggtactacag aggccagcag    4020
caggcacggt acatgtacca tactctcagg caccatctgg cttcaagtat tggctgaagg    4080
aacgaggagc atcgctacag cacacggcac cgttcggttg ccagattgcg acaaacccgg    4140
taagagctgt aaattgcgct gtggggaaca taccaatttc catcgacata ccggatgcgg    4200
cctttactag ggttgtcgat gcaccctctg taacggacat gtcatgcgaa gtaccagcct    4260
gcactcactc ctccgacttt gggggcgtcg ccatcatcaa atacacagct agcaagaaag    4320
gtaaatgtgc agtacattcg atgaccaacg ccgttaccat tcgagaagcc gacgtagaag    4380
tagaggggaa ctcccagctg caaatatcct tctcaacagc cctggcaagc gccgagtttc    4440
gcgtgcaagt gtgctccaca caagtacact gcgcagccgc atgccaccct caaaggacc     4500 acatagtcaa ttacccagca tcacacacca cccttggggt ccaggatata tccacaacgg    4560
caatgtcttg ggtgcagaag attacgggag gagtaggatt aattgttgct gttgctgcct    4620
taattttaat tgtggtgcta tgcgtgtcgt ttagcaggca ctaaggatct agatctgctg    4680
tgccttctag ttgccagcca tctgttgttt gcccctcccc cgtgccttcc ttgaccctgg    4740
aaggtgccac tcccactgtc ctttcctaat aaaatgagga aattgcatcg cattgtctga    4800
gtaggtgtca ttctattctg gggggtgggg tggggcagga cagcaagggg gaggattggg    4860
aagacaatag caggcatgct ggggatgcgg tgggctctat gggtacccag gtgctgaaga    4920
attgacccgg ttcctcctgg gccagaaaga agcaggcaca tcccttctc tgtgacacac     4980 cctgtccacg cccctggttc ttagttccag ccccactcat aggacactca tagctcagga    5040
gggctccgcc ttcaatccca cccgctaaag tacttggagc ggtctctccc tccctcatca    5100
gcccaccaaa ccaaacctag cctccaagag tgggaagaaa ttaaagcaag ataggctatt    5160
aagtgcagag ggagagaaaa tgcctccaac atgtgaggaa gtaatgagag aaatcataga    5220 atttaaggc catgatttaa ggccatcatg gcctaagctt gaaaggagat aggatccaag     5280
cttggcgtaa tcatggtcat agctgtttcc tgtgtgaaat tgttatccgc tcacaattcc    5340
acacaacata cgagccggaa gcataaagtg taaagcctgg ggtgcctaat gagtgagcta    5400
actcacatta attgcgttgc gctcactgcc cgctttccag tcgggaaacc tgtcgtgcca    5460
gctgcattaa tgaatcggcc aacgcgcggg gagaggcggt ttgcgtattg ggcgctcttc    5520
cgcttcctcg ctcactgact cgctgcgctc ggtcgttcgg ctgcggcgag cggtatcagc    5580
tcactcaaag gcggtaatac ggttatccac agaatcaggg gataacgcag gaaagaacat    5640
gtgagcaaaa ggccagcaaa aggccaggaa ccgtaaaaag gccgcgttgc tggcgttttt    5700
ccataggctc cgcccccctg acgagcatca caaaaatcga cgctcaagtc agaggtggcg    5760
aaacccgaca ggactataaa gataccaggc gtttccccct ggaagctccc tcgtgcgctc    5820
tcctgttccg accctgccgc ttaccggata cctgtccgcc tttctccctt cgggaagcgt    5880
ggcgctttct catagctcac gctgtaggta tctcagttcg gtgtaggtcg ttcgctccaa    5940
gctgggctgt gtgcacgaac cccccgttca gcccgaccgc tgcgccttat ccggtaacta    6000
tcgtcttgag tccaacccgg taagacacga cttatcgcca ctggcagcag ccactggtaa    6060
caggattagc agagcgaggt atgtaggcgg tgctacagag ttcttgaagt ggtggcctaa    6120
ctacggctac actagaagaa cagtatttgg tatctgcgct ctgctgaagc cagttacctt    6180
cggaaaaaga gttggtagct cttgatccgg caaacaaacc accgctggta gcggtggttt    6240
ttttgtttgc aagcagcaga ttacgcgcag aaaaaaagga tctcaagaag atcctttgat    6300
```

```
cttttctacg gggtctgacg ctcagtggaa cgaaaactca cgttaaggga ttttggtcat    6360
gagattatca aaaggatctt caccctagat ccttttaaat taaaaatgaa gttttaaatc    6420
aatctaaagt atatatgagt aaacttggtc tgacagttac caatgcttaa tcagtgaggc    6480
acctatctca gcgatctgtc tatttcgttc atccatagtt gcctgactcc ccgtcgtgta    6540
gataactacg atacgggagg gcttaccatc tggccccagt gctgcaatga taccgcgaga    6600
accacgctca ccggctccag atttatcagc aataaaccag ccagccggaa gggccgagcg    6660
cagaagtggt cctgcaactt tatccgcctc catccagtct attaattgtt gccgggaagc    6720
tagagtaagt agttcgccag ttaatagttt gcgcaacgtt gttgccattg ctacaggcat    6780
cgtggtgtca cgctcgtcgt ttggtatggc ttcattcagc tccggttccc aacgatcaag    6840
gcgagttaca tgatccccca tgttgtgcaa aaaagcggtt agctccttcg gtcctccgat    6900
cgttgtcaga agtaagttgg ccgcagtgtt atcactcatg gttatggcag cactgcataa    6960
ttctcttact gtcatgccat ccgtaagatg cttttctgtg actggtgagt actcaaccaa    7020
gtcattctga gaatagtgta tgcggcgacc gagttgctct tgcccggcgt caatacggga    7080
taataccgcg ccacatagca gaactttaaa agtgctcatc attggaaaac gttcttcggg    7140
gcgaaaactc tcaaggatct taccgctgtt gagatccagt tcgatgtaac ccactcgtgc    7200
acccaactga tcttcagcat cttttacttt caccagcgtt tctgggtgag caaaaacagg    7260
aaggcaaaat gccgcaaaaa agggaataag ggcgacacgg aaatgttgaa tactcatact    7320
cttcctttt caatattatt gaagcattta tcagggttat tgtctcatga gcggatacat    7380
atttgaatgt atttagaaaa ataaacaaat aggggttccg cgcacatttc cccgaaaagt    7440
gccacctgac gtctaagaaa ccattattat catgacatta acctataaaa ataggcgtat    7500
cacgaggccc tttcgggtcg cgcgtttcgg tgatgacggt gaaaacctct gacacatgca    7560
gctcccgttg acggtcacag cttgtctgta agcggatgcc gggagcagac aagcccgtca    7620
gggcgcgtca gcgggtgttg gcgggtgtcg ggctggctt aactatgcgg catcagagca    7680
gattgtactg agagtgcacc ataaaattgt aaacgttaat attttgttaa aattcgcgtt    7740
aaatttttgt taaatcagct cattttttaa ccaataggcc gaaatcggca aaatccctta    7800
taaatcaaaa gaatagcccg agatagggtt gagtgttgtt ccagtttgga acaagagtcc    7860
actattaaag aacgtggact ccaacgtcaa agggcgaaaa accgtctatc agggcgatgg    7920
cccactacgt gaaccatcac ccaaatcaag ttttttgggg tcgaggtgcc gtaaagcact    7980
aaatcggaac cctaaaggga gcccccgatt tagagcttga cggggaaagc cggcgaacgt    8040
ggcgagaaag gaagggaaga aagcgaaagg agcgggcgct agggcgctgg caagtgtagc    8100
ggtcacgctg cgcgtaacca ccacacccgc cgcgcttaat gcgccgctac agggcgcgta    8160
ctatggttgc tttgacgtat gcggtgtgaa ataccgcaca gatgcgtaag gagaaaatac    8220
cgcatcaggc gccattcgcc attcaggctg cgcaactgtt gggaagggcg atcggtgcgg    8280
gcctcttcgc tattacgcca gctggcgaaa ggggatgtg ctgcaaggcg attaagttgg    8340
gtaacgccag ggttttccca gtcacgacgt tgtaaaacga cggccagtga attccatggt    8400
ctcaactttc                                                           8410
```

<210> SEQ ID NO 26
<211> LENGTH: 8431
<212> TYPE: DNA
<213> ORGANISM: Artificial Sequence
<220> FEATURE:

<223> OTHER INFORMATION: Synthetic polynucleotide

<400> SEQUENCE: 26

```
gaattcccat tgcatacgtt gtatccatat cataatatgt acatttatat tggctcatgt        60
ccaacattac cgccatgttg acattgatta ttgactagtt attaatagta atcaattacg       120
gggtcattag ttcatagccc atatatggag ttccgcgtta cataacttac ggtaaatggc       180
ccgcctggct gaccgcccaa cgaccccgc ccattgacgt caataatgac gtatgttccc       240
atagtaacgc caatagggac tttccattga cgtcaatggg tggagtattt acggtaaact       300
gcccacttgg cagtacatca agtgtatcat atgccaagta cgccccctat tgacgtcaat       360
gacggtaaat ggcccgcctg gcattatgcc cagtacatga ccttatggga ctttcctact       420
tggcagtaca tctacgtatt agtcatcgct attaccatgg tgatgcggtt ttggcagtac       480
atcaatgggc gtggatagcg gtttgactca cggggatttc caagtctcca ccccattgac       540
gtcaatggga gtttgttttg gcaccaaaat caacgggact ttccaaaatg tcgtaacaac       600
tccgccccat tgacgcaaat gggcggtagg cgtgtacggt gggaggtcta tataagcaga       660
gctcgtttag tgaaccgtca gatcgcctgg agacgccatc cacgctgttt tgacctccat       720
agaagacacc gggaccgatc cagcctccgt aacggtgga gggcagtgta gtctgagcag       780
tactcgttgc tgccgcgcgc gccaccagac ataatagctg acagactaac agactgttcc       840
tttccatggg tcttttctgc agtcaccgtc gtcgacacgt gtgatcagat atcgcggccg       900
ccaccatgtt cccgttccag ccaatgtatc cgatgcagcc aatgccctat cgcaacccgt       960
tcgcggcccc gcgcaggccc tggttcccca gaaccgaccc ttttctggcg atgcaggtgc      1020
aggaattaac ccgctcgatg gctaacctga cgttcaagca acgccgggac gcgccacctg      1080
aggggccatc cgctaataaa ccgaagaagg aggcctcgca aaaacagaaa gggggaggcc      1140
aagggaagaa gaagaagaac caagggaaga agaaggctaa gacagggccg cctaatccga      1200
aggcacagaa tggaaacaag aagaagacca acaagaaacc aggcaagaga cagcgcatgg      1260
tcatgaaatt ggaatctgac aagacgttcc caatcatgtt ggaagggaag ataaacggct      1320
acgcttgtgt ggtcggaggg aagttattca ggccgatgca tgtggaaggc aagatcgaca      1380
acgacgttct ggccgcgctt aagacgaaga agcatccaa atacgatctt gagtatgcag      1440
atgtgccaca gaacatgcgg gccgatacat tcaaatacac ccatgagaaa ccccaaggct      1500
attacagctg gcatcatgga gcagtccaat atgaaaatgg gcgtttcacg gtgccgaaag      1560
gagttggggc aagggagac agcggacgac ccattctgga taaccaggga cgggtggtcg      1620
ctattgtgct gggaggtgtg aatgaaggat ctaggacagc cctttcagtc gtcatgtgga      1680
acgagaaggg agttaccgtg aagtatactc cagagaactg cgagcaatgg tcactagtga      1740
ccaccatgtg tctgctcgcc aatgtgacgt tcccatgtgc tcaaccacca atttgctacg      1800
acagaaaacc agcagagact ttggccatgc tcagcgttaa cgttgacaac ccgggctacg      1860
atgagctgct ggaagcagct gttaagtgcc ccggaaggaa aaggagatcc accgaggagc      1920
tgtttaatga gtataagcta acgcgcctt acatggccag atgcatcaga tgtgcagttg      1980
ggagctgcca tagtccaata gcaatcgagg cagtaaagag cgacgggcac gacggttatg      2040
ttagacttca gacttcctcg cagtatggcc tggattcctc cggcaactta aagggcagga      2100
ccatgcggta tgcatgcac gggaccatta aagagatacc actacatcaa gtgtcactct      2160
atacatctcg cccgtgtcac attgtggatg ggcacggtta tttcctgctt ccaggtgcc      2220
cggcagggga ctccatcacc atggaattta agaaagattc cgtcagacac tcctgctcgg      2280
```

```
tgccgtatga agtgaaattt aatcctgtag gcagagaact ctatactcat cccccagaac    2340
acggagtaga gcaagcgtgc caagtctacg cacatgatgc acagaacaga ggagcttatg    2400
tcgagatgca cctcccgggc tcagaagtgg acagcagttt ggtttccttg agcggctccg    2460
gaggatccag ttcagtcacc gtgacacctc ctgatgggac tagcgccctg gtggaatgcg    2520
agtgtggcgg cacaaagatc tccgagacca tcaacaagac aaaacagttc agccagtgca    2580
caaagaagga gcagtgcaga gcatatcggc tgcagaacga taagtgggtg tataattctg    2640
acaaactgcc caaagcagcg ggagccacct aaaaggaaa actgcatgtc ccattcttgc      2700
tggcagacgg caaatgcacc gtgcctctag caccagaacc tatgataacc ttcggtttca    2760
gatcagtgtc actgaaactg caccctaaga atcccacata tctaatcacc cgccaacttg    2820
ctgatgagcc tcactacacg cacgagctca tatctgaacc agctgttagg aattttaccg    2880
tcaccgaaaa agggtgggag tttgtatggg gaaaccaccc gccgaaaagg ttttgggcac    2940
aggaaacagc acccggaaat ccacatgggc taccgcacga ggtgataact cattattacc    3000
acagataccc tatgtccacc atcctgggtt tgtcaatttg tgccgccatt gcaaccgttt    3060
ccgttgcagc gtctacctgg ctgttttgca gatcaagagt tgcgtgccta actccttacc    3120
ggctaacacc taacgctagg ataccatttt gtctggctgt gctttgctgc gcccgcactg    3180
cccgggccga gaccacctgg gagtccttgg atcacctatg gaacaataac caacagatgt    3240
tctggattca attgctgatc cctctggccg ccttgatcgt agtgactcgc ctgctcaggt    3300
gcgtgtgctg tgtcgtgcct ttttttagtca tggccggcgc cgcaggcgcc ggcgcctacg    3360
agcacgcgac cacgatgccg agccaagcgg gaatctcgta taacactata gtcaacagag    3420
caggctacgc accactccct atcagcataa caccaacaaa gatcaagctg atacctacag    3480
tgaacttgga gtacgtcacc tgccactaca aaacaggaat ggattcacca gccatcaaat    3540
gctgcggatc tcaggaatgc actccaactt acaggcctga tgaacagtgc aaagtcttca    3600
caggggttta cccgttcatg tggggtggtg catattgctt ttgcgacact gagaacaccc    3660
aagtcagcaa ggcctacgta atgaaatctg acgactgcct tgcggatcat gctgaagcat    3720
ataaagcgca cacagcctca gtgcaggcgt tcctcaacat cacagtggga gaacactcta    3780
ttgtgactac cgtgtatgtg aatggagaaa ctcctgtgaa tttcaatggg gtcaaaataa    3840
ctgcaggtcc gctttccaca gcttggacac cctttgatcg caaaatcgtg cagtatgccg    3900
gggagatcta taattatgat tttcctgagt atggggcagg acaaccagga gcatttggag    3960
atatacaatc cagaacagtc tcaagctctg atctgtatgc caataccaac ctagtgctgc    4020
agagacccaa gcaggagcg atccacgtgc catacactca ggcaccttcg ggttttgagc    4080 aatgaagaa agataaagct ccatcattga aatttaccgc cccttccgga tgcgaaatat    4140
atacaaaccc cattcgcgcc gaaaactgtg ctgtagggtc aattccatta gcctttgaca    4200
ttcccgacgc cttgttcacc agggtgtcag aaacaccgac actttcagcg gccgaatgca    4260
ctcttaacga gtgcgtgtat tcttccgact ttggtgggat cgccacggtc aagtactcgg    4320
ccagcaagtc aggcaagtgc gcagtccatg tgccatcagg gactgctacc ctaaaagaag    4380
cagcagtcga gctaaccgag caagggtcgg cgactatcca tttctcgacc gcaaatatcc    4440
acccggagtt caggctccaa atatgcacat catatgttac gtgcaaaggt gattgtcacc    4500
ccccgaaaga ccatattgtg acacaccctc agtatcacgc ccaaacattt acagccgcgg    4560
tgtcaaaaac cgcgtggacg tggttaacat ccctgctggg aggatcagcc gtaattatta    4620
```

```
taattggctt ggtgctggct actattgtgg ccatgtacgt gctgaccaac cagaaacata    4680
attaaggatc tagatctgct gtgccttcta gttgccagcc atctgttgtt tgcccctccc    4740
ccgtgccttc cttgaccctg aaggtgcca ctcccactgt cctttcctaa taaaatgagg    4800
aaattgcatc gcattgtctg agtaggtgtc attctattct gggggtggg gtggggcagg    4860 acagcaaggg ggaggattgg aagacaata gcaggcatgc tggggatgcg gtgggctcta    4920
tgggtaccca ggtgctgaag aattgacccg gttcctcctg gccagaaag aagcaggcac    4980 atcccctct ctgtgacaca ccctgtccac gccctggtt cttagttcca gccccactca    5040
taggacactc atagctcagg agggctccgc cttcaatccc acccgctaaa gtacttggag    5100
cggtctctcc ctccctcatc agcccaccaa accaaaccta gcctccaaga gtgggaagaa    5160
attaaagcaa gataggctat taagtgcaga gggagagaaa atgcctccaa catgtgagga    5220
agtaatgaga gaaatcatag aattttaagg ccatgattta aggccatcat ggcctaagct    5280
tgaaaggaga taggatcaaa gcttggcgta atcatggtca tagctgtttc ctgtgtgaaa    5340
ttgttatccg ctcacaattc cacacaacat acgagccgga agcataaagt gtaaagcctg    5400
gggtgcctaa tgagtgagct aactcacatt aattgcgttg cgctcactgc ccgcttttcca   5460 gtcgggaaac ctgtcgtgcc agctgcatta atgaatcggc caacgcgcgg ggagaggcgg    5520
tttgcgtatt gggcgctctt ccgcttcctc gctcactgac tcgctgcgct cggtcgttcg    5580
gctgcggcga gcggtatcag ctcactcaaa ggcggtaata cggttatcca cagaatcagg    5640
ggataacgca ggaaagaaca tgtgagcaaa aggccagcaa aaggccagga accgtaaaaa    5700
ggccgcgttg ctggcgtttt tccataggct ccgcccccct gacgagcatc acaaaaatcg    5760
acgctcaagt cagaggtggc gaaacccgac aggactataa agataccagg cgtttccccc    5820
tggaagctcc ctcgtgcgct ctcctgttcc gaccctgccg cttaccggat acctgtccgc    5880
ctttctccct tcgggaagcg tggcgctttc tcatagctca cgctgtaggt atctcagttc    5940
ggtgtaggtc gttcgctcca agctgggctg tgtgcacgaa ccccccgttc agcccgaccg    6000
ctgcgcctta tccggtaact atcgtcttga gtccaacccg gtaagacacg acttatcgcc    6060
actggcagca gccactggta acaggattag cagagcgagg tatgtaggcg gtgctacaga    6120
gttcttgaag tggtggccta actacggcta cactagaaga acagtatttg gtatctgcgc    6180
tctgctgaag ccagttacct tcggaaaaag agttggtagc tcttgatccg gcaaacaaac    6240
caccgctggt agcggtggtt tttttgtttg caagcagcag attacgcgca gaaaaaaagg    6300
atctcaagaa gatcctttga tcttttctac ggggtctgac gctcagtgga acgaaaactc    6360
acgttaaggg attttggtca tgagattatc aaaaaggatc ttcacctaga tccttttaaa    6420
ttaaaaatga gttttaaat caatctaaag tatatatgag taaacttggt ctgacagtta    6480
ccaatgctta atcagtgagg cacctatctc agcgatctgt ctatttcgtt catccatagt    6540
tgcctgactc cccgtcgtgt agataactac gatacgggag ggcttaccat ctggccccag    6600
tgctgcaatg ataccgcgag aaccacgctc accggctcca gatttatcag caataaacca    6660
gccagccgga agggccgagc gcagaagtgg tcctgcaact ttatccgcct ccatccagtc    6720
tattaattgt tgccgggaag ctagagtaag tagttcgcca gttaatagtt tgcgcaacgt    6780
tgttgccatt gctacaggca tcgtggtgtc acgctcgtcg tttggtatgg cttcattcag    6840
ctccggttcc caacgatcaa ggcgagttac atgatccccc atgttgtgca aaaaagcggt    6900
tagctccttc ggtcctccga tcgttgtcag aagtaagttg gccgcagtgt tatcactcat    6960
ggttatggca gcactgcata attctcttac tgtcatgcca tccgtaagat gcttttctgt    7020
```

```
gactggtgag tactcaacca agtcattctg agaatagtgt atgcggcgac cgagttgctc   7080
ttgcccggcg tcaatacggg ataataccgc gccacatagc agaactttaa aagtgctcat   7140
cattggaaaa cgttcttcgg ggcgaaaact ctcaaggatc ttaccgctgt tgagatccag   7200
ttcgatgtaa cccactcgtg cacccaactg atcttcagca tcttttactt tcaccagcgt   7260
ttctgggtga gcaaaaacag gaaggcaaaa tgccgcaaaa aagggaataa gggcgacacg   7320
gaaatgttga atactcatac tcttcctttt tcaatattat tgaagcattt atcagggtta   7380
ttgtctcatg agcggataca tatttgaatg tatttagaaa aataaacaaa tagggggttcc   7440 gcgcacattt ccccgaaaag tgccacctga cgtctaagaa accattatta tcatgacatt   7500
aacctataaa aataggcgta tcacgaggcc ctttcgggtc gcgcgtttcg gtgatgacgg   7560
tgaaaacctc tgacacatgc agctcccgtt gacggtcaca gcttgtctgt aagcggatgc   7620
cgggagcaga caagcccgtc agggcgcgtc agcgggtgtt ggcgggtgtc ggggctggct   7680
taactatgcg gcatcagagc agattgtact gagagtgcac cataaaattg taaacgttaa   7740
tattttgtta aaattcgcgt taaattttg ttaaatcagc tcattttta accaataggc   7800 cgaaatcggc aaaatccctt ataaatcaaa agaatagccc gagataggt tgagtgttgt   7860 tccagtttgg aacaagagtc cactattaaa gaacgtggac tccaacgtca aagggcgaaa   7920
aaccgtctat cagggcgatg gcccactacg tgaaccatca cccaaatcaa gttttttggg   7980
gtcgaggtgc cgtaaagcac taaatcggaa ccctaaaggg agccccgat ttagagcttg   8040 acggggaaag ccggcgaacg tggcgagaaa ggaagggaag aaagcgaaag gagcgggcgc   8100
tagggcgctg gcaagtgtag cggtcacgct gcgcgtaacc accacacccg ccgcgcttaa   8160
tgcgccgcta cagggcgcgt actatggttg ctttgacgta tgcggtgtga ataccgcac    8220 agatgcgtaa ggagaaaata ccgcatcagg cgccattcgc cattcaggct gcgcaactgt   8280
tgggaagggc gatcggtgcg ggcctcttcg ctattacgcc agctggcgaa aggggggatgt  8340 gctgcaaggc gattaagttg ggtaacgcca gggttttccc agtcacgacg ttgtaaaacg   8400
acggccagtg aattccatgg tctcaacttt c                                  8431
```

<210> SEQ ID NO 27
<211> LENGTH: 3813
<212> TYPE: DNA
<213> ORGANISM: Artificial Sequence
<220> FEATURE:
<223> OTHER INFORMATION: Synthetic polynucleotide

<400> SEQUENCE: 27

```
atggagttca tcccgacgca aactttctat aacagaaggt accaacccccg accctgggcc     60 ccacgcccta caattcaagt aattagacct agaccacgtc cacagaggca ggctgggcaa    120
ctcgcccagc tgatctccgc agtcaacaaa ttgaccatgc gcgcggtacc tcaacagaag    180
cctcgcagaa atcggaaaaa caagaagcaa aggcagaaga agcaggcgcc gcaaaacgac    240
ccaaagcaaa agaagcaacc accacaaaag aagccggctc aaaagaagaa gaaaccaggc    300
cgtagggaga gaatgtgcat gaaaattgaa atgattgca tcttcgaagt caagcatgaa     360
ggcaaagtga tgggctacgc atgcctggtg ggggataaag taatgaaacc agcacatgtg    420
aagggaacta tcgacaatgc cgatctggct aaactggcct ttaagcggtc gtctaaatac    480
gatcttgaat gtgcacagat accggtgcac atgaagtctg atgcctcgaa gtttacccac    540
gagaaacccg aggggtacta taactggcat cacggagcag tgcagtattc aggaggccgg    600
```

```
ttcactatcc cgacgggtgc aggcaagccg ggagacagcg gcagaccgat cttcgacaac    660
aaaggacggg tggtgccat cgtcctagga ggggccaacg aaggtgcccg cacggccctc     720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagacccgg atactaccag ctactaaaag catcgctgac ttgctctccc    960
caccgccaaa gacgcagtac taaggacaat tttaatgtct ataaagccac aagaccatat   1020
ctagctcatt gtcctgactg cggagaaggg cattcgtgcc acagccctat cgcattggag    1080
cgcatcagaa atgaagcaac ggacggaacg ctgaaaatcc aggtctcttt gcagatcggg    1140
ataaagacag atgacagcca cgattggacc aagctgcgct atatggatag ccatacgcca    1200
gcggacgcgg agcgagccgg attgcttgta aggacttcag caccgtgcac gatcaccggg    1260
accatgggac actttattct cgcccgatgc ccgaaaggag agacgctgac agtgggattt    1320
acggacagca gaaagatcag ccacacatgc acacacccgt tccatcatga accacctgtg    1380
ataggtaggg agaggttcca ctctcgacca caacatggta aagagttacc ttgcagcacg    1440
tacgtgcaga gcaccgctgc cactgctgag gagatagagg tgcatatgcc cccagatact    1500
cctgaccgca cgctgatgac gcagcagtct ggcaacgtga agatcacagt taatgggcag    1560
acggtgcggt acaagtgcaa ctgcggtggc tccggaggac taaactggta ccgcatgagc    1620
cccagcaacc agacggacaa gctggccgcc ttcggaggat ccaacgaggg actgacaacc    1680
acagacaaag tgatcaataa ctgcaaaatt gatcagtgcc atgctgcagt cactaatcac    1740
aagaattggc aatacaactc ccctttagtc ccgcgcaacg ctgaactcgg ggaccgtaaa    1800
ggaaagatcc acatcccatt cccattggca aacgtgactt gcagagtgcc aaaagcaaga    1860
aaccctacag taacttacgg aaaaaaccaa gtcaccatgc tgctgtatcc tgaccatccg    1920
acactcttgt cttaccgtaa catgggacag gaaccaaatt accacgagga gtgggtgaca    1980
cacaagaagg aggttacctt gaccgtgcct actgagggtc tggaggtcac ttggggcaac    2040
aacgaaccat acaagtactg gccgcagatg tctacgaacg gtactgctca tggtcaccca    2100
catgagataa tcttgtacta ttatgagctg tacccactta tgactgtagt cattgtgtcg    2160
gtggcctcgt tcgtgcttct gtcgatggtg ggcacagcag tgggaatgtg tgtgtgcgca    2220
cggcgcagat gcattacacc atatgaatta acaccaggag ccactgttcc cttcctgctc    2280
agcctgctat gctgcgtcag aacgaccaag gcggccacat attacgaggc tgcggcatat    2340
ctatggaacg aacagcagcc cctgttctgg ttgcaggctc ttatcccgct ggccgccttg    2400
atcgtcctgt gcaactgtct gaaactcttg ccatgctgct gtaagaccct ggctttttta    2460
gccgtaatga gcatcggtgc ccacactgtg agcgcgtacg aacacgtaac agtgatcccg    2520
aacacggtgg gagtaccgta taagactctt gtcaacagac cgggttacag ccccatggtg    2580
ttggagatgg agctacaatc agtcacccttg gaaccaacac tgtcacttga ctacatcacg    2640
tgcgagtaca aaactgtcat cccctccccg tacgtgaagt gctgtggtac agcagagtgc    2700
aaggacaaga gcctaccaga ctacagctgc aaggtctta ctggagtcta cccatttatg    2760
tggggcggcg cctactgctt ttgcgacgcc gaaaatacgc aattgagcga ggcacatgta    2820
gagaaatctg aatcttgcaa aacagagttt gcatcggcct acagagccca caccgcatcg    2880
gcgtcggcga agctccgcgt cctttaccaa ggaaacaaca ttaccgtagc tgcctacgct    2940
aacggtgacc atgccgtcac agtaaaggac gccaagtttg tcgtgggccc aatgtcctcc    3000
```

```
gcctggacac cttttgacaa caaaatcgtg gtgtacaaag gcgacgtcta caacatggac    3060
tacccacctt ttggcgcagg aagaccagga caatttggtg acattcaaag tcgtacaccg    3120
gaaagtaaag acgtttatgc caacactcag ttggtactac agaggccagc agcaggcacg    3180
gtacatgtac catactctca ggcaccatct ggcttcaagt attggctgaa ggaacgagga    3240
gcatcgctac agcacacggc accgttcggt tgccagattg cgacaaaccc ggtaagagct    3300
gtaaattgcg ctgtggggaa cataccaatt ccatcgacac taccggatgc ggcctttact    3360
agggttgtcg atgcaccctc tgtaacggac atgtcatgcg aagtaccagc ctgcactcac    3420
tcctccgact ttgggggcgt cgccatcatc aaatacacag ctagcaagaa aggtaaatgt    3480
gcagtacatt cgatgaccaa cgccgttacc attcgagaag ccgacgtaga agtagagggg    3540
aactcccagc tgcaaatatc cttctcaaca gccctggcaa gcgccgagtt tcgcgtgcaa    3600
gtgtgctcca cacaagtaca ctgcgcagcc gcatgccacc ctccaaagga ccacatagtc    3660
aattacccag catcacacac cacccttggg gtccaggata tatccacaac ggcaatgtct    3720
tgggtgcaga agattacggg aggagtagga ttaattgttg ctgttgctgc cttaattttta   3780 attgtggtgc tatgcgtgtc gtttagcagg cac                                 3813

<210> SEQ ID NO 28
<211> LENGTH: 3837
<212> TYPE: DNA
<213> ORGANISM: Artificial Sequence
<220> FEATURE:
<223> OTHER INFORMATION: Synthetic polynucleotide

<400> SEQUENCE: 28
atgttcccgt tccagccaat gtatccgatg cagccaatgc cctatcgcaa cccgttcgcg      60
gccccgcgca ggccctggtt ccccagaacc gaccctttc tggcgatgca ggtgcaggaa     120
ttaacccgct cgatggctaa cctgacgttc aagcaacgcc gggacgcgcc acctgagggg    180
ccatccgcta ataaaccgaa gaaggaggcc tcgcaaaaac agaaaggggg aggccaaggg    240
aagaagaaga gaaccaagg gaagaagaag gctaagacag gccgcctaa tccgaaggca     300 cagaatggaa acaagaagaa gaccaacaag aaaccaggca agagacagcg catggtcatg    360
aaattggaat ctgacaagac gttcccaatc atgttggaag ggaagataaa cggctacgct    420
tgtgtggtcg agggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa atgggcgtt tcacggtgcc gaaaggagtt     660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccgga aggaaaagga tccaccgag ggagctgttt   1020 aatgagtata gctaacgcg cccttacatg gccagatgca tcagatgtgc agttgggagc    1080
tgccatagtc caatagcaat cgaggcagta aagagcgacg ggcacgacgg ttatgttaga    1140
cttcagactt cctcgcagta tggcctggat tcctccggca acttaaaggg caggaccatg    1200
```

```
cggtatgaca tgcacgggac cattaaagag ataccactac atcaagtgtc actctataca    1260
tctcgcccgt gtcacattgt ggatgggcac ggttatttcc tgcttgccag gtgcccggca    1320
ggggactcca tcaccatgga atttaagaaa gattccgtca gacactcctg ctcggtgccg    1380
tatgaagtga aatttaatcc tgtaggcaga gaactctata ctcatccccc agaacacgga    1440
gtagagcaag cgtgccaagt ctacgcacat gatgcacaga acagaggagc ttatgtcgag    1500
atgcacctcc cgggctcaga agtggacagc agtttggttt ccttgagcgg cagttccgga    1560
ggactaaact ggtaccgcat gagccccagc aaccagacgg acaagctggc cgccttcgga    1620
ggatcctcag tcaccgtgac acctcctgat gggactagcg ccctggtgga atgcgagtgt    1680
ggcggcacaa agatctccga gaccatcaac aagacaaaac agttcagcca gtgcacaaag    1740
aaggagcagt gcagagcata tcggctgcag aacgataagt gggtgtataa ttctgacaaa    1800
ctgcccaaag cagcgggagc caccttaaaa ggaaaactgc atgtcccatt cttgctggca    1860
gacggcaaat gcaccgtgcc tctagcacca gaacctatga taaccttcgg tttcagatca    1920
gtgtcactga aactgcaccc taagaatccc acatatctaa tcacccgcca acttgctgat    1980
gagcctcact acacgcacga gctcatatct gaaccagctg ttaggaattt taccgtcacc    2040
gaaaaagggt gggagtttgt atggggaaac cacccgccga aaaggttttg ggcacaggaa    2100
acagcacccg gaaatccaca tgggctaccg cacgaggtga taactcatta ttaccacaga    2160
taccctatgt ccaccatcct gggttttgtca atttgtgccg ccattgcaac cgtttccgtt    2220
gcagcgtcta cctggctgtt ttgcagatca agagttgcgt gcctaactcc ttaccggcta    2280
acacctaacg ctaggatacc attttgtctg gctgtgcttt gctgcgcccg cactgcccgg    2340
gccgagacca cctgggagtc cttggatcac ctatggaaca ataaccaaca gatgttctgg    2400
attcaattgc tgatccctct ggccgccttg atcgtagtga ctcgcctgct caggtgcgtg    2460
tgctgtgtcg tgccttttttt agtcatggcc ggcgccgcag gcgccggcgc ctacgagcac    2520
gcgaccacga tgccgagcca agcgggaatc tcgtataaca ctatagtcaa cagagcaggc    2580
tacgcaccac tccctatcag cataacacca acaaagatca agctgatacc tacagtgaac    2640
ttggagtacg tcacctgcca ctacaaaaca ggaatggatt caccagccat caaatgctgc    2700
ggatctcagg aatgcactcc aacttacagg cctgatgaac agtgcaaagt cttcacaggg    2760
gtttaccccgt tcatgtgggg tggtgcatat tgcttttgcg acactgagaa cacccaagtc    2820
agcaaggcct acgtaatgaa atctgacgac tgccttgcgg atcatgctga agcatataaa    2880
gcgcacacag cctcagtgca ggcgttcctc aacatcacag tgggagaaca ctctattgtg    2940
actaccgtgt atgtgaatgg agaaactcct gtgaatttca atgggtcaa ataactgca     3000
ggtccgcttt ccacagcttg gacaccttt gatcgcaaaa tcgtgcagta tgccggggag    3060
atctataatt atgattttcc tgagtatggg gcaggacaac caggagcatt tggagatata    3120
caatccagaa cagtctcaag ctctgatctg tatgccaata ccaacctagt gctgcagaga    3180
cccaaagcag gagcgatcca cgtgcctac actcaggcac cttcgggttt tgagcaatgg    3240
aagaaagata agctccatc attgaaattt accgcccctt tcggatgcga aatatataca    3300
aaccccattc gcgccgaaaa ctgtgctgta gggtcaattc cattagcctt tgacattccc    3360
gacgccttgt tcaccagggt gtcagaaaca ccgacacttt cagcggccga atgcactctt    3420
aacgagtgcg tgtattcttc cgactttggt gggatcgcca cggtcaagta ctcggccagc    3480
aagtcaggca gtgcgcagt ccatgtgcca tcagggactg ctaccctaaa agaagcagca    3540
gtcgagctaa ccgagcaagg gtcggcgact atccattttct cgaccgcaaa tatccacccg    3600
```

```
gagttcaggc tccaaatatg cacatcatat gttacgtgca aaggtgattg tcaccccccg   3660
aaagaccata ttgtgacaca ccctcagtat cacgcccaaa catttacagc cgcggtgtca   3720
aaaaccgcgt ggacgtggtt aacatccctg ctgggaggat cagccgtaat tattataatt   3780
ggcttggtgc tggctactat tgtggccatg tacgtgctga ccaaccagaa acataat     3837
```

<210> SEQ ID NO 29
<211> LENGTH: 3798
<212> TYPE: DNA
<213> ORGANISM: Artificial Sequence
<220> FEATURE:
<223> OTHER INFORMATION: Synthetic polynucleotide

<400> SEQUENCE: 29

```
atggagttca tcccgacgca aactttctat aacagaaggt accaaccccg accctgggcc     60
ccacgcccta caattcaagt aattagacct agaccacgtc cacagaggca ggctgggcaa    120
ctcgcccagc tgatctccgc agtcaacaaa ttgaccatgc gcgcggtacc tcaacagaag    180
cctcgcagaa atcggaaaaa caagaagcaa aggcagaaga agcaggcgcc gcaaaacgac    240
ccaaagcaaa agaagcaacc accacaaaag aagccggctc aaaagaagaa gaaaccaggc    300
cgtagggaga gaatgtgcat gaaaattgaa aatgattgca tcttcgaagt caagcatgaa    360
ggcaaagtga tgggctacgc atgcctggtg ggggataaag taatgaaacc agcacatgtg    420
aagggaacta tcgacaatgc cgatctggct aaactggcct ttaagcggtc gtctaaatac    480
gatcttgaat gtgcacagat accggtgcac atgaagtctg atgcctcgaa gtttacccac    540
gagaaacccg aggggtacta taactggcat cacgagcag tgcagtattc aggaggccgg    600
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840 ccgcccttgca caccctgctg ctacgaaaag gaaccggaaa gcaccttgcg catgcttgag    900
gacaacgtga tgagacccgg atactaccag ctactaaaag catcgctgac ttgctctccc    960
caccgccaaa gacgcagtac taaggacaat tttaatgtct ataaagccac aagaccatat   1020
ctagctcatt gtcctgactg cggagaaggg cattcgtgcc acagccctat cgcattggag   1080
cgcatcagaa atgaagcaac ggacggaacg ctgaaaatcc aggtctcttt gcagatcggg   1140
ataaagacag atgacagcca cgattggacc aagctgcgct atatggatag ccatacgcca   1200
gcggacgcgg agcgagccgg attgcttgta aggacttcag caccgtgcac gatcaccggg   1260
accatgggac actttattct cgcccgatgc ccgaaaggag agacgctgac agtgggattt   1320
acggacagca gaaagatcag ccacacatgc acacacccgt ccatcatga ccacctgtg    1380 ataggtaggg agaggttcca ctctcgacca caacatggta aagagttacc ttgcagcacg   1440
tacgtgcaga gcaccgctgc cactgctgag gagatagagg tgcatatgcc cccagatact   1500
cctgaccgca cgctgatgac gcagcagtct ggcaacgtga agatcacagt taatgggcag   1560
acggtgcggt acaagtgcaa ctgcggtggc tccgaggcg cgccatcag cctgcacccc    1620 aaggccaaga tcgaggaatc tggatccaac gagggactga caaccacaga caaagtgatc   1680
aataactgca aaattgatca gtgccatgct gcagtcacta atcacaagaa ttggcaatac   1740
aactcccctt tagtcccgcg caacgctgaa ctcgggggacc gtaaaggaaa gatccacatc   1800
```

```
ccattcccat tggcaaacgt gacttgcaga gtgccaaaag caagaaaccc tacagtaact    1860
tacggaaaaa accaagtcac catgctgctg tatcctgacc atccgacact cttgtcttac    1920
cgtaacatgg gacaggaacc aaattaccac gaggagtggg tgacacacaa gaaggaggtt    1980
accttgaccg tgcctactga gggtctggag gtcacttggg caacaacga accatacaag    2040 tactggccgc agatgtctac gaacggtact gctcatggtc acccacatga gataatcttg    2100
tactattatg agctgtaccc cactatgact gtagtcattg tgtcggtggc ctcgttcgtg    2160
cttctgtcga tggtgggcac agcagtggga atgtgtgtgt gcgcacggcg cagatgcatt    2220
acaccatatg aattaacacc aggagccact gttcccttcc tgctcagcct gctatgctgc    2280
gtcagaacga ccaaggcggc cacatattac gaggctgcgg catatctatg aacgaacag    2340 cagcccctgt tctggttgca ggctcttatc ccgctggccg ccttgatcgt cctgtgcaac    2400
tgtctgaaac tcttgccatg ctgctgtaag accctggctt ttttagccgt aatgagcatc    2460
ggtgcccaca ctgtgagcgc gtacgaacac gtaacagtga tcccgaacac ggtgggagta    2520
ccgtataaga ctcttgtcaa cagaccgggt tacagcccca tggtgttgga gatggagcta    2580
caatcagtca ccttggaacc aacactgtca cttgactaca tcacgtgcga gtacaaaact    2640
gtcatcccct ccccgtacgt gaagtgctgt ggtacagcag agtgcaagga caagagccta    2700
ccagactaca gctgcaaggt ctttactgga gtctacccat ttatgtgggg cggcgcctac    2760
tgcttttgcg acgccgaaaa tacgcaattg agcgaggcac atgtagagaa atctgaatct    2820
tgcaaaacag agtttgcatc ggcctacaga gcccacaccg catcggcgtc ggcgaagctc    2880
cgcgtccttt accaaggaaa caacattacc gtagctgcct acgctaacgg tgaccatgcc    2940
gtcacagtaa aggacgccaa gtttgtcgtg ggcccaatgt cctccgcctg gacaccttt    3000 gacaacaaaa tcgtggtgta caaaggcgac gtctacaaca tggactaccc accttttggc    3060
gcaggaagac caggacaatt tggtgacatt caaagtcgta caccggaaag taaagacgtt    3120
tatgccaaca ctcagttggt actacagagg ccagcagcag gcacggtaca tgtaccatac    3180
tctcaggcac catctggctt caagtattgg ctgaaggaac gaggagcatc gctacagcac    3240
acggcaccgt tcggttgcca gattgcgaca aacccggtaa gagctgtaaa ttgcgctgtg    3300
gggaacatac caatttccat cgacataccg gatgcggcct ttactagggt tgtcgatgca    3360
ccctctgtaa cggacatgtc atgcgaagta ccagcctgca ctcactcctc cgactttggg    3420
ggcgtcgcca tcatcaaata cacagctagc aagaaaggta aatgtgcagt acattcgatg    3480
accaacgccg ttaccattcg agaagccgac gtagaagtag aggggaactc ccagctgcaa    3540
atatccttct caacagccct ggcaagcgcc gagtttcgcg tgcaagtgtg ctccacacaa    3600
gtacactgcg cagccgcatg ccaccctcca aaggaccaca tagtcaatta cccagcatca    3660
cacaccaccc ttggggtcca ggatatatcc acaacggcaa tgtcttgggt gcagaagatt    3720
acgggaggag taggattaat tgttgctgtt gctgccttaa tttttaattgt ggtgctatgc    3780 gtgtcgttta gcaggcac                                                 3798
```

<210> SEQ ID NO 30
<211> LENGTH: 3822
<212> TYPE: DNA
<213> ORGANISM: Artificial Sequence
<220> FEATURE:
<223> OTHER INFORMATION: Synthetic polynucleotide

<400> SEQUENCE: 30

```
atgttcccgt tccagccaat gtatccgatg cagccaatgc cctatcgcaa cccgttcgcg      60
```

```
gccccgcgca ggccctggtt ccccagaacc gacccttttc tggcgatgca ggtgcaggaa    120
ttaacccgct cgatggctaa cctgacgttc aagcaacgcc gggacgcgcc acctgagggg    180
ccatccgcta ataaaccgaa gaaggaggcc tcgcaaaaac agaaaggggg aggccaaggg    240
aagaagaaga agaaccaagg gaagaagaag gctaagacag gccgcctaa tccgaaggca     300 cagaatggaa acaagaagaa gaccaacaag aaaccaggca agagacagcg catggtcatg    360
aaattggaat ctgacaagac gttcccaatc atgttggaag gaagataaa cggctacgct     420 tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa aatgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagccettt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960
ctgctggaag cagctgttaa gtgccccgga aggaaaagga gatccaccga ggagctgttt   1020
aatgagtata agctaacgcg cccttacatg gccagatgca tcagatgtgc agttgggagc   1080
tgccatagtc caatagcaat cgaggcagta aagagcgacg gcacgacgg ttatgttaga     1140 cttcagactt cctcgcagta tggcctggat tcctccggca acttaaaggg caggaccatg   1200
cggtatgaca tgcacgggac cattaaagag ataccactac atcaagtgtc actctataca   1260
tctcgcccgt gtcacattgt ggatgggcac ggttatttcc tgcttccag gtgcccggca    1320 ggggactcca tcaccatgga atttaagaaa gattccgtca gacactcctg ctcggtgccg   1380
tatgaagtga aatttaatcc tgtaggcaga gaactctata ctcatccccc agaacacgga   1440
gtagagcaag cgtgccaagt ctacgcacat gatgcacaga acagaggagc ttatgtcgag   1500
atgcacctcc cgggctcaga agtggacagc agtttggttt ccttgagcgg cagttccgga   1560
ggcggcgcca tcagcctgca ccccaaggcc aagatcgagg aatctggatc ctcagtcacc   1620
gtgacacctc ctgatgggac tagcgccctg gtggaatgcg agtgtggcgg cacaaagatc   1680
tccgagacca tcaacaagac aaaacagttc agccagtgca caaagaagga gcagtgcaga   1740
gcatatcggc tgcagaacga taagtgggtg tataattctg acaaactgcc caaagcagcg   1800
ggagccacct taaaaggaaa actgcatgtc ccattcttgc tggcagacgg caaatgcacc   1860
gtgcctctag caccagaacc tatgataacc ttcggtttca gatcagtgtc actgaaactg   1920 cacccctaaga atcccacata tctaatcacc cgccaacttg ctgatgagcc tcactacacg   1980
cacgagctca tatctgaacc agctgttagg aattttaccg tcaccgaaaa agggtgggag   2040
tttgtatggg gaaaccaccc gccgaaaagg ttttggcac aggaaacagc acccggaaat     2100
ccacatgggc taccgcacga ggtgataact cattattacc acagataccc tatgtccacc    2160
atcctgggtt tgtcaatttg tgccgccatt gcaaccgttt ccgttgcagc gtctacctgg    2220
ctgttttgca gatcaagagt tgcgtgccta actccttacc ggctaacacc taacgctagg   2280
ataccatttt gtctggctgt gctttgctgc gcccgcactg cccgggccga gaccacctgg   2340
gagtccttgg atcacctatg gaacaataac caacagatgt tctggattca attgctgatc   2400
```

| | |
|---|---|
| cctctggccg ccttgatcgt agtgactcgc ctgctcaggt gcgtgtgctg tgtcgtgcct | 2460 |
| tttttagtca tggccggcgc cgcaggcgcc ggcgcctacg agcacgcgac cacgatgccg | 2520 |
| agccaagcgg gaatctcgta taacactata gtcaacagag caggctacgc accactccct | 2580 |
| atcagcataa caccaacaaa gatcaagctg ataccuacag tgaacttgga gtacgtcacc | 2640 |
| tgccactaca aaacaggaat ggattcacca gccatcaaat gctgcggatc tcaggaatgc | 2700 |
| actccaactt acaggcctga tgaacagtgc aaagtcttca caggggttta cccgttcatg | 2760 |
| tggggtggtg catattgctt ttgcgacact gagaacaccc aagtcagcaa ggcctacgta | 2820 |
| atgaaatctg acgactgcct tgcggatcat gctgaagcat ataaagcgca cacagcctca | 2880 |
| gtgcaggcgt tcctcaacat cacagtggga gaacactcta ttgtgactac cgtgtatgtg | 2940 |
| aatggagaaa ctcctgtgaa tttcaatggg gtcaaaataa ctgcaggtcc gctttccaca | 3000 |
| gcttggacac cctttgatcg caaaatcgtg cagtatgccg gggagatcta taattatgat | 3060 |
| tttcctgagt atggggcagg acaaccagga gcatttggag atatacaatc cagaacagtc | 3120 |
| tcaagctctg atctgtatgc caataccaac ctagtgctgc agagacccaa agcaggagcg | 3180 |
| atccacgtgc catacactca ggcaccttcg ggttttgagc aatggaagaa agataaagct | 3240 |
| ccatcattga aatttaccgc cccttttcgga tgcgaaatat atacaaaccc cattcgcgcc | 3300 |
| gaaaactgtg ctgtagggtc aattccatta gcctttgaca ttcccgacgc cttgttcacc | 3360 |
| agggtgtcag aaacaccgac actttcagcg gccgaatgca ctcttaacga gtgcgtgtat | 3420 |
| tcttccgact tggtgggat cgccacggtc aagtactcgg ccagcaagtc aggcaagtgc | 3480 |
| gcagtccatg tgccatcagg gactgctacc ctaaaagaag cagcagtcga gctaaccgag | 3540 |
| caagggtcgg cgactatcca tttctcgacc gcaaatatcc acccggagtt caggctccaa | 3600 |
| atatgcacat catatgttac gtgcaaaggt gattgtcacc ccccgaaaga ccatattgtg | 3660 |
| acacaccctc agtatcacgc ccaaacattt acagccgcgg tgtcaaaaac cgcgtggacg | 3720 |
| tggttaacat ccctgctggg aggatacagcc gtaattatta taattggctt ggtgctggct | 3780 |
| actattgtgg ccatgtacgt gctgaccaac cagaaacata at | 3822 |

<210> SEQ ID NO 31
<211> LENGTH: 3792
<212> TYPE: DNA
<213> ORGANISM: Artificial Sequence
<220> FEATURE:
<223> OTHER INFORMATION: Synthetic polynucleotide

<400> SEQUENCE: 31

| | |
|---|---|
| atggagttca tcccgacgca aactttctat aacagaaggt accaaccccg accctgggcc | 60 |
| ccacgcccta caattcaagt aattagacct agaccacgtc cacagaggca ggctgggcaa | 120 |
| ctcgcccagc tgatctccgc agtcaacaaa ttgaccatgc gcgcggtacc tcaacagaag | 180 |
| cctcgcagaa atcggaaaaa caagaagcaa aggcagaaga agcaggcgcc gcaaaacgac | 240 |
| ccaaagcaaa agaagcaacc accacaaaag aagccggctc aaaagaagaa gaaaccaggc | 300 |
| cgtagggaga gaatgtgcat gaaaattgaa atgattgca tcttcgaagt caagcatgaa | 360 |
| ggcaaagtga tgggctacgc atgcctggtg ggggataaag taatgaaacc agcacatgtg | 420 |
| aagggaacta tcgacaatgc cgatctggct aaactggcct ttaagcggtc gtctaaatac | 480 |
| gatcttgaat gtgcacagat accggtgcac atgaagtctg atgcctcgaa gtttacccac | 540 |
| gagaaacccg aggggtacta taactggcat cacggagcag tgcagtattc aggaggccgg | 600 |
| ttcactatcc cgacgggtgc aggcaagccg ggagacagcg gcagaccgat cttcgacaac | 660 |

| | |
|---|---|
| aaaggacggg tggtggccat cgtcctagga ggggccaacg aaggtgcccg cacggccctc | 720 |
| tccgtggtga cgtggaacaa agacatcgtc acaaaaatta cccctgaggg agccgaagag | 780 |
| tggagcctcg ccctcccggt cttgtgcctg ttggcaaaca ctacattccc ctgctctcag | 840 |
| ccgccttgca caccctgctg ctacgaaaag gaaccggaaa gcaccttgcg catgcttgag | 900 |
| gacaacgtga tgagacccgg atactaccag ctactaaaag catcgctgac ttgctctccc | 960 |
| caccgccaaa gacgcagtac taaggacaat tttaatgtct ataaagccac aagaccatat | 1020 |
| ctagctcatt gtcctgactg cggagaaggg cattcgtgcc acagccctat cgcattggag | 1080 |
| cgcatcagaa atgaagcaac ggacggaacg ctgaaaatcc aggtctcttt gcagatcggg | 1140 |
| ataaagacag atgacagcca cgattggacc aagctgcgct atatggatag ccatacgcca | 1200 |
| gcggacgcgg agcgagccgg attgcttgta aggacttcag caccgtgcac gatcaccggg | 1260 |
| accatgggac actttattct cgcccgatgc ccgaaggag agacgctgac agtgggattt | 1320 |
| acggacagca gaaagatcag ccacacatgc acacacccgt tccatcatga accacctgtg | 1380 |
| ataggtaggg agaggttcca ctctcgacca caacatggta aagagttacc ttgcagcacg | 1440 |
| tacgtgcaga gcaccgctgc cactgctgag gagatagagg tgcatatgcc cccagatact | 1500 |
| cctgaccgca cgctgatgac gcagcagtct ggcaacgtga agatcacagt taatgggcag | 1560 |
| acggtgcggt acaagtgcaa ctgcggtggc tccggaggct gcatcatcag ctacggcgga | 1620 |
| gccgactact gcggcggatc caacgaggga ctgacaacca cagacaaagt gatcaataac | 1680 |
| tgcaaaattg atcagtgcca tgctgcagtc actaatcaca agaattgcaa atacaactcc | 1740 |
| cctttagtcc cgcgcaacgc tgaactcggg gaccgtaaag gaaagatcca catcccattc | 1800 |
| ccattggcaa acgtgacttg cagagtgcca aaagcaagaa accctacagt aacttacgga | 1860 |
| aaaaaccaag tcaccatgct gctgtatcct gaccatccga cactcttgtc ttaccgtaac | 1920 |
| atgggacagg aaccaaatta ccacgaggag tgggtgacac acaagaagga ggttaccttg | 1980 |
| accgtgccta ctgagggtct ggaggtcact tggggcaaca acgaaccata caagtactgg | 2040 |
| ccgcagatgt ctacgaacgg tactgctcat ggtcacccac atgagataat cttgtactat | 2100 |
| tatgagctgt accccactat gactgtagtc attgtgtcgg tggcctcgtt cgtgcttctg | 2160 |
| tcgatggtgg gcacagcagt gggaatgtgt gtgtgcgcac ggcgcagatg cattacacca | 2220 |
| tatgaattaa caccaggagc cactgttccc ttcctgctca gcctgctatg ctgcgtcaga | 2280 |
| acgaccaagg cggccacata ttacgaggct gcggcatatc tatggaacga acagcagccc | 2340 |
| ctgttctggt tgcaggctct tatcccgctg gccgccttga tcgtcctgtg caactgtctg | 2400 |
| aaactcttgc catgctgctg taagacccctg gctttttag ccgtaatgag catcggtgcc | 2460 |
| cacactgtga gcgcgtacga acacgtaaca gtgatcccga acacggtggg agtaccgtat | 2520 |
| aagactcttg tcaacagacc gggttacagc cccatggtgt tggagatgga gctacaatca | 2580 |
| gtcaccttgg aaccaacact gtcacttgac tacatcacgt gcgagtacaa aactgtcatc | 2640 |
| ccctcccgt acgtgaagtg ctgtggtaca gcagagtgca aggacaagag cctaccagac | 2700 |
| tacagctgca aggtctttac tggagtctac ccatttatgt ggggcggcgc ctactgcttt | 2760 |
| tgcgacgccg aaaatacgca attgagcgag gcacatgtag agaaatctga atcttgcaaa | 2820 |
| acagagtttg catcggccta cagagcccac accgcatcgg cgtcggcgaa gctccgcgtc | 2880 |
| ctttaccaag gaaacaacat taccgtagct gcctacgcta acggtgacca tgccgtcaca | 2940 |
| gtaaaggacg ccaagttgt cgtgggccca atgtcctccg cctggacacc ttttgacaac | 3000 |

```
aaaatcgtgg tgtacaaagg cgacgtctac aacatggact acccaccttt tggcgcagga    3060
agaccaggac aatttggtga cattcaaagt cgtacaccgg aaagtaaaga cgtttatgcc    3120
aacactcagt tggtactaca gaggccagca gcaggcacgg tacatgtacc atactctcag    3180
gcaccatctg gcttcaagta ttggctgaag aacgaggag catcgctaca gcacacggca    3240
ccgttcggtt gccagattgc gacaaacccg gtaagagctg taaattgcgc tgtggggaac    3300
ataccaattt ccatcgacat accggatgcg gcctttacta gggttgtcga tgcaccctct    3360
gtaacggaca tgtcatgcga agtaccagcc tgcactcact cctccgactt tggggcgtc     3420 gccatcatca atacacagc tagcaagaaa ggtaaatgtg cagtacattc gatgaccaac    3480
gccgttacca ttcgagaagc cgacgtagaa gtagagggga actcccagct gcaaatatcc    3540
ttctcaacag ccctggcaag cgccgagttt cgcgtgcaag tgtgctccac acaagtacac    3600
tgcgcagccg catgccaccc tccaaaggac cacatagtca attacccagc atcacacacc    3660
acccttgggg tccaggatat atccacaacg gcaatgtctt gggtgcagaa gattacggga    3720
ggagtaggat taattgttgc tgttgctgcc ttaattttaa ttgtggtgct atgcgtgtcg    3780
tttagcaggc ac                                                       3792

<210> SEQ ID NO 32
<211> LENGTH: 3816
<212> TYPE: DNA
<213> ORGANISM: Artificial Sequence
<220> FEATURE:
<223> OTHER INFORMATION: Synthetic polynucleotide

<400> SEQUENCE: 32
atgttcccgt ccagccaat gtatccgatg cagccaatgc cctatcgcaa cccgttcgcg      60
gccccgcgca ggccctggtt ccccagaacc gacccttttc tggcgatgca ggtgcaggaa    120
ttaacccgct cgatggctaa cctgacgttc aagcaacgcc gggacgcgcc acctgagggg    180
ccatccgcta taaaccgaa gaaggaggcc tcgcaaaaac agaaagggg aggccaaggg     240 aagaagaaga gaaccaagg gaagaagaag gctaagacag ggccgcctaa tccgaaggca    300
cagaatggaa acaagaagaa gaccaacaag aaaccaggca agacagcg catggtcatg      360 aaattggaat ctgacaagac gttcccaatc atgttggaag ggaagataaa cggctacgct    420
tgtgtggtcg gagggaagtt attcaggccg atgcatgtgg aagcaagat cgacaacgac    480 gttctggccg cgcttaagac gaagaaagca tccaaatacg atcttgagta tgcagatgtg    540
ccacagaaca tgcgggccga tacattcaaa tacacccatg agaaacccca aggctattac    600
agctggcatc atggagcagt ccaatatgaa atgggcgtt tcacggtgcc gaaaggagtt    660
ggggccaagg gagacagcgg acgacccatt ctggataacc agggacgggt ggtcgctatt    720
gtgctgggag gtgtgaatga aggatctagg acagcccttt cagtcgtcat gtggaacgag    780
aagggagtta ccgtgaagta tactccagag aactgcgagc aatggtcact agtgaccacc    840
atgtgtctgc tcgccaatgt gacgttccca tgtgctcaac caccaatttg ctacgacaga    900
aaaccagcag agactttggc catgctcagc gttaacgttg acaacccggg ctacgatgag    960 ctgctgaag cagctgttaa gtgccccgga aggaaaaga gatccaccga ggagctgttt    1020
aatgagtata gctaacgcg cccttacatg gccagatgca tcagatgtgc agttgggagc    1080
tgccatagtc caatagcaat cgaggcagta aagagcgacg ggcacgacgg ttatgttaga    1140
cttcagactt cctcgcagta tggcctggat tcctccggca acttaaaggg caggaccatg    1200
cggtatgaca tgcacgggac cattaaagag ataccactac atcaagtgtc actctataca    1260
```

```
tctcgcccgt gtcacattgt ggatgggcac ggttatttcc tgcttgccag gtgcccggca    1320
ggggactcca tcaccatgga atttaagaaa gattccgtca gacactcctg ctcggtgccg    1380
tatgaagtga aatttaatcc tgtaggcaga gaactctata ctcatccccc agaacacgga    1440
gtagagcaag cgtgccaagt ctacgcacat gatgcacaga acagaggagc ttatgtcgag    1500
atgcacctcc cgggctcaga agtggacagc agtttggttt ccttgagcgg cagttccgga    1560
ggctgcatca tcagctacgg cggagccgac tactgcggcg gatcctcagt caccgtgaca    1620
cctcctgatg ggactagcgc cctggtggaa tgcgagtgtg gcggcacaaa gatctccgag    1680
accatcaaca agacaaaaca gttcagccag tgcacaaaga aggagcagtg cagagcatat    1740
cggctgcaga acgataagtg ggtgtataat tctgacaaac tgcccaaagc agcgggagcc    1800
accttaaaag gaaaactgca tgtcccattc ttgctggcag acggcaaatg caccgtgcct    1860
ctagcaccag aacctatgat aaccttcggt ttcagatcag tgtcactgaa actgcaccct    1920
aagaatccca catatctaat cacccgccaa cttgctgatg agcctcacta cacgcacgag    1980
ctcatatctg aaccagctgt taggaatttt accgtcaccg aaaaagggtg ggagtttgta    2040
tggggaaacc acccgccgaa aaggttttgg gcacaggaaa cagcacccgg aaatccacat    2100
gggctaccgc acgaggtgat aactcattat taccacagat accctatgtc caccatcctg    2160
ggtttgtcaa tttgtgccgc cattgcaacc gtttccgttg cagcgtctac ctggctgttt    2220
tgcagatcaa gagttgcgtg cctaactcct taccggctaa cacctaacgc taggatacca    2280
ttttgtctgg ctgtgctttg ctgcgcccgc actgcccggg ccgagaccac ctgggagtcc    2340
ttggatcacc tatggaacaa taaccaacag atgttctgga ttcaattgct gatccctctg    2400
gccgccttga tcgtagtgac tcgcctgctc aggtgcgtgt gctgtgtcgt gccttttta    2460 gtcatggccg gcgccgcagg cgccggcgcc tacgagcacg cgaccacgat gccgagccaa    2520 gcggaatct cgtataacac tatagtcaac agagcaggct acgcaccact ccctatcagc    2580
ataacaccaa caaagatcaa gctgataccct acagtgaact tggagtacgt cacctgccac    2640
tacaaaacag gaatggattc accagccatc aaatgctgcg gatctcagga atgcactcca    2700
acttacaggc ctgatgaaca gtgcaaagtc ttcacagggg tttacccgtt catgtggggt    2760
ggtgcatatt gcttttgcga cactgagaac acccaagtca gcaaggccta cgtaatgaaa    2820
tctgacgact gccttgcgga tcatgctgaa gcatataaag cgcacacagc ctcagtgcag    2880
gcgttcctca acatcacagt gggagaacac tctattgtga ctaccgtgta tgtgaatgga    2940
gaaactcctg tgaatttcaa tggggtcaaa ataactgcag gtccgctttc cacagcttgg    3000 acacccttg atcgcaaaat cgtgcagtat gccggggaga tatataatta tgattttcct    3060
gagtatgggg caggacaacc aggagcattt ggagatatac aatccagaac agtctcaagc    3120
tctgatctgt atgccaatac caacctagtg ctgcagagac ccaaagcagg agcgatccac    3180
gtgccataca ctcaggcacc ttcgggtttt gagcaatgga gaaagataa agctccatca    3240 ttgaaattta ccgcccttt cggatgcgaa atatatacaa accccattcg cgccgaaaac    3300
tgtgctgtag gtcaattcc attagccttt gacattcccg acgccttgtt caccagggtg    3360
tcagaaacac cgacactttc agcggccgaa tgcactctta acgagtgcgt gtattcttcc    3420
gactttggtg ggatcgccac ggtcaagtac tcggccagca gtcaggcaa gtgcgcagtc    3480 catgtgccat cagggactgc taccctaaaa gaagcagcag tcgagctaac cgagcaaggg    3540
tcggcgacta tccatttctc gaccgcaaat atccaccccg agttcaggct ccaaatatgc    3600
```

```
acatcatatg ttacgtgcaa aggtgattgt cacccccga aagaccatat tgtgacacac    3660
cctcagtatc acgcccaaac atttacagcc gcggtgtcaa aaaccgcgtg gacgtggtta    3720
acatccctgc tgggaggatc agccgtaatt attataattg gcttggtgct ggctactatt    3780
gtggccatgt acgtgctgac caaccagaaa cataat                              3816
```

<210> SEQ ID NO 33
<211> LENGTH: 446
<212> TYPE: PRT
<213> ORGANISM: Artificial Sequence
<220> FEATURE:
<223> OTHER INFORMATION: Synthetic peptide

<400> SEQUENCE: 33

```
Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Thr Cys Thr His Pro
        115                 120                 125

Phe His His Glu Pro Pro Val Ile Gly Arg Glu Arg Phe His Ser Arg
    130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Ser Gly Gly
        195                 200                 205

Leu Asn Trp Tyr Arg Met Ser Pro Ser Asn Gln Thr Asp Lys Leu Ala
    210                 215                 220

Ala Phe Gly Gly Ser Asn Glu Gly Leu Thr Thr Thr Asp Lys Val Ile
225                 230                 235                 240

Asn Asn Cys Lys Ile Asp Gln Cys His Ala Ala Val Thr Asn His Lys
                245                 250                 255

Asn Trp Gln Tyr Asn Ser Pro Leu Val Pro Arg Asn Ala Glu Leu Gly
            260                 265                 270

Asp Arg Lys Gly Lys Ile His Ile Pro Phe Pro Leu Ala Asn Val Thr
        275                 280                 285

Cys Arg Val Pro Lys Ala Arg Asn Pro Thr Val Thr Tyr Gly Lys Asn
    290                 295                 300

Gln Val Thr Met Leu Leu Tyr Pro Asp His Pro Thr Leu Leu Ser Tyr
305                 310                 315                 320

Arg Asn Met Gly Gln Glu Pro Asn Tyr His Glu Glu Trp Val Thr His
```

```
            325                 330                 335
Lys Lys Glu Val Thr Leu Thr Val Pro Thr Glu Gly Leu Glu Val Thr
            340                 345                 350

Trp Gly Asn Asn Glu Pro Tyr Lys Tyr Trp Pro Gln Met Ser Thr Asn
            355                 360                 365

Gly Thr Ala His Gly His Pro His Glu Ile Ile Leu Tyr Tyr Tyr Glu
            370                 375                 380

Leu Tyr Pro Thr Met Thr Val Ile Val Ser Val Ala Ser Phe Val
385                 390                 395                 400

Leu Leu Ser Met Val Gly Thr Ala Val Gly Met Cys Val Cys Ala Arg
                405                 410                 415

Arg Arg Cys Ile Thr Pro Tyr Glu Leu Thr Pro Gly Ala Thr Val Pro
                420                 425                 430

Phe Leu Leu Ser Leu Leu Cys Cys Val Arg Thr Thr Lys Ala
                435                 440                 445

<210> SEQ ID NO 34
<211> LENGTH: 440
<212> TYPE: PRT
<213> ORGANISM: Artificial Sequence
<220> FEATURE:
<223> OTHER INFORMATION: Synthetic peptide

<400> SEQUENCE: 34

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Thr Cys Thr His Pro
        115                 120                 125

Phe His His Glu Pro Pro Val Ile Gly Arg Glu Arg Phe His Ser Arg
    130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Gly Ser Gly Gly
        195                 200                 205

Gly Ala Ile Ser Leu His Pro Lys Ala Lys Ile Glu Glu Ser Gly Ser
    210                 215                 220

Asn Glu Gly Leu Thr Thr Thr Asp Lys Val Ile Asn Asn Cys Lys Ile
225                 230                 235                 240

Asp Gln Cys His Ala Ala Val Thr Asn His Lys Asn Trp Gln Tyr Asn
```

```
                        245                 250                 255
Ser Pro Leu Val Pro Arg Asn Ala Glu Leu Gly Asp Arg Lys Gly Lys
            260                 265                 270

Ile His Ile Pro Phe Pro Leu Ala Asn Val Thr Cys Arg Val Pro Lys
            275                 280                 285

Ala Arg Asn Pro Thr Val Thr Tyr Gly Lys Asn Gln Val Thr Met Leu
            290                 295                 300

Leu Tyr Pro Asp His Pro Thr Leu Leu Ser Tyr Arg Asn Met Gly Gln
305                 310                 315                 320

Glu Pro Asn Tyr His Glu Glu Trp Val Thr His Lys Lys Glu Val Thr
                325                 330                 335

Leu Thr Val Pro Thr Glu Gly Leu Glu Val Thr Trp Gly Asn Asn Glu
            340                 345                 350

Pro Tyr Lys Tyr Trp Pro Gln Met Ser Thr Asn Gly Thr Ala His Gly
            355                 360                 365

His Pro His Glu Ile Ile Leu Tyr Tyr Glu Leu Tyr Pro Thr Met
            370                 375                 380

Thr Val Val Ile Val Ser Val Ala Ser Phe Val Leu Leu Ser Met Val
385                 390                 395                 400

Gly Thr Ala Val Gly Met Cys Val Cys Ala Arg Arg Cys Ile Thr
                405                 410                 415

Pro Tyr Glu Leu Thr Pro Gly Ala Thr Val Pro Phe Leu Leu Ser Leu
            420                 425                 430

Leu Cys Cys Val Arg Thr Thr Lys
            435                 440

<210> SEQ ID NO 35
<211> LENGTH: 443
<212> TYPE: PRT
<213> ORGANISM: Artificial Sequence
<220> FEATURE:
<223> OTHER INFORMATION: Synthetic peptide

<400> SEQUENCE: 35

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
                20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Thr Cys Thr His Pro
        115                 120                 125

Phe His His Glu Pro Pro Val Ile Gly Arg Glu Arg Phe His Ser Arg
    130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
```

```
                        165                 170                 175
Asp Arg Thr Leu Met Thr Gln Gln Ser Gly Asn Val Lys Ile Thr Val
                180                 185                 190

Asn Gly Gln Thr Val Arg Tyr Lys Cys Asn Cys Gly Ser Gly Gly
            195                 200                 205

Cys Gly Ala Ile Ser Leu His Pro Lys Ala Lys Ile Glu Glu Cys Gly
        210                 215                 220

Gly Ser Asn Glu Gly Leu Thr Thr Thr Asp Lys Val Ile Asn Cys
225                 230                 235                 240

Lys Ile Asp Gln Cys His Ala Ala Val Thr Asn His Lys Asn Trp Gln
                245                 250                 255

Tyr Asn Ser Pro Leu Val Pro Arg Asn Ala Glu Leu Gly Asp Arg Lys
                260                 265                 270

Gly Lys Ile His Ile Pro Phe Pro Leu Ala Asn Val Thr Cys Arg Val
                275                 280                 285

Pro Lys Ala Arg Asn Pro Thr Val Thr Tyr Gly Lys Asn Gln Val Thr
            290                 295                 300

Met Leu Leu Tyr Pro Asp His Pro Thr Leu Leu Ser Tyr Arg Asn Met
305                 310                 315                 320

Gly Gln Glu Pro Asn Tyr His Glu Glu Trp Val Thr His Lys Lys Glu
                325                 330                 335

Val Thr Leu Thr Val Pro Thr Gly Leu Glu Val Thr Trp Gly Asn
            340                 345                 350

Asn Glu Pro Tyr Lys Tyr Trp Pro Gln Met Ser Thr Asn Gly Thr Ala
                355                 360                 365

His Gly His Pro His Glu Ile Ile Leu Tyr Tyr Glu Leu Tyr Pro
        370                 375                 380

Thr Met Thr Val Val Ile Val Ser Val Ala Ser Phe Val Leu Leu Ser
385                 390                 395                 400

Met Val Gly Thr Ala Val Gly Met Cys Val Cys Ala Arg Arg Arg Cys
                405                 410                 415

Ile Thr Pro Tyr Glu Leu Thr Pro Gly Ala Thr Val Pro Phe Leu Leu
                420                 425                 430

Ser Leu Leu Cys Cys Val Arg Thr Thr Lys Ala
            435                 440

<210> SEQ ID NO 36
<211> LENGTH: 439
<212> TYPE: PRT
<213> ORGANISM: Artificial Sequence
<220> FEATURE:
<223> OTHER INFORMATION: Synthetic peptide

<400> SEQUENCE: 36

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Ile
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
```

```
                        85                  90                  95
Met Gly His Phe Ile Leu Ala Arg Cys Pro Lys Gly Glu Thr Leu Thr
                100                 105                 110

Val Gly Phe Thr Asp Ser Arg Lys Ile Ser His Thr Cys Thr His Pro
            115                 120                 125

Phe His His Glu Pro Pro Val Ile Gly Arg Glu Arg Phe His Ser Arg
        130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
                180                 185                 190

Asn Gly Gln Thr Val Arg Tyr Lys Cys Asn Cys Gly Gly Ser Gly Gly
            195                 200                 205

Cys Ile Ile Ser Tyr Gly Gly Ala Asp Tyr Cys Gly Gly Ser Asn Glu
        210                 215                 220

Gly Leu Thr Thr Thr Asp Lys Val Ile Asn Asn Cys Lys Ile Asp Gln
225                 230                 235                 240

Cys His Ala Ala Val Thr Asn His Lys Asn Trp Gln Tyr Asn Ser Pro
                245                 250                 255

Leu Val Pro Arg Asn Ala Glu Leu Gly Asp Arg Lys Gly Lys Ile His
                260                 265                 270

Ile Pro Phe Pro Leu Ala Asn Val Thr Cys Arg Val Pro Lys Ala Arg
            275                 280                 285

Asn Pro Thr Val Thr Tyr Gly Lys Asn Gln Val Thr Met Leu Leu Tyr
        290                 295                 300

Pro Asp His Pro Thr Leu Leu Ser Tyr Arg Asn Met Gly Gln Glu Pro
305                 310                 315                 320

Asn Tyr His Glu Glu Trp Val Thr His Lys Lys Glu Val Thr Leu Thr
                325                 330                 335

Val Pro Thr Glu Gly Leu Glu Val Thr Trp Gly Asn Asn Glu Pro Tyr
                340                 345                 350

Lys Tyr Trp Pro Gln Met Ser Thr Asn Gly Thr Ala His Gly His Pro
            355                 360                 365

His Glu Ile Ile Leu Tyr Tyr Tyr Glu Leu Tyr Pro Thr Met Thr Val
        370                 375                 380

Val Ile Val Ser Val Ala Ser Phe Val Leu Leu Ser Met Val Gly Thr
385                 390                 395                 400

Ala Val Gly Met Cys Val Cys Ala Arg Arg Arg Cys Ile Thr Pro Tyr
                405                 410                 415

Glu Leu Thr Pro Gly Ala Thr Val Pro Phe Leu Leu Ser Leu Leu Cys
                420                 425                 430

Cys Val Arg Thr Thr Lys Ala
            435

<210> SEQ ID NO 37
<211> LENGTH: 439
<212> TYPE: PRT
<213> ORGANISM: Chikungunya virus

<400> SEQUENCE: 37

Tyr Glu His Val Thr Val Ile Pro Asn Thr Val Gly Val Pro Tyr Lys
1               5                   10                  15
```

-continued

```
Thr Leu Val Asn Arg Pro Gly Tyr Ser Pro Met Val Leu Glu Met Glu
             20                  25                  30

Leu Gln Ser Val Thr Leu Glu Pro Thr Leu Ser Leu Asp Tyr Ile Thr
         35                  40                  45

Cys Glu Tyr Lys Thr Val Ile Pro Ser Pro Tyr Val Lys Cys Cys Gly
50                   55                  60

Thr Ala Glu Cys Lys Asp Lys Ser Leu Pro Asp Tyr Ser Cys Lys Val
65                   70                  75                  80

Phe Thr Gly Val Tyr Pro Phe Met Trp Gly Gly Ala Tyr Cys Phe Cys
                 85                  90                  95

Asp Ala Glu Asn Thr Gln Leu Ser Glu Ala His Val Glu Lys Ser Glu
                100                 105                 110

Ser Cys Lys Thr Glu Phe Ala Ser Ala Tyr Arg Ala His Thr Ala Ser
            115                 120                 125

Ala Ser Ala Lys Leu Arg Val Leu Tyr Gln Gly Asn Asn Ile Thr Val
        130                 135                 140

Ala Ala Tyr Ala Asn Gly Asp His Ala Val Thr Val Lys Asp Ala Lys
145                 150                 155                 160

Phe Val Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
                180                 185                 190

Gly Ala Gly Arg Pro Gly Gln Phe Gly Asp Ile Gln Ser Arg Thr Pro
            195                 200                 205

Glu Ser Lys Asp Val Tyr Ala Asn Thr Gln Leu Val Leu Gln Arg Pro
210                 215                 220

Ala Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
            260                 265                 270

Val Gly Asn Ile Pro Ile Ser Ile Asp Ile Pro Asp Ala Ala Phe Thr
        275                 280                 285

Arg Val Val Asp Ala Pro Ser Val Thr Asp Met Ser Cys Glu Val Pro
290                 295                 300

Ala Cys Thr His Ser Ser Asp Phe Gly Gly Val Ala Ile Ile Lys Tyr
305                 310                 315                 320

Thr Ala Ser Lys Lys Gly Lys Cys Ala Val His Ser Met Thr Asn Ala
                325                 330                 335

Val Thr Ile Arg Glu Ala Asp Val Glu Val Glu Gly Asn Ser Gln Leu
            340                 345                 350

Gln Ile Ser Phe Ser Thr Ala Leu Ala Ser Ala Glu Phe Arg Val Gln
        355                 360                 365

Val Cys Ser Thr Gln Val His Cys Ala Ala Ala Cys His Pro Pro Lys
370                 375                 380

Asp His Ile Val Asn Tyr Pro Ala Ser His Thr Thr Leu Gly Val Gln
385                 390                 395                 400

Asp Ile Ser Thr Thr Ala Met Ser Trp Val Gln Lys Ile Thr Gly Gly
                405                 410                 415

Val Gly Leu Ile Val Ala Val Ala Ala Leu Ile Leu Ile Val Val Leu
            420                 425                 430

Cys Val Ser Phe Ser Arg His
```

<210> SEQ ID NO 38
<211> LENGTH: 261
<212> TYPE: PRT
<213> ORGANISM: Chikungunya virus

<400> SEQUENCE: 38

Met Glu Phe Ile Pro Thr Gln Thr Phe Tyr Asn Arg Arg Tyr Gln Pro
1 5 10 15

Arg Pro Trp Ala Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn
50 55 60

Arg Lys Asn Lys Lys Gln Arg Gln Lys Lys Gln Ala Pro Gln Asn Asp
65 70 75 80

Pro Lys Gln Lys Lys Gln Pro Pro Gln Lys Lys Pro Ala Gln Lys Lys
85 90 95

Lys Lys Pro Gly Arg Arg Glu Arg Met Cys Met Lys Ile Glu Asn Asp
100 105 110

Cys Ile Phe Glu Val Lys His Glu Gly Lys Val Met Gly Tyr Ala Cys
115 120 125

Leu Val Gly Asp Lys Val Met Lys Pro Ala His Val Lys Gly Thr Ile
130 135 140

Asp Asn Ala Asp Leu Ala Lys Leu Ala Phe Lys Arg Ser Ser Lys Tyr
145 150 155 160

Asp Leu Glu Cys Ala Gln Ile Pro Val His Met Lys Ser Asp Ala Ser
165 170 175

Lys Phe Thr His Glu Lys Pro Glu Gly Tyr Tyr Asn Trp His His Gly
180 185 190

Ala Val Gln Tyr Ser Gly Gly Arg Phe Thr Ile Pro Thr Gly Ala Gly
195 200 205

Lys Pro Gly Asp Ser Gly Arg Pro Ile Phe Asp Asn Lys Gly Arg Val
210 215 220

Val Ala Ile Val Leu Gly Gly Ala Asn Glu Gly Ala Arg Thr Ala Leu
225 230 235 240

Ser Val Val Thr Trp Asn Lys Asp Ile Val Thr Lys Ile Thr Pro Glu
245 250 255

Gly Ala Glu Glu Trp
260

<210> SEQ ID NO 39
<211> LENGTH: 447
<212> TYPE: PRT
<213> ORGANISM: Artificial Sequence
<220> FEATURE:
<223> OTHER INFORMATION: Synthetic peptide

<400> SEQUENCE: 39

Ser Thr Glu Glu Leu Phe Asn Glu Tyr Lys Leu Thr Arg Pro Tyr Met
1 5 10 15

Ala Arg Cys Ile Arg Cys Ala Val Gly Ser Cys His Ser Pro Ile Ala
20 25 30

Ile Glu Ala Val Lys Ser Asp Gly His Asp Gly Tyr Val Arg Leu Gln
35 40 45

Thr Ser Ser Gln Tyr Gly Leu Asp Ser Ser Gly Asn Leu Lys Gly Arg
50                  55                  60

Thr Met Arg Tyr Asp Met His Gly Thr Ile Lys Glu Ile Pro Leu His
65                  70                  75                  80

Gln Val Ser Leu Tyr Thr Ser Arg Pro Cys His Ile Val Asp Gly His
                85                  90                  95

Gly Tyr Phe Leu Leu Ala Arg Cys Pro Ala Gly Asp Ser Ile Thr Met
                100                 105                 110

Glu Phe Lys Lys Asp Ser Val Arg His Ser Cys Ser Val Pro Tyr Glu
            115                 120                 125

Val Lys Phe Asn Pro Val Gly Arg Glu Leu Tyr Thr His Pro Pro Glu
130                 135                 140

His Gly Val Glu Gln Ala Cys Gln Val Tyr Ala His Asp Ala Gln Asn
145                 150                 155                 160

Arg Gly Ala Tyr Val Glu Met His Leu Pro Gly Ser Glu Val Asp Ser
                165                 170                 175

Ser Leu Val Ser Leu Ser Gly Ser Gly Gly Leu Asn Trp Tyr Arg
                180                 185                 190

Met Ser Pro Ser Asn Gln Thr Asp Lys Leu Ala Ala Phe Gly Gly Ser
            195                 200                 205

Ser Val Thr Val Thr Pro Pro Asp Gly Thr Ser Ala Leu Val Glu Cys
210                 215                 220

Glu Cys Gly Gly Thr Lys Ile Ser Glu Thr Ile Asn Lys Thr Lys Gln
225                 230                 235                 240

Phe Ser Gln Cys Thr Lys Lys Glu Gln Cys Arg Ala Tyr Arg Leu Gln
                245                 250                 255

Asn Asp Lys Trp Val Tyr Asn Ser Asp Lys Leu Pro Lys Ala Ala Gly
            260                 265                 270

Ala Thr Leu Lys Gly Lys Leu His Val Pro Phe Leu Leu Ala Asp Gly
        275                 280                 285

Lys Cys Thr Val Pro Leu Ala Pro Glu Pro Met Ile Thr Phe Gly Phe
290                 295                 300

Arg Ser Val Ser Leu Lys Leu His Pro Lys Asn Pro Thr Tyr Leu Ile
305                 310                 315                 320

Thr Arg Gln Leu Ala Asp Glu Pro His Tyr Thr His Glu Leu Ile Ser
                325                 330                 335

Glu Pro Ala Val Arg Asn Phe Thr Val Thr Glu Lys Gly Trp Glu Phe
            340                 345                 350

Val Trp Gly Asn His Pro Pro Lys Arg Phe Trp Ala Gln Glu Thr Ala
        355                 360                 365

Pro Gly Asn Pro His Gly Leu Pro His Glu Val Ile Thr His Tyr Tyr
370                 375                 380

His Arg Tyr Pro Met Ser Thr Ile Leu Gly Leu Ser Ile Cys Ala Ala
385                 390                 395                 400

Ile Ala Thr Val Ser Val Ala Ala Ser Thr Trp Leu Phe Cys Arg Ser
                405                 410                 415

Arg Val Ala Cys Leu Thr Pro Tyr Arg Leu Thr Pro Asn Ala Arg Ile
            420                 425                 430

Pro Phe Cys Leu Ala Val Leu Cys Cys Ala Arg Thr Ala Arg Ala
        435                 440                 445

<210> SEQ ID NO 40
<211> LENGTH: 442

```
<212> TYPE: PRT
<213> ORGANISM: Artificial Sequence
<220> FEATURE:
<223> OTHER INFORMATION: Synthetic peptide

<400> SEQUENCE: 40
```

| | | | | | | | | | | | | | | |
|---|---|---|---|---|---|---|---|---|---|---|---|---|---|---|
| Ser | Thr | Glu | Glu | Leu | Phe | Asn | Glu | Tyr | Lys | Leu | Thr | Arg | Pro | Tyr | Met |
| 1 | | | | 5 | | | | | 10 | | | | | 15 |
| Ala | Arg | Cys | Ile | Arg | Cys | Ala | Val | Gly | Ser | Cys | His | Ser | Pro | Ile | Ala |
| | | | 20 | | | | | 25 | | | | | 30 | | |
| Ile | Glu | Ala | Val | Lys | Ser | Asp | Gly | His | Asp | Gly | Tyr | Val | Arg | Leu | Gln |
| | | | 35 | | | | | 40 | | | | | 45 | | |
| Thr | Ser | Ser | Gln | Tyr | Gly | Leu | Asp | Ser | Ser | Gly | Asn | Leu | Lys | Gly | Arg |
| | 50 | | | | | 55 | | | | | 60 | | | | |
| Thr | Met | Arg | Tyr | Asp | Met | His | Gly | Thr | Ile | Lys | Glu | Ile | Pro | Leu | His |
| 65 | | | | | 70 | | | | | 75 | | | | | 80 |
| Gln | Val | Ser | Leu | Tyr | Thr | Ser | Arg | Pro | Cys | His | Ile | Val | Asp | Gly | His |
| | | | | 85 | | | | | 90 | | | | | 95 | |
| Gly | Tyr | Phe | Leu | Leu | Ala | Arg | Cys | Pro | Ala | Gly | Asp | Ser | Ile | Thr | Met |
| | | | 100 | | | | | 105 | | | | | 110 | | |
| Glu | Phe | Lys | Lys | Asp | Ser | Val | Arg | His | Ser | Cys | Ser | Val | Pro | Tyr | Glu |
| | | | 115 | | | | | 120 | | | | | 125 | | |
| Val | Lys | Phe | Asn | Pro | Val | Gly | Arg | Glu | Leu | Tyr | Thr | His | Pro | Pro | Glu |
| | 130 | | | | | 135 | | | | | 140 | | | | |
| His | Gly | Val | Glu | Gln | Ala | Cys | Gln | Val | Tyr | Ala | His | Asp | Ala | Gln | Asn |
| 145 | | | | | 150 | | | | | 155 | | | | | 160 |
| Arg | Gly | Ala | Tyr | Val | Glu | Met | His | Leu | Pro | Gly | Ser | Glu | Val | Asp | Ser |
| | | | | 165 | | | | | 170 | | | | | 175 | |
| Ser | Leu | Val | Ser | Leu | Ser | Gly | Ser | Gly | Gly | Gly | Ala | Ile | Ser | Leu |
| | | | 180 | | | | | 185 | | | | | 190 | | |
| His | Pro | Lys | Ala | Lys | Ile | Glu | Glu | Ser | Gly | Ser | Ser | Val | Thr | Val | Thr |
| | | | 195 | | | | | 200 | | | | | 205 | | |
| Pro | Pro | Asp | Gly | Thr | Ser | Ala | Leu | Val | Glu | Cys | Glu | Cys | Gly | Gly | Thr |
| | 210 | | | | | 215 | | | | | 220 | | | | |
| Lys | Ile | Ser | Glu | Thr | Ile | Asn | Lys | Thr | Lys | Gln | Phe | Ser | Gln | Cys | Thr |
| 225 | | | | | 230 | | | | | 235 | | | | | 240 |
| Lys | Lys | Glu | Gln | Cys | Arg | Ala | Tyr | Arg | Leu | Gln | Asn | Asp | Lys | Trp | Val |
| | | | | 245 | | | | | 250 | | | | | 255 | |
| Tyr | Asn | Ser | Asp | Lys | Leu | Pro | Lys | Ala | Ala | Gly | Ala | Thr | Leu | Lys | Gly |
| | | | 260 | | | | | 265 | | | | | 270 | | |
| Lys | Leu | His | Val | Pro | Phe | Leu | Leu | Ala | Asp | Gly | Lys | Cys | Thr | Val | Pro |
| | | | 275 | | | | | 280 | | | | | 285 | | |
| Leu | Ala | Pro | Glu | Pro | Met | Ile | Thr | Phe | Gly | Phe | Arg | Ser | Val | Ser | Leu |
| | 290 | | | | | 295 | | | | | 300 | | | | |
| Lys | Leu | His | Pro | Lys | Asn | Pro | Thr | Tyr | Leu | Ile | Thr | Arg | Gln | Leu | Ala |
| 305 | | | | | 310 | | | | | 315 | | | | | 320 |
| Asp | Glu | Pro | His | Tyr | Thr | His | Glu | Leu | Ile | Ser | Glu | Pro | Ala | Val | Arg |
| | | | | 325 | | | | | 330 | | | | | 335 | |
| Asn | Phe | Thr | Val | Thr | Glu | Lys | Gly | Trp | Glu | Phe | Val | Trp | Gly | Asn | His |
| | | | 340 | | | | | 345 | | | | | 350 | | |
| Pro | Pro | Lys | Arg | Phe | Trp | Ala | Gln | Glu | Thr | Ala | Pro | Gly | Asn | Pro | His |
| | | | 355 | | | | | 360 | | | | | 365 | | |
| Gly | Leu | Pro | His | Glu | Val | Ile | Thr | His | Tyr | Tyr | His | Arg | Tyr | Pro | Met |
| | 370 | | | | | 375 | | | | | 380 | | | | |

```
Ser Thr Ile Leu Gly Leu Ser Ile Cys Ala Ala Ile Ala Thr Val Ser
385                 390                 395                 400

Val Ala Ala Ser Thr Trp Leu Phe Cys Arg Ser Arg Val Ala Cys Leu
            405                 410                 415

Thr Pro Tyr Arg Leu Thr Pro Asn Ala Arg Ile Pro Phe Cys Leu Ala
        420                 425                 430

Val Leu Cys Cys Ala Arg Thr Ala Arg Ala
        435                 440
```

<210> SEQ ID NO 41
<211> LENGTH: 444
<212> TYPE: PRT
<213> ORGANISM: Artificial Sequence
<220> FEATURE:
<223> OTHER INFORMATION: Synthetic peptide

<400> SEQUENCE: 41

```
Ser Thr Glu Glu Leu Phe Asn Glu Tyr Lys Leu Thr Arg Pro Tyr Met
1               5                   10                  15

Ala Arg Cys Ile Arg Cys Ala Val Gly Ser Cys His Ser Pro Ile Ala
            20                  25                  30

Ile Glu Ala Val Lys Ser Asp Gly His Asp Gly Tyr Val Arg Leu Gln
        35                  40                  45

Thr Ser Ser Gln Tyr Gly Leu Asp Ser Ser Gly Asn Leu Lys Gly Arg
50                  55                  60

Thr Met Arg Tyr Asp Met His Gly Thr Ile Lys Glu Ile Pro Leu His
65                  70                  75                  80

Gln Val Ser Leu Tyr Thr Ser Arg Pro Cys His Ile Val Asp Gly His
            85                  90                  95

Gly Tyr Phe Leu Leu Ala Arg Cys Pro Ala Gly Asp Ser Ile Thr Met
        100                 105                 110

Glu Phe Lys Lys Asp Ser Val Arg His Ser Cys Ser Val Pro Tyr Glu
    115                 120                 125

Val Lys Phe Asn Pro Val Gly Arg Glu Leu Tyr Thr His Pro Pro Glu
130                 135                 140

His Gly Val Glu Gln Ala Cys Gln Val Tyr Ala His Asp Ala Gln Asn
145                 150                 155                 160

Arg Gly Ala Tyr Val Glu Met His Leu Pro Gly Ser Glu Val Asp Ser
            165                 170                 175

Ser Leu Val Ser Leu Ser Gly Ser Gly Cys Gly Ala Ile Ser
        180                 185                 190

Leu His Pro Lys Ala Lys Ile Glu Glu Cys Gly Gly Ser Ser Val Thr
    195                 200                 205

Val Thr Pro Pro Asp Gly Thr Ser Ala Leu Val Glu Cys Glu Cys Gly
210                 215                 220

Gly Thr Lys Ile Ser Glu Thr Ile Asn Lys Thr Lys Gln Phe Ser Gln
225                 230                 235                 240

Cys Thr Lys Lys Glu Gln Cys Arg Ala Tyr Arg Leu Gln Asn Asp Lys
            245                 250                 255

Trp Val Tyr Asn Ser Asp Lys Leu Pro Lys Ala Ala Gly Ala Thr Leu
        260                 265                 270

Lys Gly Lys Leu His Val Pro Phe Leu Leu Ala Asp Gly Lys Cys Thr
    275                 280                 285

Val Pro Leu Ala Pro Glu Pro Met Ile Thr Phe Gly Phe Arg Ser Val
290                 295                 300
```

Ser Leu Lys Leu His Pro Lys Asn Pro Thr Tyr Leu Ile Thr Arg Gln
305                 310                 315                 320

Leu Ala Asp Glu Pro His Tyr Thr His Glu Leu Ile Ser Glu Pro Ala
            325                 330                 335

Val Arg Asn Phe Thr Val Thr Glu Lys Gly Trp Glu Phe Val Trp Gly
            340                 345                 350

Asn His Pro Pro Lys Arg Phe Trp Ala Gln Glu Thr Ala Pro Gly Asn
            355                 360                 365

Pro His Gly Leu Pro His Glu Val Ile Thr His Tyr Tyr His Arg Tyr
370                 375                 380

Pro Met Ser Thr Ile Leu Gly Leu Ser Ile Cys Ala Ala Ile Ala Thr
385                 390                 395                 400

Val Ser Val Ala Ala Ser Thr Trp Leu Phe Cys Arg Ser Arg Val Ala
            405                 410                 415

Cys Leu Thr Pro Tyr Arg Leu Thr Pro Asn Ala Arg Ile Pro Phe Cys
            420                 425                 430

Leu Ala Val Leu Cys Cys Ala Arg Thr Ala Arg Ala
            435                 440

<210> SEQ ID NO 42
<211> LENGTH: 440
<212> TYPE: PRT
<213> ORGANISM: Artificial Sequence
<220> FEATURE:
<223> OTHER INFORMATION: Synthetic peptide

<400> SEQUENCE: 42

Ser Thr Glu Glu Leu Phe Asn Glu Tyr Lys Leu Thr Arg Pro Tyr Met
1               5                   10                  15

Ala Arg Cys Ile Arg Cys Ala Val Gly Ser Cys His Ser Pro Ile Ala
            20                  25                  30

Ile Glu Ala Val Lys Ser Asp Gly His Asp Gly Tyr Val Arg Leu Gln
            35                  40                  45

Thr Ser Ser Gln Tyr Gly Leu Asp Ser Ser Gly Asn Leu Lys Gly Arg
    50                  55                  60

Thr Met Arg Tyr Asp Met His Gly Thr Ile Lys Glu Ile Pro Leu His
65                  70                  75                  80

Gln Val Ser Leu Tyr Thr Ser Arg Pro Cys His Ile Val Asp Gly His
                85                  90                  95

Gly Tyr Phe Leu Leu Ala Arg Cys Pro Ala Gly Asp Ser Ile Thr Met
            100                 105                 110

Glu Phe Lys Lys Asp Ser Val Arg His Ser Cys Ser Val Pro Tyr Glu
        115                 120                 125

Val Lys Phe Asn Pro Val Gly Arg Glu Leu Tyr Thr His Pro Pro Glu
    130                 135                 140

His Gly Val Glu Gln Ala Cys Gln Val Tyr Ala His Asp Ala Gln Asn
145                 150                 155                 160

Arg Gly Ala Tyr Val Glu Met His Leu Pro Gly Ser Glu Val Asp Ser
                165                 170                 175

Ser Leu Val Ser Leu Ser Gly Ser Gly Gly Cys Ile Ile Ser Tyr
            180                 185                 190

Gly Gly Ala Asp Tyr Cys Gly Gly Ser Ser Val Thr Val Thr Pro Pro
            195                 200                 205

Asp Gly Thr Ser Ala Leu Val Glu Cys Glu Cys Gly Gly Thr Lys Ile
    210                 215                 220

Ser Glu Thr Ile Asn Lys Thr Lys Gln Phe Ser Gln Cys Thr Lys Lys
225                 230                 235                 240

Glu Gln Cys Arg Ala Tyr Arg Leu Gln Asn Asp Lys Trp Val Tyr Asn
            245                 250                 255

Ser Asp Lys Leu Pro Lys Ala Gly Ala Thr Leu Lys Gly Lys Leu
        260                 265                 270

His Val Pro Phe Leu Leu Ala Asp Gly Lys Cys Thr Val Pro Leu Ala
        275                 280                 285

Pro Glu Pro Met Ile Thr Phe Gly Phe Arg Ser Val Ser Leu Lys Leu
        290                 295                 300

His Pro Lys Asn Pro Thr Tyr Leu Ile Thr Arg Gln Leu Ala Asp Glu
305                 310                 315                 320

Pro His Tyr Thr His Glu Leu Ile Ser Glu Pro Ala Val Arg Asn Phe
                325                 330                 335

Thr Val Thr Glu Lys Gly Trp Glu Phe Val Trp Gly Asn His Pro Pro
                340                 345                 350

Lys Arg Phe Trp Ala Gln Glu Thr Ala Pro Gly Asn Pro His Gly Leu
            355                 360                 365

Pro His Glu Val Ile Thr His Tyr Tyr His Arg Tyr Pro Met Ser Thr
370                 375                 380

Ile Leu Gly Leu Ser Ile Cys Ala Ala Ile Ala Thr Val Ser Val Ala
385                 390                 395                 400

Ala Ser Thr Trp Leu Phe Cys Arg Ser Arg Val Ala Cys Leu Thr Pro
            405                 410                 415

Tyr Arg Leu Thr Pro Asn Ala Arg Ile Pro Phe Cys Leu Ala Val Leu
        420                 425                 430

Cys Cys Ala Arg Thr Ala Arg Ala
        435                 440

<210> SEQ ID NO 43
<211> LENGTH: 442
<212> TYPE: PRT
<213> ORGANISM: Venezuelan equine encephalitis virus

<400> SEQUENCE: 43

Tyr Glu His Ala Thr Thr Met Pro Ser Gln Ala Gly Ile Ser Tyr Asn
1               5                   10                  15

Thr Ile Val Asn Arg Ala Gly Tyr Ala Pro Leu Pro Ile Ser Ile Thr
            20                  25                  30

Pro Thr Lys Ile Lys Leu Ile Pro Thr Val Asn Leu Glu Tyr Val Thr
        35                  40                  45

Cys His Tyr Lys Thr Gly Met Asp Ser Pro Ala Ile Lys Cys Cys Gly
    50                  55                  60

Ser Gln Glu Cys Thr Pro Thr Tyr Arg Pro Asp Glu Gln Cys Lys Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Val Ser Lys Ala Tyr Val Met Lys Ser Asp
            100                 105                 110

Asp Cys Leu Ala Asp His Ala Glu Ala Tyr Lys Ala His Thr Ala Ser
        115                 120                 125

Val Gln Ala Phe Leu Asn Ile Thr Val Gly Glu His Ser Ile Val Thr
    130                 135                 140

Thr Val Tyr Val Asn Gly Glu Thr Pro Val Asn Phe Asn Gly Val Lys
145                 150                 155                 160

```
Ile Thr Ala Gly Pro Leu Ser Thr Ala Trp Thr Pro Phe Asp Arg Lys
                165                 170                 175
Ile Val Gln Tyr Ala Gly Glu Ile Tyr Asn Tyr Asp Phe Pro Glu Tyr
            180                 185                 190
Gly Ala Gly Gln Pro Gly Ala Phe Gly Asp Ile Gln Ser Arg Thr Val
        195                 200                 205
Ser Ser Ser Asp Leu Tyr Ala Asn Thr Asn Leu Val Leu Gln Arg Pro
    210                 215                 220
Lys Ala Gly Ala Ile His Val Pro Tyr Thr Gln Ala Pro Ser Gly Phe
225                 230                 235                 240
Glu Gln Trp Lys Lys Asp Lys Ala Pro Ser Leu Lys Phe Thr Ala Pro
                245                 250                 255
Phe Gly Cys Glu Ile Tyr Thr Asn Pro Ile Arg Ala Glu Asn Cys Ala
            260                 265                 270
Val Gly Ser Ile Pro Leu Ala Phe Asp Ile Pro Asp Ala Leu Phe Thr
        275                 280                 285
Arg Val Ser Glu Thr Pro Thr Leu Ser Ala Ala Glu Cys Thr Leu Asn
    290                 295                 300
Glu Cys Val Tyr Ser Ser Asp Phe Gly Gly Ile Ala Thr Val Lys Tyr
305                 310                 315                 320
Ser Ala Ser Lys Ser Gly Lys Cys Ala Val His Val Pro Ser Gly Thr
                325                 330                 335
Ala Thr Leu Lys Glu Ala Ala Val Glu Leu Thr Glu Gln Gly Ser Ala
            340                 345                 350
Thr Ile His Phe Ser Thr Ala Asn Ile His Pro Glu Phe Arg Leu Gln
        355                 360                 365
Ile Cys Thr Ser Tyr Val Thr Cys Lys Gly Asp Cys His Pro Pro Lys
    370                 375                 380
Asp His Ile Val Thr His Pro Gln Tyr His Ala Gln Thr Phe Thr Ala
385                 390                 395                 400
Ala Val Ser Lys Thr Ala Trp Thr Trp Leu Thr Ser Leu Leu Gly Gly
                405                 410                 415
Ser Ala Val Ile Ile Ile Gly Leu Val Leu Ala Thr Ile Val Ala
            420                 425                 430
Met Tyr Val Leu Thr Asn Gln Lys His Asn
        435                 440

<210> SEQ ID NO 44
<211> LENGTH: 275
<212> TYPE: PRT
<213> ORGANISM: Venezuelan equine encephalitis virus

<400> SEQUENCE: 44

Met Phe Pro Phe Gln Pro Met Tyr Pro Met Gln Pro Met Pro Tyr Arg
1               5                   10                  15
Asn Pro Phe Ala Ala Pro Arg Arg Pro Trp Phe Pro Arg Thr Asp Pro
            20                  25                  30
Phe Leu Ala Met Gln Val Gln Glu Leu Thr Arg Ser Met Ala Asn Leu
        35                  40                  45
Thr Phe Lys Gln Arg Arg Asp Ala Pro Pro Glu Gly Pro Ser Ala Asn
    50                  55                  60
Lys Pro Lys Lys Glu Ala Ser Gln Lys Gln Lys Gly Gly Gly Gln Gly
65                  70                  75                  80
Lys Lys Lys Lys Asn Gln Gly Lys Lys Lys Ala Lys Thr Gly Pro Pro
```

```
                     85                  90                  95
Asn Pro Lys Ala Gln Asn Gly Asn Lys Lys Thr Asn Lys Pro
            100                 105                 110
Gly Lys Arg Gln Arg Met Val Met Lys Leu Glu Ser Asp Lys Thr Phe
            115                 120                 125
Pro Ile Met Leu Glu Gly Lys Ile Asn Gly Tyr Ala Cys Val Val Gly
            130                 135                 140
Gly Lys Leu Phe Arg Pro Met His Val Glu Gly Lys Ile Asp Asn Asp
145                 150                 155                 160
Val Leu Ala Ala Leu Lys Thr Lys Lys Ala Ser Lys Tyr Asp Leu Glu
                    165                 170                 175
Tyr Ala Asp Val Pro Gln Asn Met Arg Ala Asp Thr Phe Lys Tyr Thr
                    180                 185                 190
His Glu Lys Pro Gln Gly Tyr Tyr Ser Trp His His Gly Ala Val Gln
                    195                 200                 205
Tyr Glu Asn Gly Arg Phe Thr Val Pro Lys Gly Val Gly Ala Lys Gly
            210                 215                 220
Asp Ser Gly Arg Pro Ile Leu Asp Asn Gln Gly Arg Val Val Ala Ile
225                 230                 235                 240
Val Leu Gly Gly Val Asn Glu Gly Ser Arg Thr Ala Leu Ser Val Val
                    245                 250                 255
Met Trp Asn Glu Lys Gly Val Thr Val Lys Tyr Thr Pro Glu Asn Cys
            260                 265                 270
Glu Gln Trp
        275

<210> SEQ ID NO 45
<211> LENGTH: 8467
<212> TYPE: DNA
<213> ORGANISM: Artificial Sequence
<220> FEATURE:
<223> OTHER INFORMATION: Synthetic polynucleotide

<400> SEQUENCE: 45
gaattcccat tgcatacgtt gtatccatat cataatatgt acatttatat tggctcatgt    60
ccaacattac cgccatgttg acattgatta ttgactagtt attaatagta atcaattacg   120
gggtcattag ttcatagccc atatatggag ttccgcgtta cataacttac ggtaaatggc   180
ccgcctggct gaccgcccaa cgacccccgc ccattgacgt caataatgac gtatgttccc   240
atagtaacgc caatagggac tttccattga cgtcaatggg tggagtattt acggtaaact   300
gcccacttgg cagtacatca agtgtatcat atgccaagta cgccccctat tgacgtcaat   360
gacggtaaat ggcccgcctg gcattatgcc cagtacatga ccttatggga ctttcctact   420
tggcagtaca tctacgtatt agtcatcgct attaccatgg tgatgcggtt ttggcagtac   480
atcaatgggc gtggatagcg gtttgactca cggggatttc caagtctcca ccccattgac   540
gtcaatggga gtttgttttg gcaccaaaat caacgggact ttccaaaatg tcgtaacaac   600
tccgccccat tgacgcaaat gggcggtagg cgtgtacggt gggaggtcta taagcagag   660
gctcgtttag tgaaccgtca gatcgcctgg agacgccatc cacgctgttt tgacctccat   720
agaagacacc gggaccgatc cagcctccgt taacggtgga gggcagtgta gtctgagcag   780
tactcgttgc tgccgcgcgc gccaccagac ataatagctg acagactaac agactgttcc   840
tttccatggg tcttttctgc agtcaccgtc gtcgacacgt gtgatcagat atcgcggccg   900
ccaccatgga gttcatcccg acgcaaactt tctataacag aaggtaccaa ccccgaccct   960
```

```
gggcccacg ccctacaatt caagtaatta gacctagacc acgtccacag aggcaggctg    1020
ggcaactcgc ccagctgatc tccgcagtca acaaattgac catgcgcgcg gtacctcaac    1080
agaagcctcg cagaaatcgg aaaaacaaga agcaaaggca gaagaagcag gcgccgcaaa    1140
acgacccaaa gcaaaagaag caaccaccac aaaagaagcc ggctcaaaag aagaagaaac    1200
caggccgtag ggagagaatg tgcatgaaaa ttgaaaatga ttgcatcttc gaagtcaagc    1260
atgaaggcaa agtgatgggc tacgcatgcc tggtggggga taaagtaatg aaaccagcac    1320
atgtgaaggg aactatcgac aatgccgatc tggctaaact ggcctttaag cggtcgtcta    1380
aatacgatct tgaatgtgca cagataccgg tgcacatgaa gtctgatgcc tcgaagttta    1440
cccacgagaa acccgagggg tactataact ggcatcacgg agcagtgcag tattcaggag    1500
gccggttcac tatcccgacg ggtgcaggca agccgggaga cagcggcaga ccgatcttcg    1560
acaacaaagg acgggtggtg gccatcgtcc taggaggggc caacgaaggt gcccgcacgg    1620
ccctctccgt ggtgacgtgg aacaaagaca tcgtcacaaa aattacccct gagggagccg    1680
aagagtggag cctcgccctc ccggtcttgt gcctgttggc aaacactaca ttcccctgct    1740
ctcagccgcc ttgcacaccc tgctgctacg aaaaggaacc ggaaagcacc ttgcgcatgc    1800
ttgaggacaa cgtgatgaga cccggatact accagctact aaaagcatcg ctgacttgct    1860
ctccccaccg ccaaagacgc agtactaagg acaattttaa tgtctataaa gccacaagac    1920
catatctagc tcattgtcct gactgcggag aagggcattc gtgccacagc cctatcgcat    1980
tggagcgcat cagaaatgaa gcaacggacg gaacgctgaa aatccaggtc tctttgcaga    2040
tcgggataaa gacagatgac agccacgatt ggaccaagct gcgctatatg gatagccata    2100
cgccagcgga cgcggagcga gccggattgc ttgtaaggac ttcagcaccg tgcacgatca    2160
ccgggaccat gggacacttt attctcgccc gatgcccgaa aggagagacg ctgacagtgg    2220
gatttacgga cagcagaaag atcagccaca catgcacaca cccgttccat catgaaccac    2280
ctgtgatagg tagggagagg ttccactctc gaccacaaca tggtaaagag ttaccttgca    2340
gcacgtacgt gcagagcacc gctgccactg ctgaggagat agaggtgcat atgcccccag    2400
atactcctga ccgcacgctg atgacgcagc agtctggcaa cgtgaagatc acagttaatg    2460
ggcagacggt gcggtacaag tgcaactgcg gtggctccgg aggactaaac tggtaccgca    2520
tgagccccag caaccagacg gacaagctgg ccgccttcgg aggatccaac gagggactga    2580
caaccacaga caaagtgatc aataactgca aaattgatca gtgccatgct gcagtcacta    2640
atcacaagaa ttggcaatac aactcccctt agtcccgcg caacgctgaa ctcggggacc    2700
gtaaaggaaa gatccacatc ccattcccat ggcaaacgt gacttgcaga gtgccaaaag    2760
caagaaaccc tacagtaact tacgaaaaa accaagtcac catgctgctg tatcctgacc    2820
atccgacact cttgtcttac cgtaacatgg gacaggaacc aaattaccac gaggagtggg    2880
tgacacacaa gaaggaggtt accttgaccg tgcctactga gggtctggag gtcacttggg    2940
gcaacaacga accatacaag tactggccgc agatgtctac gaacggtact gctcatggtc    3000
acccacatga gataatcttg tactattatg agctgtaccc cactatgact gtagtcattg    3060
tgtcggtggc ctcgttcgtg cttctgtcga tggtgggcac agcagtggga atgtgtgtgt    3120
gcgcacggcg cagatgcatt acaccatatg aattaacacc aggagccact gttcccttcc    3180
tgctcagcct gctatgctgc gtcagaacga ccaaggcggc cacatattac gaggctgcg    3240 catatctatg gaacgaacag cagccctgt tctggttgca ggctcttatc ccgctggccg    3300
```

```
ccttgatcgt cctgtgcaac tgtctgaaac tcttgccatg ctgctgtaag accctggctt    3360
ttttagccgt aatgagcatc ggtgcccaca ctgtgagcgc gtacgaacac gtaacagtga    3420
tcccgaacac ggtgggagta ccgtataaga ctcttgtcaa cagaccgggt tacagcccca    3480
tggtgttgga gatggagcta caatcagtca ccttggaacc aacactgtca cttgactaca    3540
tcacgtgcga gtacaaaact gtcatcccct ccccgtacgt gaagtgctgt ggtacagcag    3600
agtgcaagga caagagccta ccagactaca gctgcaaggt cttactgga gtctacccat     3660 ttatgtgggg cggcgcctac tgcttttgcg acgccgaaaa tacgcaattg agcgaggcac    3720
atgtagagaa atctgaatct tgcaaaacag agtttgcatc ggcctacaga gcccacaccg    3780
catcggcgtc ggcgaagctc cgcgtccttt accaaggaaa caacattacc gtagctgcct    3840
acgctaacgg tgaccatgcc gtcacagtaa aggacgccaa gtttgtcgtg gcccaatgt    3900 cctccgcctg gacaccttt gacaacaaaa tcgtggtgta caaggcgac gtctacaaca    3960 tggactaccc accttttggc gcaggaagac caggacaatt tggtgacatt caaagtcgta    4020
caccggaaag taaagacgtt tatgccaaca ctcagttggt actacagagg ccagcagcag    4080
gcacggtaca tgtaccatac tctcaggcac catctggctt caagtattgg ctgaaggaac    4140
gaggagcatc gctacagcac acggcaccgt tcggttgcca gattgcgaca aacccggtaa    4200
gagctgtaaa ttgcgctgtg gggaacatac caatttccat cgacataccg gatgcggcct    4260
ttactagggt tgtcgatgca ccctctgtaa cggacatgtc atgcgaagta ccagcctgca    4320
ctcactcctc cgactttggg ggcgtcgcca tcatcaaata cacagctagc aagaaaggta    4380
aatgtgcagt acattcgatg accaacgccg ttaccattcg agaagccgac gtagaagtag    4440
aggggaactc ccagctgcaa atatccttct caacagccct ggcaagcgcc gagtttcgcg    4500
tgcaagtgtg ctccacacaa gtacactgcg cagccgcatg ccacctcca aaggaccaca    4560 tagtcaatta cccagcatca cacaccaccc ttgggtcca ggatatatcc acaacggcaa    4620
tgtcttgggt gcagaagatt acgggaggag taggattaat tgttgctgtt gctgccttaa    4680 tttaattgt ggtgctatgc gtgtcgttta gcaggcacta aggatctaga tctgctgtgc    4740
cttctagttg ccagccatct gttgtttgcc cctcccccgt gccttccttg acctggaag    4800 gtgccactcc cactgtcctt tcctaataaa atgaggaaat tgcatcgcat tgtctgagta    4860
ggtgtcattc tattctgggg ggtgggtgg ggcaggacag caaggggag gattgggaag     4920 acaatagcag gcatgctggg gatgcggtgg gctctatggg tacccaggtg ctgaagaatt    4980
gacccggttc ctcctgggcc agaaagaagc aggcacatcc ccttctctgt gacacaccct    5040
gtccacgccc ctggttctta gttccagccc cactcatagg acactcatag ctcaggaggg    5100
ctccgccttc aatcccaccc gctaaagtac ttggagcggt ctctccctcc ctcatcagcc    5160
caccaaacca aacctagcct ccaagagtgg gaagaaatta aagcaagata ggctattaag    5220
tgcagaggga gagaaaatgc ctccaacatg tgaggaagta atgagagaaa tcatagaatt    5280
ttaaggccat gatttaaggc catcatggcc taagcttgaa aggagatagg atcaaagctt    5340
ggcgtaatca tggtcatagc tgtttcctgt gtgaaattgt tatccgctca caattccaca    5400 caacatcga gccggaagca taagtgtaa agcctgggt gcctaatgag tgagctaact    5460
cacattaatt gcgttgcgct cactgcccgc tttccagtcg ggaaacctgt cgtgccagct    5520
gcattaatga atcggccaac gcgcggggag aggcggttg cgtattggc gctcttccgc    5580 ttcctcgctc actgactcgc tgcgctcggt cgttcggctg cggcgagcgg tatcagctca    5640
ctcaaaggcg gtaatacggt tatccacaga atcaggggat aacgcaggaa agaacatgtg    5700
```

```
agcaaaaggc cagcaaaagg ccaggaaccg taaaaaggcc gcgttgctgg cgttttttcca   5760 taggctccgc cccccctgacg agcatcacaa aaatcgacgc tcaagtcaga ggtggcgaaa   5820
cccgacagga ctataaagat accaggcgtt tccccctgga agctccctcg tgcgctctcc   5880
tgttccgacc ctgccgctta ccggatacct gtccgccttt ctcccttcgg aagcgtggc    5940 gctttctcat agctcacgct gtaggtatct cagttcggtg taggtcgttc gctccaagct   6000
gggctgtgtg cacgaacccc ccgttcagcc cgaccgctgc gccttatccg gtaactatcg   6060
tcttgagtcc aacccggtaa gacacgactt atcgccactg gcagcagcca ctggtaacag   6120
gattagcaga gcgaggtatg taggcggtgc tacagagttc ttgaagtggt ggcctaacta   6180
cggctacact agaagaacag tatttggtat ctgcgctctg ctgaagccag ttaccttcgg   6240
aaaaagagtt ggtagctctt gatccggcaa acaaaccacc gctggtagcg gtggtttttt   6300
tgtttgcaag cagcagatta cgcgcagaaa aaaggatct caagaagatc ctttgatctt    6360
ttctacgggg tctgacgctc agtggaacga aaactcacgt taagggattt tggtcatgag   6420
attatcaaaa aggatcttca cctagatcct tttaaattaa aaatgaagtt ttaaatcaat    6480
ctaaagtata tatgagtaaa cttggtctga cagttaccaa tgcttaatca gtgaggcacc    6540
tatctcagcg atctgtctat ttcgttcatc catagttgcc tgactccccg tcgtgtagat    6600
aactacgata cgggagggct taccatctgg ccccagtgct gcaatgatac cgcgagaacc    6660
acgctcaccg gctccagatt tatcagcaat aaaccagcca gccggaaggg ccgagcgcag    6720
aagtggtcct gcaactttat ccgcctccat ccagtctatt aattgttgcc gggaagctag    6780
agtaagtagt tcgccagtta atagtttgcg caacgttgtt gccattgcta caggcatcgt    6840
ggtgtcacgc tcgtcgtttg gtatggcttc attcagctcc ggttcccaac gatcaaggcg    6900
agttacatga tcccccatgt tgtgcaaaaa agcggttagc tccttcggtc ctccgatcgt    6960
tgtcagaagt aagttggccg cagtgttatc actcatggtt atggcagcac tgcataattc    7020
tcttactgtc atgccatccg taagatgctt ttctgtgact ggtgagtact caaccaagtc    7080
attctgagaa tagtgtatgc ggcgaccgag ttgctcttgc ccggcgtcaa tacgggataa    7140
taccgcgcca catagcagaa ctttaaaagt gctcatcatt ggaaaacgtt cttcggggcg    7200
aaaactctca aggatcttac cgctgttgag atccagttcg atgtaaccca ctcgtgcacc    7260
caactgatct tcagcatctt ttactttcac cagcgtttct gggtgagcaa aaacaggaag    7320
gcaaaatgcc gcaaaaaagg gaataagggc gacacggaaa tgttgaatac tcatactctt    7380
cctttttcaa tattattgaa gcatttatca gggttattgt ctcatgagcg gatacatatt    7440
tgaatgtatt tagaaaaata aacaaatagg ggttccgcgc acatttcccc gaaaagtgcc    7500
acctgacgtc taagaaacca ttattatcat gacattaacc tataaaaata ggcgtatcac    7560
gaggcccttt cgggtcgcgc gtttcggtga tgacggtgaa aacctctgac acatgcagct    7620
cccgttgacg gtcacagctt gtctgtaagc ggatgccggg agcagacaag cccgtcaggg    7680
cgcgtcagcg ggtgttggcg ggtgtcgggg ctggcttaac tatgcggcat cagagcagat    7740
tgtactgaga gtgcaccata aaattgtaaa cgttaatatt tgttaaaat tcgcgttaaa    7800 ttttttgttaa atcagctcat tttttaacca ataggccgaa atcggcaaaa tcccttataa    7860
atcaaaagaa tagcccgaga tagggttgag tgttgttcca gtttggaaca agagtccact    7920
attaaagaac gtggactcca acgtcaaagg gcgaaaaacc gtctatcagg gcgatggccc    7980
actacgtgaa ccatcaccca aatcaagttt tttggggtcg aggtgccgta aagcactaaa    8040
```

```
tcggaaccct aaagggagcc cccgatttag agcttgacgg ggaaagccgg cgaacgtggc    8100
gagaaaggaa gggaagaaag cgaaaggagc gggcgctagg gcgctggcaa gtgtagcggt    8160
cacgctgcgc gtaaccacca cacccgccgc gcttaatgcg ccgctacagg gcgcgtacta    8220
tggttgcttt gacgtatgcg gtgtgaaata ccgcacagat gcgtaaggag aaaataccgc    8280
atcaggcgcc attcgccatt caggctgcgc aactgttggg aagggcgatc ggtgcgggcc    8340
tcttcgctat tacgccagct ggcgaaaggg ggatgtgctg caaggcgatt aagttgggta    8400
acgccagggt tttcccagtc acgacgttgt aaaacgacgg ccagtgaatt ccatggtctc    8460
aactttc                                                              8467
```

<210> SEQ ID NO 46
<211> LENGTH: 8452
<212> TYPE: DNA
<213> ORGANISM: Artificial Sequence
<220> FEATURE:
<223> OTHER INFORMATION: Synthetic polynucleotide

<400> SEQUENCE: 46

```
gaattcccat tgcatacgtt gtatccatat cataatatgt acatttatat tggctcatgt      60
ccaacattac cgccatgttg acattgatta ttgactagtt attaatagta atcaattacg     120
gggtcattag ttcatagccc atatatggag ttccgcgtta cataacttac ggtaaatggc     180
ccgcctggct gaccgcccaa cgaccccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga cctttatggga ctttcctact    420 tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgga gttcatcccg acgcaaactt ctataacag aaggtaccaa ccccgaccct    960 gggcccacg ccctacaatt caagtaatta gacctagacc acgtccacag aggcaggctg    1020
ggcaactcgc ccagctgatc tccgcagtca acaaattgac catgcgcgcg gtacctcaac   1080
agaagcctcg cagaaatcgg aaaaacaaga agcaaaggca gaagaagcag gcgccgcaaa   1140
acgacccaaa gcaaagaag caaccaccac aaaagaagcc ggctcaaaag aagaagaaac   1200
caggccgtag ggagagaatg tgcatgaaaa ttgaaaatga ttgcatcttc gaagtcaagc   1260
atgaaggcaa agtgatgggc tacgcatgcc tggtggggga taaagtaatg aaaccagcac   1320
atgtgaaggg aactatcgac aatgccgatc tggctaaact ggcctttaag cggtcgtcta   1380
aatacgatct tgaatgtgca cagataccgg tgcacatgaa gtctgatgcc tcgaagttta   1440
cccacgagaa acccgagggg tactataact ggcatcacgg agcagtgcag tattcaggag   1500
gccggttcac tatcccgacg ggtgcaggca gccgggagga cagcggcaga ccgatcttcg   1560
acaacaaagg acgggtggtg gccatcgtcc taggagggggc caacgaaggt gcccgcacgg   1620
```

-continued

```
ccctctccgt ggtgacgtgg aacaaagaca tcgtcacaaa aattacccct gagggagccg   1680
aagagtggag cctcgccctc ccggtcttgt gcctgttggc aaacactaca ttcccctgct   1740
ctcagccgcc ttgcacaccc tgctgctacg aaaaggaacc ggaaagcacc ttgcgcatgc   1800
ttgaggacaa cgtgatgaga cccggatact accagctact aaaagcatcg ctgacttgct   1860
ctccccaccg ccaaagacgc agtactaagg acaattttaa tgtctataaa gccacaagac   1920
catatctagc tcattgtcct gactgcggag aagggcattc gtgccacagc cctatcgcat   1980
tggagcgcat cagaaatgaa gcaacggacg gaacgctgaa atccaggtc tctttgcaga    2040 tcgggataaa gacagatgac agccacgatt ggaccaagct gcgctatatg gatagccata   2100
cgccagcgga cgcggagcga gccggattgc ttgtaaggac ttcagcaccg tgcacgatca   2160
ccgggaccat gggacacttt attctcgccc gatgcccgaa aggagagacg ctgacagtgg   2220
gatttacgga cagcagaaag atcagccaca catgcacaca cccgttccat catgaaccac   2280
ctgtgatagg tagggagagg ttccactctc gaccacaaca tggtaaagag ttaccttgca   2340
gcacgtacgt gcagagcacc gctgccactg ctgaggagat agaggtgcat atgcccccag   2400
atactcctga ccgcacgctg atgacgcagc agtctggcaa cgtgaagatc acagttaatg   2460
ggcagacggt gcggtacaag tgcaactgcg gtggctccgg aggcggcgcc atcagcctgc   2520
accccaaggc caagatcgag gaatctggat ccaacgaggg actgacaacc acagacaaag   2580
tgatcaataa ctgcaaaatt gatcagtgcc atgctgcagt cactaatcac aagaattggc   2640
aatacaactc cctttagtc ccgcgcaacg ctgaactcgg ggaccgtaaa ggaaagatcc     2700
acatcccatt cccattggca aacgtgactt gcagagtgcc aaaagcaaga aaccctacag   2760
taacttacgg aaaaaaccaa gtcaccatgc tgctgtatcc tgaccatccg acactcttgt   2820
cttaccgtaa catgggacag gaaccaaatt accacgagga gtgggtgaca cacaagaagg   2880
aggttacctt gaccgtgcct actgagggtc tggaggtcac ttggggcaac aacgaaccat   2940
acaagtactg gccgcagatg tctacgaacg gtactgctca tggtcaccca catgagataa   3000
tcttgtacta ttatgagctg taccccacta tgactgtagt cattgtgtcg gtggcctcgt   3060
tcgtgcttct gtcgatggtg ggcacagcag tgggaatgtg tgtgtgcgca cggcgcagat   3120
gcattacacc atatgaatta acaccaggag ccactgttcc cttcctgctc agcctgctat   3180
gctgcgtcag aacgaccaag gcggccacat attacgaggc tgcggcatat ctatggaacg   3240
aacagcagcc cctgttctgg ttgcaggctc ttatcccgct ggccgccttg atcgtcctgt   3300
gcaactgtct gaaactcttg ccatgctgct gtaagaccct ggcttttta gccgtaatga    3360 gcatcggtgc ccacactgtg agcgcgtacg aacacgtaac agtgatcccg aacacggtgg   3420
gagtaccgta taagactctt gtcaacagac cgggttacag ccccatggtg ttggagatgg   3480
agctacaatc agtcaccttg gaaccaacac tgtcacttga ctacatcacg tgcgagtaca   3540
aaactgtcat cccctccccg tacgtgaagt gctgtggtac agcagagtgc aaggacaaga   3600
gcctaccaga ctacagctgc aaggtctta ctggagtcta cccatttatg tggggcggcg     3660
cctactgctt ttgcgacgcc gaaaatacgc aattgagcga ggcacatgta gagaaatctg   3720
aatcttgcaa aacagagttt gcatcggcct acagagccca caccgcatcg cgtcggcga    3780 agctccgcgt cctttaccaa ggaaacaaca ttaccgtagc tgcctacgct aacggtgacc   3840
atgccgtcac agtaaaggac gccaagtttg tcgtgggccc aatgtcctcc gcctggacac   3900
cttttgacaa caaaatcgtg gtgtacaaag gcgacgtcta caacatggac tacccacctt   3960
```

```
ttggcgcagg aagaccagga caatttggtg acattcaaag tcgtacaccg gaaagtaaag    4020
acgtttatgc caacactcag ttggtactac agaggccagc agcaggcacg gtacatgtac    4080
catactctca ggcaccatct ggcttcaagt attggctgaa ggaacgagga gcatcgctac    4140
agcacacggc accgttcggt tgccagattg cgacaaaccc ggtaagagct gtaaattgcg    4200
ctgtggggaa cataccaatt tccatcgaca taccggatgc ggcctttact agggttgtcg    4260
atgcaccctc tgtaacggac atgtcatgcg aagtaccagc ctgcactcac tcctccgact    4320
ttgggggcgt cgccatcatc aaatacacag ctagcaagaa aggtaaatgt gcagtacatt    4380
cgatgaccaa cgccgttacc attcgagaag ccgacgtaga agtagagggg aactcccagc    4440
tgcaaatatc cttctcaaca gccctggcaa gcgccgagtt tcgcgtgcaa gtgtgctcca    4500
cacaagtaca ctgcgcagcc gcatgccacc ctccaaagga ccacatagtc aattacccag    4560
catcacacac caccctgggg gtccaggata tatccacaac ggcaatgtct tgggtgcaga    4620
agattacggg aggagtagga ttaattgttg ctgttgctgc cttaattttta attgtggtgc    4680
tatgcgtgtc gtttagcagg cactaaggat ctagatctgc tgtgccttct agttgccagc    4740
catctgttgt ttgcccctcc cccgtgcctt ccttgaccct ggaaggtgcc actcccactg    4800
tcctttccta ataaaatgag gaaattgcat cgcattgtct gagtaggtgt cattctattc    4860
tggggggtgg ggtggggcag gacagcaagg gggaggattg gaagacaat agcaggcatg    4920
ctggggatgc ggtgggctct atgggtaccc aggtgctgaa gaattgaccc ggttcctcct    4980
gggccagaaa gaagcaggca catccccttc tctgtgacac accctgtcca cgcccctggt    5040
tcttagttcc agccccactc ataggacact catagctcag gagggctccg ccttcaatcc    5100
cacccgctaa agtacttgga gcggtctctc cctccctcat cagcccacca aaccaaacct    5160
agcctccaag agtgggaaga aattaaagca agataggcta ttaagtgcag agggagagaa    5220
aatgcctcca acatgtgagg aagtaatgag agaaatcata gaattttaag gccatgattt    5280
aaggccatca tggcctaagc ttgaaaggag ataggatcaa agcttggcgt aatcatggtc    5340
atagctgttt cctgtgtgaa attgttatcc gctcacaatt ccacacaaca tacgagccgg    5400
aagcataaag tgtaaagcct ggggtgccta atgagtgagc taactcacat taattgcgtt    5460
gcgctcactg cccgctttcc agtcgggaaa cctgtcgtgc cagctgcatt aatgaatcgg    5520
ccaacgcgcg gggagaggcg gtttgcgtat tgggcgctct tccgcttcct cgctcactga    5580
ctcgctgcgc tcggtcgttc ggctgcggcg agcggtatca gctcactcaa aggcggtaat    5640
acggttatcc acagaatcag gggataacgc aggaaagaac atgtgagcaa aaggccagca    5700
aaaggccagg aaccgtaaaa aggccgcgtt gctggcgttt ttccataggc tccgcccccc    5760
tgacgagcat cacaaaaatc gacgctcaag tcagaggtgg cgaaacccga caggactata    5820
aagataccag gcgtttcccc ctggaagctc cctcgtgcgc tctcctgttc cgaccctgcc    5880
gcttaccgga tacctgtccg cctttctccc ttcgggaagc gtggcgcttt ctcatagctc    5940
acgctgtagg tatctcagtt cggtgtaggt cgttcgctcc aagctgggct gtgtgcacga    6000
accccccgtt cagcccgacc gctgcgcctt atccggtaac tatcgtcttg agtccaaccc    6060
ggtaagacac gacttatcgc cactggcagc agccactggt aacaggatta gcagagcgag    6120
gtatgtaggc ggtgctacag agttcttgaa gtggtggcct aactacggct acactagaag    6180
aacagtattt ggtatctgcg ctctgctgaa gccagttacc ttcggaaaaa gagttggtag    6240
ctcttgatcc ggcaaacaaa ccaccgctgg tagcggtggt ttttttgttt gcaagcagca    6300
gattacgcgc agaaaaaaag gatctcaaga agatcctttg atcttttcta cggggtctga    6360
```

-continued

```
cgctcagtgg aacgaaaact cacgttaagg gattttggtc atgagattat caaaaaggat    6420
cttcacctag atccttttaa attaaaaatg aagttttaaa tcaatctaaa gtatatatga    6480
gtaaacttgg tctgacagtt accaatgctt aatcagtgag gcacctatct cagcgatctg    6540
tctatttcgt tcatccatag ttgcctgact ccccgtcgtg tagataacta cgatacggga    6600
gggcttacca tctggcccca gtgctgcaat gataccgcga gaaccacgct caccggctcc    6660
agatttatca gcaataaacc agccagccgg aagggccgag cgcagaagtg gtcctgcaac    6720
tttatccgcc tccatccagt ctattaattg ttgccgggaa gctagagtaa gtagttcgcc    6780
agttaatagt ttgcgcaacg ttgttgccat tgctacaggc atcgtggtgt cacgctcgtc    6840
gtttggtatg gcttcattca gctccggttc ccaacgatca aggcgagtta catgatcccc    6900
catgttgtgc aaaaaagcgg ttagctcctt cggtcctccg atcgttgtca gaagtaagtt    6960
ggccgcagtg ttatcactca tggttatggc agcactgcat aattctctta ctgtcatgcc    7020
atccgtaaga tgcttttctg tgactggtga gtactcaacc aagtcattct gagaatagtg    7080
tatgcggcga ccgagttgct cttgcccggc gtcaatacgg gataataccg cgccacatag    7140
cagaacttta aaagtgctca tcattggaaa acgttcttcg gggcgaaaac tctcaaggat    7200
cttaccgctg ttgagatcca gttcgatgta acccactcgt gcacccaact gatcttcagc    7260
atcttttact ttcaccagcg tttctgggtg agcaaaaaca ggaaggcaaa atgccgcaaa    7320
aaagggaata agggcgacac ggaaatgttg aatactcata ctcttccttt ttcaatatta    7380
ttgaagcatt tatcagggtt attgtctcat gagcggatac atatttgaat gtatttagaa    7440
aaataaacaa ataggggttc cgcgcacatt tccccgaaaa gtgccacctg acgtctaaga    7500
aaccattatt atcatgacat taacctataa aaataggcgt atcacgaggc cctttcgggt    7560
cgcgcgtttc ggtgatgacg gtgaaaacct ctgacacatg cagctcccgt tgacggtcac    7620
agcttgtctg taagcggatg ccgggagcag acaagcccgt cagggcgcgt cagcgggtgt    7680
tggcgggtgt cggggctggc ttaactatgc ggcatcagag cagattgtac tgagagtgca    7740
ccataaaatt gtaaacgtta atattttgtt aaaattcgcg ttaaattttt gttaaatcag    7800 ctcattttt aaccaatagg ccgaaatcgg caaaatccct tataaatcaa agaatagcc    7860 cgagataggg ttgagtgttg ttccagtttg gaacaagagt ccactattaa agaacgtgga    7920
ctccaacgtc aaagggcgaa aaaccgtcta tcagggcgat ggcccactac gtgaaccatc    7980
acccaaatca gttttttgg ggtcgaggtg ccgtaaagca ctaaatcgga accctaaagg    8040
gagcccccga tttagagctt gacggggaaa gccggcgaac gtggcgagaa aggaagggaa    8100
gaaagcgaaa ggagcgggcg ctagggcgct ggcaagtgta gcggtcacgc tgcgcgtaac    8160
caccacaccc gccgcgctta atgcgccgct acagggcgcg tactatggtt gctttgacgt    8220
atgcggtgtg aaataccgca cagatgcgta aggagaaaat accgcatcag gcgccattcg    8280
ccattcaggc tgcgcaactg ttgggaaggg cgatcggtgc gggcctcttc gctattacgc    8340
cagctggcga aagggggatg tgctgcaagg cgattaagtt gggtaacgcc agggttttcc    8400
cagtcacgac gttgtaaaac gacggccagt gaattccatg gtctcaactt tc           8452
```

<210> SEQ ID NO 47  
<211> LENGTH: 7290  
<212> TYPE: DNA  
<213> ORGANISM: Artificial Sequence  
<220> FEATURE:  
<223> OTHER INFORMATION: Synthetic polynucleotide

```
<400> SEQUENCE: 47
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt gacgcgtgtt ggcattgatt     420
attgactagt tattaatagt aatcaattac ggggtcatta gttcatagcc catatatgga     480
gttccgcgtt acataactta cggtaaatgg cccgcctggc tgaccgccca acgacccccg     540
cccattgacg tcaataatga cgtatgttcc catagtaacg ccaatagggg ctttccattg     600
acgtcaatgg gtggagtatt tacggtaaac tgcccacttg gcagtacatc aagtgtatca     660
tatgccaagt acgcccccta ttgacgtcaa tgacggtaaa tggcccgcct ggcattatgc     720
ccagtacatg accttatggg actttcctac ttggcagtac atctacgtat tagtcatcgc     780
tattaccatg gtgatgcggt tttggcagta catcaatggg cgtggatagc ggtttgactc     840
acggggattt ccaagtctcc accccattga cgtcaatggg agtttgtttt ggcaccaaaa     900
tcaacgggac tttccaaaat gtcgtaacaa ctccgcccca ttgacgcaaa tgggcggtag     960
gcgtgtacgg tgggaggtct atataagcag agctcgttta gtgaaccgtc agataactgc    1020
aggtcgacga tatcgcggcc gccaccatgt cccgttcca gccaatgtat ccgatgcagc    1080
caatgcccta tcgcaacccg ttcgcggccc cgcgcaggcc ctggttcccc agaaccgacc    1140
cttttctggc gatgcaggtg caggaattaa cccgctcgat ggctaacctg acgttcaagc    1200
aacgccggga cgcgccacct gagggggccat ccgctaataa accgaagaag gaggcctcgc    1260
aaaaacagaa agggggaggc caagggaaga agaagaagaa ccaagggaag aagaaggcta    1320
agacagggcc gcctaatccg aaggcacaga atggaaacaa gaagaagacc aacaagaaac    1380
caggcaagag acagcgcatg gtcatgaaat tggaatctga caagacgttc ccaatcatgt    1440
tggaagggaa gataaacggc tacgcttgtg tggtcggagg gaagttattc aggccgatgc    1500
atgtggaagg caagatcgac aacgacgttc tggccgcgct taagacgaag aaagcatcca    1560
aatacgatct tgagtatgca gatgtgccac agaacatgcg ggccgataca ttcaaataca    1620
cccatgagaa accccaaggc tattacagct ggcatcatgg agcagtccaa tatgaaaatg    1680
ggcgtttcac ggtgccgaaa ggagttgggg ccaagggaga cagcggacga cccattctgg    1740
ataaccaggg acgggtggtc gctattgtgc tgggaggtgt gaatgaagga tctaggacag    1800 cccttttcagt cgtcatgtgg aacgagaagg gagttaccgt gaagtatact ccagagaact    1860
gcgagcaatg gtcactagtg accaccatgt gtctgctcgc caatgtgacg ttcccatgtg    1920
ctcaaccacc aatttgctac gacagaaaac cagcagagac tttggccatg ctcagcgtta    1980
acgttgacaa cccgggctac gatgagctgc tggaagcagc tgttaagtgc cccggaagga    2040
aaaggagatc caccgaggag ctgtttaatg agtataagct aacgcgccct acatggcca    2100 gatgcatcag atgtgcagtt gggagctgcc atagtccaat agcaatcgag gcagtaaaga    2160
gcgacgggca cgacggttat gttagacttc agacttcctc gcagtatggc ctggattcct    2220
ccggcaactt aaagggcagg accatgcggt atgacatgca cggaccatt aaagagatac    2280 cactacatca agtgtcactc tatacatctc gcccgtgtca cattgtggat gggcacggtt    2340
```

```
atttcctgct tgccaggtgc ccggcagggg actccatcac catgaatttt aagaaagatt    2400
ccgtcagaca ctcctgctcg gtgccgtatg aagtgaaatt taatcctgta ggcagagaac    2460
tctatactca tcccccagaa cacggagtag agcaagcgtg ccaagtctac gcacatgatg    2520
cacagaacag aggagcttat gtcgagatgc acctcccggg ctcagaagtg acagcagtt     2580
tggtttcctt gagcggcagt tccggaggct gcatcatcag ctacggcgga gccgactact    2640
gcggcggatc ctcagtcacc gtgacacctc ctgatgggac tagcgccctg gtggaatgcg    2700
agtgtggcgg cacaaagatc tccgagacca tcaacaagac aaaacagttc agccagtgca    2760
caaagaagga gcagtgcaga gcatatcggc tgcagaacga taagtgggtg tataattctg    2820
acaaactgcc caaagcagcg ggagccacct aaaaggaaa actgcatgtc ccattcttgc      2880
tggcagacgg caaatgcacc gtgcctctag caccagaacc tatgataacc ttcggtttca    2940
gatcagtgtc actgaaactg caccctaaga atcccacata tctaatcacc cgccaacttg    3000
ctgatgagcc tcactacacg cacgagctca tatctgaacc agctgttagg aattttaccg    3060
tcaccgaaaa agggtgggag tttgtatggg gaaaccaccc gccgaaaagg ttttgggcac    3120
aggaaacagc acccggaaat ccacatgggc taccgcacga ggtgataact cattattacc    3180
acagataccc tatgtccacc atcctgggtt tgtcaatttg tgccgccatt gcaaccgttt    3240
ccgttgcagc gtctacctgg ctgttttgca gatcaagagt tgcgtgccta actccttacc    3300
ggctaacacc taacgctagg ataccatttt gtctggctgt gctttgctgc gcccgcactg    3360
cccgggccga ccacctgg gagtccttgg atcacctatg gaacaataac caacagatgt       3420
tctggattca attgctgatc cctctggccg ccttgatcgt agtgactcgc ctgctcaggt    3480
gcgtgtgctg tgtcgtgcct ttttagtca tggccggcgc cgcaggcgcc ggcgcctacg     3540
agcacgcgac cacgatgccg agccaagcgg gaatctcgta taacactata gtcaacagag    3600
caggctacgc accactccct atcagcataa caccaacaaa gatcaagctg atacctacag    3660
tgaacttgga gtacgtcacc tgccactaca aaacaggaat ggattcacca gccatcaaat    3720
gctgcgatc tcaggaatgc actccaactt acaggcctga tgaacagtgc aaagtcttca     3780
caggggttta cccgttcatg tggggtggtg catattgctt ttgcgacact gagaacaccc    3840
aagtcagcaa ggcctacgta atgaaatctg acgactgcct tgcggatcat gctgaagcat    3900
ataaagcgca cacagcctca gtgcaggcgt tcctcaacat cacagtggga gaacactcta    3960
ttgtgactac cgtgtatgtg aatggagaaa ctcctgtgaa tttcaatggg gtcaaaataa    4020
ctgcaggtcc gctttccaca gcttggacac cctttgatcg caaaatcgtg cagtatgccg    4080
gggagatata taattatgat tttcctgagt atggggcagg acaaccagga gcatttggag    4140
atatacaatc cagaacagtc tcaagctctg atctgtatgc caataccaac ctagtgctgc    4200
agagacccaa agcaggagcg atccacgtgc catacactca ggcaccttcg ggttttgagc    4260
aatggaagaa agataaagct ccatcattga aatttaccgc cccctttcgga tgcgaaatat    4320
atacaaaccc cattcgcgcc gaaaactgtg ctgtagggtc aattccatta gcctttgaca    4380
ttcccgacgc cttgttcacc agggtgtcag aaacaccgac actttcagcg gccgaatgca    4440
ctcttaacga gtgcgtgtat tcttccgact tggtgggat cgccacggtc aagtactcgg     4500
ccagcaagtc aggcaagtgc gcagtccatg tgccatcagg gactgctacc ctaaaagaag    4560
cagcagtcga gctaaccgag caagggtcgg cgactatcca tttctcgacc gcaaatatcc    4620
acccggagtt caggctccaa atatgcacat catatgttac gtgcaaaggt gattgtcacc    4680
```

```
ccccgaaaga ccatattgtg acacaccctc agtatcacgc ccaaacattt acagccgcgg    4740
tgtcaaaaac cgcgtggacg tggttaacat ccctgctggg aggatcagcc gtaattatta    4800
taattggctt ggtgctggct actattgtgg ccatgtacgt gctgaccaac cagaaacata    4860
attaaggatc tagatctgct gtgccttcta gttgccagcc atctgttgtt tgcccctccc    4920
ccgtgccttc cttgaccctg gaaggtgcca ctcccactgt cctttcctaa taaaatgagg    4980
aaattgcatc gcattgtctg agtaggtgtc attctattct gggggtggg gtggggcagg    5040 acagcaaggg ggaggattgg gaagacaata gcaggcatgc tggggatgcg gtgggctcta    5100
tggctcgagc atggtcatag ctgtttcctg tgtgaaattg ttatccgctc acaattccac    5160
acaacatacg agccggaagc ataaagtgta aagcctgggg tgcctaatga gtgagctaac    5220
tcacattaat tgcgttgcgc tcactgcccg ctttccagtc gggaaacctg tcgtgccagc    5280
tgcattaatg aatcggccaa cgcgcgggga gaggcggttt gcgtattggg cgctcttccg    5340
cttcctcgct cactgactcg ctgcgctcgg tcgttcggct gcggcgagcg gtatcagctc    5400
actcaaaggc ggtaatacgg ttatccacag aatcagggga taacgcagga agaacatgt    5460 gagcaaaagg ccagcaaaag gccaggaacc gtaaaaaggc cgcgttgctg gcgttttcc    5520 ataggctccg ccccctgac gagcatcaca aaaatcgacg ctcaagtcag aggtggcgaa    5580
acccgacagg actataaaga taccaggcgt ttccccctgg aagctccctc gtgcgctctc    5640
ctgttccgac cctgccgctt accggatacc tgtccgcctt tctcccttcg ggaagcgtgg    5700
cgctttctca tagctcacgc tgtaggtatc tcagttcggt gtaggtcgtt cgctccaagc    5760
tgggctgtgt gcacgaaccc cccgttcagc ccgaccgctg cgccttatcc ggtaactatc    5820
gtcttgagtc caacccggta agacacgact tatcgccact ggcagcagcc actggtaaca    5880
ggattagcag agcgaggtat gtaggcggtg ctacagagtt cttgaagtgg tggcctaact    5940
acggctacac tagaagaaca gtatttggta tctgcgctct gctgaagcca gttaccttcg    6000
gaaaaagagt tggtagctct tgatccggca aacaaaccac cgctggtagc ggtggttttt    6060
ttgtttgcaa gcagcagatt acgcgcagaa aaaaaggatc tcaagaagat cctttgatct    6120
tttctacggg gtctgacgct cagtggaacg aaaactcacg ttaagggatt ttggtcatga    6180
gattatcaaa aaggatcttc acctagatcc ttttaaatta aaaatgaagt tttaaatcaa    6240
tctaaagtat atatgagtaa acttggtctg acagttagaa aaactcatcg agcatcaaat    6300
gaaactgcaa tttattcata tcaggattat caataccata ttttttgaaaa agccgtttct    6360 gtaatgaagg agaaaactca ccgaggcagt tccataggat ggcaagatcc tggtatcggt    6420
ctgcgattcc gactcgtcca acatcaatac aacctattaa tttccctcg tcaaaaataa    6480 ggttatcaag tgagaaatca ccatgagtga cgactgaatc cggtgagaat ggcaaaagtt    6540
tatgcatttc tttccagact tgttcaacag gccagccatt acgctcgtca tcaaaatcac    6600
tcgcatcaac caaaccgtta ttcattcgtg attgcgcctg agcgagacga atacgcgat    6660 cgctgttaaa aggacaatta caaacaggaa tcgaatgcaa ccggcgcagg aacactgcca    6720
gcgcatcaac aatattttca cctgaatcag gatattcttc taatacctgg aatgctgttt    6780
tcccagggat cgcagtggtg agtaaccatg catcatcagg agtacggata aaatgcttga    6840
tggtcggaag aggcataaat tccgtcagcc agtttagtct gaccatctca tctgtaacat    6900
cattggcaac gctacctttg ccatgtttca gaaacaactc tggcgcatcg gcttcccat    6960 acaatcgata gattgtcgca cctgattgcc cgacattatc gcgagcccat ttatacccat    7020
ataaatcagc atccatgttg gaatttaatc gcggcctaga gcaagacgtt tcccgttgaa    7080
```

```
tatggctcat actcttcctt tttcaatatt attgaagcat ttatcagggt tattgtctca    7140
tgagcggata catatttgaa tgtatttaga aaaataaaca aatagggggtt ccgcgcacat   7200 ttccccgaaa agtgccacct gacgtctaag aaaccattat tatcatgaca ttaacctata   7260
aaaataggcg tatcacgagg ccctttcgtc                                     7290

<210> SEQ ID NO 48
<211> LENGTH: 8491
<212> TYPE: DNA
<213> ORGANISM: Artificial Sequence
<220> FEATURE:
<223> OTHER INFORMATION: Synthetic polynucleotide

<400> SEQUENCE: 48
gaattcccat tgcatacgtt gtatccatat cataatatgt acatttatat tggctcatgt      60
ccaacattac cgccatgttg acattgatta ttgactagtt attaatagta atcaattacg     120
gggtcattag ttcatagccc atatatggag ttccgcgtta cataacttac ggtaaatggc     180
ccgcctggct gaccgcccaa cgacccccgc ccattgacgt caataatgac gtatgttccc     240
atagtaacgc caatagggac tttccattga cgtcaatggg tggagtattt acggtaaact     300
gcccacttgg cagtacatca agtgtatcat atgccaagta cgccccctat tgacgtcaat     360
gacggtaaat ggcccgcctg gcattatgcc cagtacatga ccttatggga ctttcctact     420
tggcagtaca tctacgtatt agtcatcgct attaccatgg tgatgcggtt ttggcagtac     480
atcaatgggc gtggatagcg gtttgactca cggggatttc caagtctcca ccccattgac     540
gtcaatggga gtttgttttg gcaccaaaat caacgggact ttccaaaatg tcgtaacaac     600
tccgccccat tgacgcaaat gggcggtagg cgtgtacggt gggaggtcta tataagcaga     660
gctcgtttag tgaaccgtca gatcgcctgg agacgccatc cacgctgttt tgacctccat     720
agaagacacc gggaccgatc cagcctccgt taacggtgga gggcagtgta gtctgagcag     780
tactcgttgc tgccgcgcgc gccaccagac ataatagctg acagactaac agactgttcc     840
tttccatggg tcttttctgc agtcaccgtc gtcgacacgt gtgatcagat atcgcggccg     900
ccaccatgtt cccgttccag ccaatgtatc cgatgcagcc aatgcccctat cgcaacccgt     960 tcgcggcccc gcgcaggccc tggttcccca gaaccgaccc ttttctggcg atgcaggtgc    1020
aggaattaac ccgctcgatg gctaacctga cgttcaagca acgccgggac gcgccacctg    1080 agggggccatc cgctaataaa ccgaagaagg aggcctcgca aaaacagaaa ggggggaggcc   1140 aagggaagaa gaagaagaac caagggaaga agaaggctaa gacagggccg cctaatccga    1200
aggcacagaa tggaaacaag aagaagacca acaagaaacc aggcaagaga cagcgcatgg    1260
tcatgaaatt ggaatctgac aagacgttcc caatcatgtt ggaagggaag ataaacggct    1320
acgcttgtgt ggtcggaggg aagttattca ggccgatgca tgtggaaggc aagatcgaca    1380
acgacgttct ggccgcgctt aagacgaaga agcatccaa atacgatctt gagtatgcag    1440
atgtgccaca gaacatgcgg gccgatacat tcaaatacac ccatgagaaa ccccaaggct    1500
attacagctg gcatcatgga gcagtccaat atgaaaatgg gcgtttcacg gtgccgaaag    1560
gagttggggc aagggagac agcggacgac ccattctgga taaccaggga cgggtggtcg    1620
ctattgtgct gggaggtgtg aatgaaggat ctaggacagc cctttcagtc gtcatgtgga    1680
acgagaaggg agttaccgtg aagtatactc cagagaactg cgagcaatgg tcactagtga    1740
ccaccatgtg tctgctcgcc aatgtgacgt tcccatgtgc tcaaccacca atttgctacg    1800
```

```
acagaaaacc agcagagact ttggccatgc tcagcgttaa cgttgacaac ccgggctacg    1860
atgagctgct ggaagcagct gttaagtgcc ccggaaggaa aaggagatcc accgaggagc    1920
tgtttaatga gtataagcta acgcgccctt acatggccag atgcatcaga tgtgcagttg    1980
ggagctgcca tagtccaata gcaatcgagg cagtaaagag cgacgggcac gacggttatg    2040
ttagacttca gacttcctcg cagtatggcc tggattcctc cggcaactta aagggcagga    2100
ccatgcggta tgacatgcac gggaccatta aagagatacc actacatcaa gtgtcactct    2160
atacatctcg cccgtgtcac attgtggatg ggcacggtta tttcctgctt gccaggtgcc    2220
cggcagggga ctccatcacc atggaattta agaaagattc cgtcagacac tcctgctcgg    2280
tgccgtatga agtgaaattt aatcctgtag gcagagaact ctatactcat cccccagaac    2340
acggagtaga gcaagcgtgc caagtctacg cacatgatgc acagaacaga ggagcttatg    2400
tcgagatgca cctcccgggc tcagaagtgg acagcagttt ggtttccttg agcggcagtt    2460
ccggaggact aaactggtac cgcatgagcc ccagcaacca gacggacaag ctggccgcct    2520
tcggaggatc ctcagtcacc gtgacacctc ctgatgggac tagcgccctg gtggaatgcg    2580
agtgtggcgg cacaaagatc tccgagacca tcaacaagac aaaacagttc agccagtgca    2640
caaagaagga gcagtgcaga gcatatcggc tgcagaacga taagtgggtg tataattctg    2700
acaaactgcc caaagcagcg ggagccaccct taaaaggaaa actgcatgtc ccattcttgc    2760
tggcagacgc caaatgcacc gtgcctctag caccagaacc tatgataacc ttcggtttca    2820
gatcagtgtc actgaaactg caccctaaga atcccacata tctaatcacc cgccaacttg    2880
ctgatgagcc tcactacacg cacgagctca tatctgaacc agctgttagg aattttaccg    2940
tcaccgaaaa agggtgggag tttgtatggg gaaaccaccc gccgaaaagg ttttgggcac    3000
aggaaacagc acccggaaat ccacatgggc taccgcacga ggtgataact cattattacc    3060
acagataccc tatgtccacc atcctggggtt tgtcaatttg tgccgccatt gcaaccgttt    3120
ccgttgcagc gtctacctgg ctgttttgca gatcaagagt tgcgtgccta actccttacc    3180
ggctaacacc taacgctagg ataccatttt gtctggctgt gctttgctgc gcccgcactg    3240
cccgggccga gaccacctgg gagtccttgg atcacctatg aacaataac caacagatgt    3300 tctggattca attgctgatc cctctggccg ccttgatcgt agtgactcgc ctgctcaggt    3360
gcgtgtgctg tgtcgtgcct ttttttagtca tggccggcgc cgcaggcgcc ggcgcctacg    3420
agcacgcgac cacgatgccg agccaagcgg gaatctcgta taacactata gtcaacagag    3480
caggctacgc accactccct atcagcataa caccaacaaa gatcaagctg atacctacag    3540
tgaacttgga gtacgtcacc tgccactaca aaacaggaat ggattcacca gccatcaaat    3600
gctgcggatc tcaggaatgc actccaactt acaggcctga tgaacagtgc aaagtcttca    3660
caggggttta cccgttcatg tggggtggtg catattgctt ttgcgacact gagaacaccc    3720
aagtcagcaa ggcctacgta atgaaatctg acgactgcct tgcggatcat gctgaagcat    3780
ataaagcgca cacagcctca gtgcaggcgt tcctcaacat cacagtggga gaacactcta    3840
ttgtgactac cgtgtatgtg aatggagaaa ctcctgtgaa tttcaatggg gtcaaaataa    3900
ctgcaggtcc gctttccaca gcttggacac cctttgatcg caaaatcgtg cagtatgccg    3960
gggagatcta taattatgat tttcctgagt atggggcagg acaaccagga gcatttggag    4020
atatacaatc cagaacagtc tcaagctctg atctgtatgc caataccaac ctagtgctgc    4080
agagacccaa agcaggagcg atccacgtgc catacactca ggcaccttcg ggttttgagc    4140
aatggaagaa agataaagct ccatcattga atttaccgc cccttttcgga tgcgaaatat    4200
```

```
atacaaaccc cattcgcgcc gaaaactgtg ctgtagggtc aattccatta gcctttgaca    4260
ttcccgacgc cttgttcacc agggtgtcag aaacaccgac actttcagcg gccgaatgca    4320
ctcttaacga gtgcgtgtat tcttccgact ttggtgggat cgccacggtc aagtactcgg    4380
ccagcaagtc aggcaagtgc gcagtccatg tgccatcagg gactgctacc ctaaaagaag    4440
cagcagtcga gctaaccgag caagggtcgg cgactatcca tttctcgacc gcaaatatcc    4500
acccggagtt caggctccaa atatgcacat catatgttac gtgcaaaggt gattgtcacc    4560
ccccgaaaga ccatattgtg acacaccctc agtatcacgc ccaaacattt acagccgcgg    4620
tgtcaaaaac cgcgtggacg tggttaacat ccctgctggg aggatcagcc gtaattatta    4680
taattggctt ggtgctggct actattgtgg ccatgtacgt gctgaccaac cagaaacata    4740
attaaggatc tagatctgct gtgccttcta gttgccagcc atctgttgtt tgcccctccc    4800
ccgtgccttc cttgaccctg gaaggtgcca ctcccactgt cctttcctaa taaaatgagg    4860
aaattgcatc gcattgtctg agtaggtgtc attctattct ggggggtggg gtggggcagg    4920
acagcaaggg ggaggattgg gaagacaata gcaggcatgc tggggatgcg gtgggctcta    4980
tgggtaccca ggtgctgaag aattgacccg gttcctcctg ggccagaaag aagcaggcac    5040
atccccttct ctgtgacaca ccctgtccac gcccctggtt cttagttcca gccccactca    5100
taggacactc atagctcagg agggctccgc cttcaatccc acccgctaaa gtacttggag    5160
cggtctctcc ctccctcatc agcccaccaa accaaaccta gcctccaaga gtgggaagaa    5220
attaaagcaa gataggctat taagtgcaga gggagagaaa atgcctccaa catgtgagga    5280
agtaatgaga gaaatcatag aattttaagg ccatgattta aggccatcat ggcctaagct    5340
tgaaaggaga taggatcaaa gcttggcgta atcatggtca tagctgtttc ctgtgtgaaa    5400
ttgttatccg ctcacaattc cacacaacat acgagccgga agcataaagt gtaaagcctg    5460
gggtgcctaa tgagtgagct aactcacatt aattgcgttg cgctcactgc ccgctttcca    5520
gtcgggaaac ctgtcgtgcc agctgcatta atgaatcggc caacgcgcgg ggagaggcgg    5580
tttgcgtatt gggcgctctt ccgcttcctc gctcactgac tcgctgcgct cggtcgttcg    5640
gctgcggcga gcggtatcag ctcactcaaa ggcggtaata cggttatcca cagaatcagg    5700
ggataacgca ggaaagaaca tgtgagcaaa aggccagcaa aaggccagga accgtaaaaa    5760
ggccgcgttg ctggcgtttt tccataggct ccgcccccct gacgagcatc acaaaaatcg    5820
acgctcaagt cagaggtggc gaaacccgac aggactataa agataccagg cgtttccccc    5880
tggaagctcc ctcgtgcgct ctcctgttcc gaccctgccg cttaccggat acctgtccgc    5940
ctttctccct tcgggaagcg tggcgctttc tcatagctca cgctgtaggt atctcagttc    6000
ggtgtaggtc gttcgctcca agctgggctg tgtgcacgaa ccccccgttc agcccgaccg    6060
ctgcgcctta tccggtaact atcgtcttga gtccaacccg gtaagacacg acttatcgcc    6120
actggcagca gccactggta acaggattag cagagcgagg tatgtaggcg gtgctacaga    6180
gttcttgaag tggtggccta actacggcta cactagaaga acagtatttg gtatctgcgc    6240
tctgctgaag ccagttacct tcggaaaaag agttggtagc tcttgatccg gcaaacaaac    6300
caccgctggt agcggtggtt ttttgtttg caagcagcag attacgcgca gaaaaaaagg    6360
atctcaagaa gatcctttga tcttttctac ggggtctgac gctcagtgga acgaaaactc    6420
acgttaaggg attttggtca tgagattatc aaaaaggatc ttcacctaga tccttttaaa    6480
ttaaaaatga agttttaaat caatctaaag tatatatgag taaacttggt ctgacagtta    6540
```

| | |
|---|---|
| ccaatgctta atcagtgagg cacctatctc agcgatctgt ctatttcgtt catccatagt | 6600 |
| tgcctgactc cccgtcgtgt agataactac gatacgggag ggcttaccat ctggccccag | 6660 |
| tgctgcaatg ataccgcgag aaccacgctc accggctcca gatttatcag caataaacca | 6720 |
| gccagccgga agggccgagc gcagaagtgg tcctgcaact ttatccgcct ccatccagtc | 6780 |
| tattaattgt tgccgggaag ctagagtaag tagttcgcca gttaatagtt tgcgcaacgt | 6840 |
| tgttgccatt gctacaggca tcgtggtgtc acgctcgtcg tttggtatgg cttcattcag | 6900 |
| ctccggttcc caacgatcaa ggcgagttac atgatccccc atgttgtgca aaaaagcggt | 6960 |
| tagctccttc ggtcctccga tcgttgtcag aagtaagttg gccgcagtgt tatcactcat | 7020 |
| ggttatggca gcactgcata attctcttac tgtcatgcca tccgtaagat gcttttctgt | 7080 |
| gactggtgag tactcaacca agtcattctg agaatagtgt atgcggcgac cgagttgctc | 7140 |
| ttgcccggcg tcaatacggg ataataccgc gccacatagc agaactttaa aagtgctcat | 7200 |
| cattggaaaa cgttcttcgg ggcgaaaact ctcaaggatc ttaccgctgt tgagatccag | 7260 |
| ttcgatgtaa cccactcgtg cacccaactg atcttcagca tcttttactt tcaccagcgt | 7320 |
| ttctgggtga gcaaaaacag gaaggcaaaa tgccgcaaaa aagggaataa gggcgacacg | 7380 |
| gaaatgttga atactcatac tcttcctttt tcaatattat tgaagcattt atcagggtta | 7440 |
| ttgtctcatg agcggataca tatttgaatg tatttagaaa aataaacaaa taggggttcc | 7500 |
| gcgcacattt ccccgaaaag tgccacctga cgtctaagaa accattatta tcatgacatt | 7560 |
| aacctataaa aataggcgta tcacgaggcc ctttcgggtc gcgcgtttcg gtgatgacgg | 7620 |
| tgaaaacctc tgacacatgc agctcccgtt gacggtcaca gcttgtctgt aagcggatgc | 7680 |
| cgggagcaga caagcccgtc agggcgcgtc agcgggtgtt ggcgggtgtc ggggctggct | 7740 |
| taactatgcg gcatcagagc agattgtact gagagtgcac cataaaattg taaacgttaa | 7800 |
| tattttgtta aaattcgcgt taaattttg ttaaatcagc tcattttta accaataggc | 7860 |
| cgaaatcggc aaaatccctt ataaatcaaa agaatagccc gagatagggt tgagtgttgt | 7920 |
| tccagtttgg aacaagagtc cactattaaa gaacgtggac tccaacgtca agggcgaaa | 7980 |
| aaccgtctat cagggcgatg gcccactacg tgaaccatca cccaaatcaa gttttttggg | 8040 |
| gtcgaggtgc cgtaaagcac taaatcggaa ccctaaaggg agcccccgat ttagagcttg | 8100 |
| acggggaaag ccggcgaacg tggcgagaaa ggaagggaag aaagcgaaag gagcgggcgc | 8160 |
| tagggcgctg gcaagtgtag cggtcacgct gcgcgtaacc accacacccg ccgcgcttaa | 8220 |
| tgcgccgcta cagggcgcgt actatggttg ctttgacgta tgcggtgtga ataccgcac | 8280 |
| agatgcgtaa ggagaaaata ccgcatcagg cgccattcgc cattcaggct gcgcaactgt | 8340 |
| tgggaagggc gatcggtgcg ggcctcttcg ctattacgcc agctggcgaa agggggatgt | 8400 |
| gctgcaaggc gattaagttg ggtaacgcca gggttttccc agtcacgacg ttgtaaaacg | 8460 |
| acggccagtg aattccatgg tctcaacttt c | 8491 |

<210> SEQ ID NO 49
<211> LENGTH: 8476
<212> TYPE: DNA
<213> ORGANISM: Artificial Sequence
<220> FEATURE:
<223> OTHER INFORMATION: Synthetic polynucleotide

<400> SEQUENCE: 49

| | |
|---|---|
| gaattcccat tgcatacgtt gtatccatat cataatatgt acatttatat tggctcatgt | 60 |
| ccaacattac cgccatgttg acattgatta ttgactagtt attaatagta atcaattacg | 120 |

```
gggtcattag ttcatagccc atatatggag ttccgcgtta cataacttac ggtaaatggc    180
ccgcctggct gaccgcccaa cgaccccgc ccattgacgt caataatgac gtatgttccc     240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta taagcaga     660 gctcgtttag tgaaccgtca gatcgcctgg agacgccatc cacgctgttt tgacctccat    720
agaagacacc gggaccgatc cagcctccgt taacggtgga gggcagtgta gtctgagcag    780
tactcgttgc tgccgcgcgc gccaccagac ataatagctg acagactaac agactgttcc    840
tttccatggg tcttttctgc agtcaccgtc gtcgacacgt gtgatcagat atcgcggccg    900
ccaccatgtt cccgttccag ccaatgtatc cgatgcagcc aatgccctat cgcaacccgt    960
tcgcggcccc gcgcaggccc tggttcccca gaaccgaccc ttttctggcg atgcaggtgc   1020
aggaattaac ccgctcgatg gctaacctga cgttcaagca acgccgggac gcgccacctg   1080
aggggccatc cgctaataaa ccgaagaagg aggcctcgca aaaacagaaa ggggaggcc    1140 aagggaagaa gaagaagaac caagggaaga agaaggctaa gacagggccg cctaatccga   1200
aggcacagaa tggaaacaag aagaagacca acaagaaacc aggcaagaga cagcgcatgg   1260
tcatgaaatt ggaatctgac aagacgttcc caatcatgtt ggaagggaag ataaacggct   1320
acgcttgtgt ggtcggaggg aagttattca ggccgatgca tgtggaaggc aagatcgaca   1380
acgacgttct ggccgcgctt aagacgaaga agcatccaa atacgatctt gagtatgcag    1440
atgtgccaca gaacatgcgg gccgatacat tcaaatacac ccatgagaaa ccccaaggct   1500
attacagctg gcatcatgga gcagtccaat atgaaaatgg gcgtttcacg gtgccgaaag   1560
gagttggggc aagggagac agcggacgac ccattctgga taaccaggga cgggtggtcg    1620
ctattgtgct gggaggtgtg aatgaaggat ctaggacagc cctttcagtc gtcatgtgga   1680
acgagaaggg agttaccgtg aagtatactc cagagaactg cgagcaatgg tcactagtga   1740
ccaccatgtg tctgctcgcc aatgtgacgt tcccatgtgc tcaaccacca atttgctacg   1800
acagaaaacc agcagagact ttggccatgc tcagcgttaa cgttgacaac ccgggctacg   1860
atgagctgct ggaagcagct gttaagtgcc ccggaaggaa aaggagatcc accgaggagc   1920
tgtttaatga gtataagcta acgcgccctt acatggccag atgcatcaga tgtgcagttg   1980
ggagctgcca tagtccaata gcaatcgagg cagtaaagag cgacgggcac gacggttatg   2040
ttagacttca gacttcctcg cagtatggcc tggattcctc cggcaactta aagggcagga   2100
ccatgcggta tgacatgcac gggaccatta agagataccc actacatcaa gtgtcactct   2160
atacatctcg cccgtgtcac attgtggatg ggcacggtta tttcctgctt gccaggtgcc   2220
cggcagggga ctccatcacc atggaattta gaaagattc cgtcagacac tcctgctcgg    2280
tgccgtatga agtgaaattt aatcctgtag gcagagaact ctatactcat cccccagaac   2340
acggagtaga gcaagcgtgc caagtctacg cacatgatgc acagaacaga ggagcttatg   2400
tcgagatgca cctcccgggc tcagaagtgg acagcagttt ggtttccttg agcggcagtt   2460
```

```
ccggaggcgg cgccatcagc ctgcacccca aggccaagat cgaggaatct ggatcctcag    2520
tcaccgtgac acctcctgat gggactagcg ccctggtgga atgcgagtgt ggcggcacaa    2580
agatctccga gaccatcaac aagacaaaac agttcagcca gtgcacaaag aaggagcagt    2640
gcagagcata tcggctgcag aacgataagt gggtgtataa ttctgacaaa ctgcccaaag    2700
cagcgggagc caccttaaaa ggaaaactgc atgtcccatt cttgctggca gacggcaaat    2760
gcaccgtgcc tctagcacca gaacctatga taaccttcgg tttcagatca gtgtcactga    2820
aactgcaccc taagaatccc acatatctaa tcacccgcca acttgctgat gagcctcact    2880
acacgcacga gctcatatct gaaccagctg ttaggaattt taccgtcacc gaaaaagggt    2940
gggagtttgt atggggaaac cacccgccga aaaggttttg ggcacaggaa acagcacccg    3000
gaaatccaca tgggctaccg cacgaggtga taactcatta ttaccacaga taccctatgt    3060
ccaccatcct gggtttgtca atttgtgccg ccattgcaac cgtttccgtt gcagcgtcta    3120
cctggctgtt ttgcagatca agagttgcgt gcctaactcc ttaccggcta cacctaacg    3180 ctaggatacc attttgtctg gctgtgcttt gctgcgcccg cactgccgg gccgagacca    3240 cctgggagtc cttggatcac ctatggaaca ataaccaaca gatgttctgg attcaattgc    3300
tgatccctct ggccgccttg atcgtagtga ctcgcctgct caggtgcgtg tgctgtgtcg    3360
tgcctttttt agtcatggcc ggcgccgcag gcgccggcgc ctacgagcac gcgaccacga    3420
tgccgagcca agcgggaatc tcgtataaca ctatagtcaa cagagcaggc tacgcaccac    3480
tccctatcag cataacacca acaaagatca agctgatacc tacagtgaac ttggagtacg    3540
tcacctgcca ctacaaaaca ggaatggatt caccagccat caaatgctgc ggatctcagg    3600
aatgcactcc aacttacagg cctgatgaac agtgcaaagt cttcacaggg gtttacccgt    3660
tcatgtgggg tggtgcatat tgcttttgcg acactgagaa cacccaagtc agcaaggcct    3720
acgtaatgaa atctgacgac tgccttgcgg atcatgctga agcatataaa gcgcacacag    3780
cctcagtgca ggcgttcctc aacatcacag tgggagaaca ctctattgtg actaccgtgt    3840
atgtgaatgg agaaactcct gtgaatttca atggggtcaa ataactgca ggtccgcttt    3900 ccacagcttg acacccttt gatcgcaaaa tcgtgcagta tgccggggag atctataatt    3960
atgattttcc tgagtatggg gcaggacaac caggagcatt tggagatata caatccagaa    4020
cagtctcaag ctctgatctg tatgccaata ccaacctagt gctgcagaga cccaaagcag    4080
gagcgatcca cgtgccatac actcaggcac cttcgggttt tgagcaatgg aagaaagata    4140
aagctccatc attgaaattt accgcccctt tcggatgcga aatatataca aaccccattc    4200
gcgccgaaaa ctgtgctgta gggtcaattc cattagcctt tgacattccc gacgccttgt    4260
tcaccagggt gtcagaaaca ccgacacttt cagcggccga atgcactctt aacgagtgcg    4320
tgtattcttc cgactttggt gggatcgcca cggtcaagta ctcggccagc aagtcaggca    4380
agtgcgcagt ccatgtgcca tcagggactg ctaccctaaa agaagcagca gtcgagctaa    4440
ccgagcaagg gtcggcgact atccatttct cgaccgcaaa tatccaccg gagttcaggc    4500 tccaaatatg cacatcatat gttacgtgca aggtgattg tcaccccccg aaagaccata    4560
ttgtgacaca ccctcagtat cacgcccaaa catttacagc cgcggtgtca aaaccgcgt    4620 ggacgtggtt aacatccctg ctgggaggat cagccgtaat tattataatt ggcttggtgc    4680
tggctactat tgtggccatg tacgtgctga ccaaccagaa acataattaa ggatctagat    4740
ctgctgtgcc ttctagttgc cagccatctg ttgtttgccc ctcccccgtg ccttccttga    4800
ccctggaagg tgccactccc actgtccttt cctaataaaa tgaggaaatt gcatcgcatt    4860
```

```
gtctgagtag gtgtcattct attctggggg gtggggtggg gcaggacagc aaggggggagg   4920 attgggaaga caatagcagg catgctgggg atgcggtggg ctctatgggt acccaggtgc    4980
tgaagaattg acccggttcc tcctgggcca gaaagaagca ggcacatccc cttctctgtg    5040
acacaccctg tccacgcccc tggttcttag ttccagcccc actcatagga cactcatagc    5100
tcaggagggc tccgccttca atcccacccg ctaaagtact tggagcggtc tctccctccc    5160
tcatcagccc accaaaccaa acctagcctc aagagtgggg aagaaattaa agcaagatag    5220
gctattaagt gcagagggag agaaaatgcc tccaacatgt gaggaagtaa tgagagaaat    5280
catagaattt taaggccatg atttaaggcc atcatggcct aagcttgaaa ggagatagga    5340
tcaaagcttg gcgtaatcat ggtcatagct gtttcctgtg tgaaattgtt atccgctcac    5400
aattccacac aacatacgag ccggaagcat aaagtgtaaa gcctggggtg cctaatgagt    5460
gagctaactc acattaattg cgttgcgctc actgcccgct ttccagtcgg gaaacctgtc    5520
gtgccagctg cattaatgaa tcggccaacg cgcggggaga ggcggtttgc gtattgggcg    5580
ctcttccgct tcctcgctca ctgactcgct gcgctcggtc gttcggctgc ggcgagcggt    5640
atcagctcac tcaaaggcgg taatacggtt atccacagaa tcaggggata acgcaggaaa    5700
gaacatgtga gcaaaaggcc agcaaaaggc caggaaccgt aaaaaggccg cgttgctggc    5760
gtttttccat aggctccgcc cccctgacga gcatcacaaa aatcgacgct caagtcagag    5820
gtggcgaaac ccgacaggac tataaagata ccaggcgttt ccccctggaa gctccctcgt    5880
gcgctctcct gttccgaccc tgccgcttac cggatacctg tccgcctttc tcccttcggg    5940
aagcgtggcg ctttctcata gctcacgctg taggtatctc agttcggtgt aggtcgttcg    6000
ctccaagctg ggctgtgtgc acgaaccccc cgttcagccc gaccgctgcg ccttatccgg    6060
taactatcgt cttgagtcca acccggtaag acacgactta tcgccactgg cagcagccac    6120
tggtaacagg attagcagag cgaggtatgt aggcggtgct acagagttct tgaagtggtg    6180
gcctaactac ggctacacta agaacagt atttggtatc tgcgctctgc tgaagccagt    6240
taccttcgga aaaagagttg gtagctcttg atccggcaaa caaaccaccg ctggtagcgg    6300 tggtttttt gtttgcaagc agcagattac gcgcagaaaa aaaggatctc aagaagatcc    6360
tttgatcttt tctacggggt ctgacgctca gtggaacgaa aactcacgtt aagggatttt    6420
ggtcatgaga ttatcaaaaa ggatcttcac ctagatcctt ttaaattaaa aatgaagttt    6480
taaatcaatc taaagtatat atgagtaaac ttggtctgac agttaccaat gcttaatcag    6540
tgaggcacct atctcagcga tctgtctatt tcgttcatcc atagttgcct gactccccgt    6600
cgtgtagata actacgatac gggagggctt accatctggc cccagtgctg caatgatacc    6660
gcgagaacca cgctcaccgg ctccagattt atcagcaata aaccagccag ccggaagggc    6720
cgagcgcaga agtggtcctg caactttatc cgcctccatc cagtctatta attgttgccg    6780
ggaagctaga gtaagtagtt cgccagttaa tagtttcgcg aacgttgttg ccattgctac    6840
aggcatcgtg gtgtcacgct cgtcgtttgg tatggcttca ttcagctccg gttcccaacg    6900
atcaaggcga gttacatgat cccccatgtt gtgcaaaaaa gcggttagct ccttcggtcc    6960
tccgatcgtt gtcagaagta agttggccgc agtgttatca ctcatggtta tggcagcact    7020
gcataattct cttactgtca tgccatccgt aagatgcttt tctgtgactg gtgagtactc    7080
aaccaagtca ttctgagaat agtgtatgcg gcgaccgagt tgctcttgcc cggcgtcaat    7140
acgggataat accgcgccac atagcagaac tttaaaagtg ctcatcattg gaaaacgttc    7200
```

| | |
|---|---|
| ttcggggcga aaactctcaa ggatcttacc gctgttgaga tccagttcga tgtaacccac | 7260 |
| tcgtgcaccc aactgatctt cagcatcttt tactttcacc agcgtttctg ggtgagcaaa | 7320 |
| aacaggaagg caaaatgccg caaaaaggg aataagggcg acacggaaat gttgaatact | 7380 |
| catactcttc cttttcaat attattgaag catttatcag ggttattgtc tcatgagcgg | 7440 |
| atacatattt gaatgtattt agaaaaataa acaaataggg gttccgcgca catttccccg | 7500 |
| aaaagtgcca cctgacgtct aagaaaccat tattatcatg acattaacct ataaaaatag | 7560 |
| gcgtatcacg aggccctttc gggtcgcgcg tttcggtgat gacggtgaaa acctctgaca | 7620 |
| catgcagctc ccgttgacgg tcacagcttg tctgtaagcg gatgccggga gcagacaagc | 7680 |
| ccgtcagggc gcgtcagcgg gtgttggcgg gtgtcggggc tggcttaact atgcggcatc | 7740 |
| agagcagatt gtactgagag tgcaccataa aattgtaaac gttaatattt tgttaaaatt | 7800 |
| cgcgttaaat ttttgttaaa tcagctcatt ttttaaccaa taggccgaaa tcggcaaaat | 7860 |
| cccttataaa tcaaaagaat agcccgagat agggttgagt gttgttccag tttggaacaa | 7920 |
| gagtccacta ttaaagaacg tggactccaa cgtcaaaggg cgaaaaaccg tctatcaggg | 7980 |
| cgatggccca ctacgtgaac catcacccaa atcaagtttt ttggggtcga ggtgccgtaa | 8040 |
| agcactaaat cggaacccta aagggagccc ccgatttaga gcttgacggg gaaagccggc | 8100 |
| gaacgtggcg agaaaggaag ggaagaaagc gaaaggagcg ggcgctaggg cgctggcaag | 8160 |
| tgtagcggtc acgctgcgcg taaccaccac acccgccgcg cttaatgcgc cgctacaggg | 8220 |
| cgcgtactat ggttgctttg acgtatgcgg tgtgaaatac cgcacagatg cgtaaggaga | 8280 |
| aaataccgca tcaggcgcca ttcgccattc aggctgcgca actgttggga agggcgatcg | 8340 |
| gtgcgggcct cttcgctatt acgccagctg gcgaaagggg gatgtgctgc aaggcgatta | 8400 |
| agttgggtaa cgccagggtt ttcccagtca cgacgttgta aaacgacggc cagtgaattc | 8460 |
| catggtctca actttc | 8476 |

<210> SEQ ID NO 50
<211> LENGTH: 7290
<212> TYPE: DNA
<213> ORGANISM: Artificial Sequence
<220> FEATURE:
<223> OTHER INFORMATION: Synthetic polynucleotide

<400> SEQUENCE: 50

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg gatgtgctg caaggcgatt aagttgggta acgccagggt | 360 |
| tttcccagtc acgacgttgt aaaacgacgg ccagtgaatt gacgcgtgtt ggcattgatt | 420 |
| attgactagt tattaatagt aatcaattac ggggtcatta gttcatagcc catatatgga | 480 |
| gttccgcgtt acataactta cggtaaatgg cccgcctggc tgaccgccca acgacccccg | 540 |
| cccattgacg tcaataatga cgtatgttcc catagtaacg ccaataggga ctttccattg | 600 |
| acgtcaatgg gtggagtatt tacggtaaac tgcccacttg gcagtacatc aagtgtatca | 660 |
| tatgccaagt acgccccta ttgacgtcaa tgacggtaaa tggcccgcct ggcattatgc | 720 |
| ccagtacatg accttatggg actttcctac ttggcagtac atctacgtat tagtcatcgc | 780 |

```
tattaccatg gtgatgcggt tttggcagta catcaatggg cgtggatagc ggtttgactc      840
acggggattt ccaagtctcc accccattga cgtcaatggg agtttgtttt ggcaccaaaa      900
tcaacgggac tttccaaaat gtcgtaacaa ctccgcccca ttgacgcaaa tgggcggtag      960
gcgtgtacgg tgggaggtct atataagcag agctcgttta gtgaaccgtc agataactgc     1020
aggtcgacga tatcgcggcc gccaccatgt tcccgttcca gccaatgtat ccgatgcagc     1080
caatgcccta tcgcaacccg ttcgcggccc gcgcaggcc ctggttcccc agaaccgacc      1140
cttttctggc gatgcaggtg caggaattaa cccgctcgat ggctaacctg acgttcaagc     1200
aacgccggga cgcgccacct gagggggccat ccgctaataa accgaagaag gaggcctcgc    1260
aaaaacagaa agggggaggc caagggaaga agaagaagaa ccaagggaag aagaaggcta     1320
agacagggcc gcctaatccg aaggcacaga atggaaacaa gaagaagacc aacaagaaac     1380
caggcaagag acagcgcatg gtcatgaaat tggaatctga caagacgttc ccaatcatgt     1440
tggaagggaa gataaacggc tacgcttgtg tggtcggagg gaagttattc aggccgatgc     1500
atgtggaagg caagatcgac aacgacgttc tggccgcgct taagacgaag aaagcatcca     1560
aatacgatct tgagtatgca gatgtgccac agaacatgcg ggccgataca ttcaaataca     1620
cccatgagaa accccaaggc tattacagct ggcatcatgg agcagtccaa tatgaaaatg     1680
ggcgtttcac ggtgccgaaa ggagttgggg ccaagggaga cagcggacga cccattctgg     1740
ataaccaggg acgggtggtc gctattgtgc tgggaggtgt gaatgaagga tctaggacag     1800
ccctttcagt cgtcatgtgg aacgagaagg gagttaccgt gaagtatact ccagagaact     1860
gcgagcaatg gtcactagtg accaccatgt gtctgctcgc caatgtgacg ttcccatgtg     1920
ctcaaccacc aatttgctac gacagaaaac cagcagagac tttggccatg ctcagcgtta     1980
acgttgacaa cccgggctac gatgagctgc tggaagcagc tgttaagtgc cccggaagga     2040
aaaggagatc caccgaggag ctgtttaatg agtataagct aacgcgccct acatggccca     2100
gatgcatcag atgtgcagtt gggagctgcc atagtccaat agcaatcgag gcagtaaaga     2160
gcgacgggca cgacggttat gttagacttc agacttcctc gcagtatggc ctggattcct     2220
ccggcaactt aaagggcagg accatgcggt atgacatgca cgggaccatt aaagagatac     2280
cactacatca agtgtcactc tatacatctc gcccgtgtca cattgtggat gggcacggtt     2340
atttcctgct tgccaggtgc ccggcagggg actccatcac catggaattt aagaaagatt     2400
ccgtcagaca ctcctgctcg gtgccgtatg aagtgaaatt taatcctgta ggcagagaac     2460
tctatactca tccccagaa cacgcgagtag agcaagcgtg ccaagtctac gcacatgatg     2520
cacagaacag aggagcttat gtcgagatgc acctcccggg ctcagaagtg gacagcagtt     2580
tggtttcctt gagcggcagt tccggaggct gcatcatcag ctacgcgga gccgactact     2640 gcggcggatc ctcagtcacc gtgacacctc ctgatgggac tagcgccctg gtggaatgcg     2700
agtgtggcgg cacaaagatc tccgagacca tcaacaagac aaaacagttc agccagtgca     2760
caaagaagga gcagtgcaga gcatatcggc tgcagaacga taagtgggtg tataattctg     2820
acaaactgcc caaagcagcg ggagccacct taaaaggaaa actgcatgtc ccattcttgc     2880
tggcagacgg caaatgcacc gtgcctctag caccagaacc tatgataacc ttcggttca     2940 gatcagtgtc actgaaactg caccctaaga atccccacata tctaatcacc cgccaacttg    3000 ctgatgagc tcactacacg cacgagctca tatctgaacc agctgttagg aattttaccg      3060
tcaccgaaaa agggtgggag tttgtatggg gaaaccaccc gccgaaaagg ttttgggcac     3120
```

| | |
|---|---|
| aggaaacagc acccggaaat ccacatgggc taccgcacga ggtgataact cattattacc | 3180 |
| acagataccc tatgtccacc atcctgggtt tgtcaatttg tgccgccatt gcaaccgttt | 3240 |
| ccgttgcagc gtctacctgg ctgttttgca gatcaagagt tgcgtgccta actccttacc | 3300 |
| ggctaacacc taacgctagg ataccatttt gtctggctgt gctttgctgc gcccgcactg | 3360 |
| cccgggccga gaccacctgg gagtccttgg atcacctatg aacaataac caacagatgt | 3420 |
| tctggattca attgctgatc cctctggccg ccttgatcgt agtgactcgc ctgctcaggt | 3480 |
| gcgtgtgctg tgtcgtgcct tttttagtca tggccggcgc cgcaggcgcc ggcgcctacg | 3540 |
| agcacgcgac cacgatgccg agccaagcgg gaatctcgta taacactata gtcaacagag | 3600 |
| caggctacgc accactccct atcagcataa caccaacaaa gatcaagctg atacctacag | 3660 |
| tgaacttgga gtacgtcacc tgccactaca aaacaggaat ggattcacca gccatcaaat | 3720 |
| gctgcggatc tcaggaatgc actccaactt acaggcctga tgaacagtgc aaagtcttca | 3780 |
| caggggttta cccgttcatg tggggtggtg catattgctt ttgcgacact gagaacaccc | 3840 |
| aagtcagcaa ggcctacgta atgaaatctg acgactgcct tgcggatcat gctgaagcat | 3900 |
| ataaagcgca cacagcctca gtgcaggcgt tcctcaacat cacagtggga gaacactcta | 3960 |
| ttgtgactac cgtgtatgtg aatggagaaa ctcctgtgaa tttcaatggg gtcaaaataa | 4020 |
| ctgcaggtcc gctttccaca gcttggacac ccttttgatcg caaaatcgtg cagtatgccg | 4080 |
| gggagatata taattatgat tttcctgagt atggggcagg acaaccagga gcatttggag | 4140 |
| atatacaatc cagaacagtc tcaagctctg atctgtatgc caataccaac ctagtgctgc | 4200 |
| agagacccaa agcaggagcg atccacgtgc catacactca ggcaccttcg ggttttgagc | 4260 |
| aatggaagaa agataaagct ccatcattga atttaccgc ccctttcgga tgcgaaatat | 4320 |
| atacaaaccc cattcgcgcc gaaaactgtg ctgtagggtc aattccatta gccttttgaca | 4380 |
| ttcccgacgc cttgttcacc agggtgtcag aaacaccgac actttcagcg gccgaatgca | 4440 |
| ctcttaacga gtgcgtgtat tcttccgact ttggtgggat cgccacggtc aagtactcgg | 4500 |
| ccagcaagtc aggcaagtgc gcagtccatg tgccatcagg gactgctacc ctaaaagaag | 4560 |
| cagcagtcga gctaaccgag caagggtcgg cgactatcca tttctcgacc gcaaatatcc | 4620 |
| acccggagtt caggctccaa atatgcacat catatgttac gtgcaaaggt gattgtcacc | 4680 |
| cccgaaaga ccatattgtg acacaccctc agtatcacgc ccaaacattt acagccgcgg | 4740 |
| tgtcaaaaac cgcgtggacg tggttaacat ccctgctggg aggatcagcc gtaattatta | 4800 |
| taattggctt ggtgctggct actattgtgg ccatgtacgt gctgaccaac cagaaacata | 4860 |
| attaaggatc tagatctgct gtgccttcta gttgccagcc atctgttgtt tgcccctccc | 4920 |
| ccgtgccttc cttgaccctg gaaggtgcca ctcccactgt cctttcctaa taaaatgagg | 4980 |
| aaattgcatc gcattgtctg agtaggtgtc attctattct ggggggtggg gtggggcagg | 5040 |
| acagcaaggg ggaggattgg gaagacaata gcaggcatgc tggggatgcg gtgggctcta | 5100 |
| tggctcgagc atggtcatag ctgtttcctg tgtgaaattg ttatccgctc acaattccac | 5160 |
| acaacatacg agccggaagc ataaagtgta aagcctgggg tgcctaatga gtgagctaac | 5220 |
| tcacattaat tgcgttgcgc tcactgcccg ctttccagtc gggaaacctg tcgtgccagc | 5280 |
| tgcattaatg aatcggccaa cgcgcgggga gaggcggttt gcgtattggg cgctcttccg | 5340 |
| cttcctcgct cactgactcg ctgcgctcgg tcgttcggct gcggcgagcg gtatcagctc | 5400 |
| actcaaaggc ggtaatacgg ttatccacag aatcagggga taacgcagga aagaacatgt | 5460 |
| gagcaaaagg ccagcaaaag gccaggaacc gtaaaaaggc cgcgttgctg cgttttttcc | 5520 |

```
ataggctccg ccccccctgac gagcatcaca aaaatcgacg ctcaagtcag aggtggcgaa    5580
acccgacagg actataaaga taccaggcgt ttccccctgg aagctccctc gtgcgctctc    5640
ctgttccgac cctgccgctt accggatacc tgtccgcctt tctcccttcg ggaagcgtgg    5700
cgctttctca tagctcacgc tgtaggtatc tcagttcggt gtaggtcgtt cgctccaagc    5760
tgggctgtgt gcacgaaccc cccgttcagc ccgaccgctg cgccttatcc ggtaactatc    5820
gtcttgagtc caacccggta agacacgact tatcgccact ggcagcagcc actggtaaca    5880
ggattagcag agcgaggtat gtaggcggtg ctacagagtt cttgaagtgg tggcctaact    5940
acggctacac tagaagaaca gtatttggta tctgcgctct gctgaagcca gttaccttcg    6000
gaaaaagagt tggtagctct tgatccggca acaaaccac cgctggtagc ggtggttttt     6060
ttgtttgcaa gcagcagatt acgcgcagaa aaaaggatc tcaagaagat cctttgatct     6120
tttctacggg gtctgacgct cagtggaacg aaaactcacg ttaagggatt ttggtcatga    6180
gattatcaaa aaggatcttc acctagatcc ttttaaatta aaaatgaagt tttaaatcaa    6240
tctaaagtat atatgagtaa acttggtctg acagttagaa aaactcatcg agcatcaaat    6300
gaaactgcaa tttattcata tcaggattat caataccata tttttgaaaa agccgtttct    6360
gtaatgaagg agaaaactca ccgaggcagt tccataggat ggcaagatcc tggtatcggt    6420
ctgcgattcc gactcgtcca acatcaatac aacctattaa tttcccctcg tcaaaaataa    6480
ggttatcaag tgagaaatca ccatgagtga cgactgaatc cggtgagaat ggcaaaagtt    6540
tatgcatttc tttccagact tgttcaacag gccagccatt acgctcgtca tcaaaatcac    6600
tcgcatcaac caaaccgtta ttcattcgtg attgcgcctg agcgagacga atacgcgat    6660 cgctgttaaa aggacaatta caaacaggaa tcgaatgcaa ccggcgcagg aacactgcca    6720
gcgcatcaac aatattttca cctgaatcag gatattcttc taatacctgg aatgctgttt    6780
tcccagggat cgcagtggtg agtaaccatg catcatcagg agtacggata aaatgcttga    6840
tggtcggaag aggcataaat tccgtcagcc agtttagtct gaccatctca tctgtaacat    6900
cattggcaac gctacctttg ccatgtttca gaaacaactc tggcgcatcg gcttcccat     6960 acaatcgata gattgtcgca cctgattgcc cgacattatc gcgagcccat ttatacccat    7020
ataaatcagc atccatgttg gaatttaatc gcggcctaga gcaagacgtt tcccgttgaa    7080
tatggctcat actcttcctt tttcaatatt attgaagcat ttatcagggt tatttgtctca   7140 tgagcggata catatttgaa tgtatttaga aaaataaaca ataggggtt ccgcgcacat    7200 ttccccgaaa agtgccacct gacgtctaag aaaccattat tatcatgaca ttaacctata    7260
aaaataggcg tatcacgagg ccctttcgtc                                     7290
```

<210> SEQ ID NO 51
<211> LENGTH: 72
<212> TYPE: DNA
<213> ORGANISM: Artificial Sequence
<220> FEATURE:
<223> OTHER INFORMATION: Synthetic polynucleotide

<400> SEQUENCE: 51

```
tccggaggac taaactggta ccgcatgagc cccagcaacc agacggacaa gctggccgcc    60
ttcggaggat cc                                                         72
```

<210> SEQ ID NO 52
<211> LENGTH: 24
<212> TYPE: PRT

```
<213> ORGANISM: Artificial Sequence
<220> FEATURE:
<223> OTHER INFORMATION: Synthetic peptide

<400> SEQUENCE: 52

Ser Gly Gly Leu Asn Trp Tyr Arg Met Ser Pro Ser Asn Gln Thr Asp
1               5                   10                  15

Lys Leu Ala Ala Phe Gly Gly Ser
            20

<210> SEQ ID NO 53
<211> LENGTH: 78
<212> TYPE: DNA
<213> ORGANISM: Artificial Sequence
<220> FEATURE:
<223> OTHER INFORMATION: Synthetic polynucleotide

<400> SEQUENCE: 53
tccggaggaa tgctaaactg gtaccgcatg agccccagca accagacgga caagctggcc    60
gccttctcag gaggatcc                                                  78

<210> SEQ ID NO 54
<211> LENGTH: 26
<212> TYPE: PRT
<213> ORGANISM: Artificial Sequence
<220> FEATURE:
<223> OTHER INFORMATION: Synthetic peptide

<400> SEQUENCE: 54

Ser Gly Gly Met Leu Asn Trp Tyr Arg Met Ser Pro Ser Asn Gln Thr
1               5                   10                  15

Asp Lys Leu Ala Ala Phe Ser Gly Gly Ser
            20                  25

<210> SEQ ID NO 55
<211> LENGTH: 78
<212> TYPE: DNA
<213> ORGANISM: Artificial Sequence
<220> FEATURE:
<223> OTHER INFORMATION: Synthetic polynucleotide

<400> SEQUENCE: 55
tccggaggag tgctaaactg gtaccgcatg agccccagca accagacgga caagctggcc    60
gccttccccg gaggatcc                                                  78

<210> SEQ ID NO 56
<211> LENGTH: 26
<212> TYPE: PRT
<213> ORGANISM: Artificial Sequence
<220> FEATURE:
<223> OTHER INFORMATION: Synthetic peptide

<400> SEQUENCE: 56

Ser Gly Gly Val Leu Asn Trp Tyr Arg Met Ser Pro Ser Asn Gln Thr
1               5                   10                  15

Asp Lys Leu Ala Ala Phe Pro Gly Gly Ser
            20                  25

<210> SEQ ID NO 57
<211> LENGTH: 48
<212> TYPE: DNA
<213> ORGANISM: Artificial Sequence
<220> FEATURE:
<223> OTHER INFORMATION: Synthetic polynucleotide
```

```
<400> SEQUENCE: 57
tccggaggat gcatcatcag ctacggcgga gccgactacg aggatcc            48

<210> SEQ ID NO 58
<211> LENGTH: 17
<212> TYPE: PRT
<213> ORGANISM: Artificial Sequence
<220> FEATURE:
<223> OTHER INFORMATION: Synthetic peptide

<400> SEQUENCE: 58

Ser Gly Gly Cys Ile Ile Ser Tyr Gly Gly Ala Asp Tyr Cys Gly Gly
1               5                   10                  15
Ser

<210> SEQ ID NO 59
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 59
tccggaggag gcgccatcag cctgcacccc aaggccaaga tcgaggaatc tggaggatcc     60

<210> SEQ ID NO 60
<211> LENGTH: 19
<212> TYPE: PRT
<213> ORGANISM: Artificial Sequence
<220> FEATURE:
<223> OTHER INFORMATION: Synthetic peptide

<400> SEQUENCE: 60

Ser Gly Gly Gly Ala Ile Ser Leu His Pro Lys Ala Lys Ile Glu Glu
1               5                   10                  15
Ser Gly Ser

<210> SEQ ID NO 61
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 61
tccggaggat gtggcgccat cagcctgcac cccaaggcca agatcgagga aggaggatcc     60

<210> SEQ ID NO 62
<211> LENGTH: 21
<212> TYPE: PRT
<213> ORGANISM: Artificial Sequence
<220> FEATURE:
<223> OTHER INFORMATION: Synthetic peptide

<400> SEQUENCE: 62

Ser Gly Gly Cys Gly Ala Ile Ser Leu His Pro Lys Ala Lys Ile Glu
1               5                   10                  15
Glu Cys Gly Gly Ser
            20

<210> SEQ ID NO 63
<211> LENGTH: 3747
<212> TYPE: DNA
```

<213> ORGANISM: Chikungunya virus

<400> SEQUENCE: 63

| | | | | | |
|---|---|---|---|---|---|
| atggagttca | tcccaaccca | aacttttac | aataggaggt | accagcctcg | accctggact | 60 |
| ccgcgccta | ctatccaagt | catcaggccc | agaccgcgcc | ctcagaggca | agctgggcaa | 120 |
| cttgcccagc | tgatctcagc | agttaataaa | ctgacaatgc | gcgcggtacc | acaacagaag | 180 |
| ccacgcagga | atcggaagaa | taagaagcaa | aagcaaaaac | aacaggcgcc | acaaaacaac | 240 |
| acaaatcaaa | agaagcagcc | acctaaaaag | aaaccggctc | aaaagaaaaa | gagccgggc | 300 |
| cgcagagaga | ggatgtgcat | gaaaatcgaa | aatgattgta | ttttcgaagt | caagcacgaa | 360 |
| ggtaaggtaa | caggttacgc | gtgcctggtg | ggggacaaag | taatgaaacc | agcacacgta | 420 |
| aaggggacca | tcgataacgc | ggacctggcc | aaactggcct | ttaagcggtc | atctaagtat | 480 |
| gaccttgaat | gcgcgcagat | acccgtgcac | atgaagtccg | acgcttcgaa | gttcacccat | 540 |
| gagaaaccgg | aggggtacta | caactggcac | cacggagcag | tacagtactc | aggaggccgg | 600 |
| ttcaccatcc | ctacaggtgc | tggcaaacca | ggggacagcg | gcagaccgat | cttcgacaac | 660 |
| aagggacgcg | tggtggccat | agtcttagga | ggagctaatg | aaggagcccg | tacagccctc | 720 |
| tcggtggtga | cctggaataa | agacattgtc | actaaaatca | cccccgaggg | ggccgaagag | 780 |
| tggagtcttg | ccatcccagt | tatgtgcctg | ttggcaaaca | ccacgttccc | ctgctcccag | 840 |
| ccccttgca | cgccctgctg | ctacgaaaag | gaaccggagg | aaaccctacg | catgcttgag | 900 |
| gacaacgtca | tgagacctgg | gtactatcag | ctgctacaag | catccttaac | atgttctccc | 960 |
| caccgccagc | gacgcagcac | caaggacaac | ttcaatgtct | ataaagccac | aagaccatac | 1020 |
| ttagctcact | gtcccgactg | tggagaaggg | cactcgtgcc | atagtcccgt | agcactagaa | 1080 |
| cgcatcagaa | atgaagcgac | agacgggacg | ctgaaaatcc | aggtctcctt | gcaaatcgga | 1140 |
| ataaagacgg | atgacagcca | cgattggacc | aagctgcgtt | atatggacaa | ccacatgcca | 1200 |
| gcagacgcag | agagggcggg | gctatttgta | agaacatcag | caccgtgtac | gattactgga | 1260 |
| acaatgggac | acttcatcct | ggcccgatgt | ccaaagggg | aaactctgac | ggtgggattc | 1320 |
| actgacagta | ggaagattag | tcactcatgt | acgcacccat | tcaccacga | ccctcctgtg | 1380 |
| ataggtcggg | aaaaattcca | ttcccgaccg | cagcacggta | aagagctacc | ttgcagcacg | 1440 |
| tacgtgcaga | gcaccgccgc | aactaccgag | gagatagagg | tacacatgcc | cccagacacc | 1500 |
| cctgatcgca | cattaatgtc | acaacagtcc | ggcaacgtaa | agatcacagt | caatggccag | 1560 |
| acggtgcggt | acaagtgtaa | ttgcggtggc | tcaaatgaag | gactaacaac | tacagacaaa | 1620 |
| gtgattaata | actgcaaggt | tgatcaatgt | catgccgcgg | tcaccaatca | caaaaagtgg | 1680 |
| cagtataact | cccctctggt | cccgcgtaat | gctgaacttg | ggaccgaaa | aggaaaaatt | 1740 |
| cacatcccgt | ttccgctggc | aaatgtaaca | tgcagggtgc | ctaaagcaag | gaaccccacc | 1800 |
| gtgacgtacg | ggaaaaacca | agtcatcatg | ctactgtatc | ctgaccaccc | aacactcctg | 1860 |
| tcctaccgga | atatgggaga | agaaccaaac | tatcaagaag | agtgggtgat | gcataagaag | 1920 |
| gaagtcgtgc | taaccgtgcc | gactgaaggg | ctcgaggtca | cgtgggcaa | caacgagccg | 1980 |
| tataagtatt | ggccgcagtt | atctacaaac | ggtacagccc | atggccaccc | gcatgagata | 2040 |
| attctgtatt | attatgagct | gtacccact | atgactgtag | tagttgtgtc | agtggccacg | 2100 |
| ttcatactcc | tgtcgatggt | gggtatggca | gcggggatgt | gcatgtgtgc | acgacgcaga | 2160 |
| tgcatcacac | cgtatgaact | gacaccagga | gctaccgtcc | ctttcctgct | tagcctaata | 2220 |
| tgctgcatca | gaacagctaa | agcggccaca | taccaagagg | ctgcgatata | cctgtggaac | 2280 |

```
gagcagcaac ctttgttttg gctacaagcc cttattccgc tggcagccct gattgttcta    2340
tgcaactgtc tgagactctt accatgctgc tgtaaaacgt tggcttttt agccgtaatg     2400 agcgtcggtg cccacactgt gagcgcgtac gaacacgtaa cagtgatccc gaacacggtg    2460
ggagtaccgt ataagactct agtcaataga cctggctaca gccccatggt attggagatg    2520
gaactactgt cagtcacttt ggagccaaca ctatcgcttg attacatcac gtgcgagtac    2580
aaaaccgtca tcccgtctcc gtacgtgaag tgctgcggta cagcagagtg caaggacaaa    2640
aacctacctg actacagctg taaggtcttc accggcgtct acccatttat gtggggcggc    2700
gcctactgct tctgcgacgc tgaaaacacg cagttgagcg aagcacacgt ggagaagtcc    2760
gaatcatgca aaacagaatt tgcatcagca tacagggctc ataccgcatc tgcatcagct    2820
aagctccgcg tcctttacca aggaaataac atcactgtaa ctgccatgc aaacggcgac    2880 catgccgtca cagttaagga cgccaaattc attgtgggc caatgtcttc agcctggaca    2940
cctttcgaca caaaattgt ggtgtacaaa ggtgacgtct ataacatgga ctacccgccc    3000
tttggcgcag gaagaccagg acaatttggc gatatccaaa gtcgcacacc tgagagtaaa    3060
gacgtctatg ctaatacaca actggtactg cagagaccgg ctgtgggtac ggtacacgtg    3120
ccatactctc aggcaccatc tggctttaag tattggctaa agaacgcgg ggcgtcgctg    3180 cagcacacag caccatttgg ctgccaaata gcaacaaacc cggtaagagc ggtgaactgc    3240
gccgtaggga acatgcccat ctccatcgac ataccggaag cggccttcac tagggtcgtc    3300
gacgcgccct ctttaacgga catgtcgtgc gaggtaccag cctgcaccca ttcctcagac    3360 tttggggcg tcgccattat taaatatgca gccagcaaga aggcaagtg tgcggtgcat    3420 tcgatgacta acgccgtcac tattcgggaa gctgagatag aagttgaagg gaattctcag    3480
ctgcaaatct ctttctcgac ggccttagcc agcgccgaat ccgcgtaca agtctgttct    3540 acacaagtac actgtgcagc cgagtgccac ccccgaagg accacatagt caactacccg    3600
gcgtcacata ccaccctcgg ggtccaggac atctccgcta cggcgatgtc atgggtgcag    3660
aagatcacgg gaggtgtggg actggttgtt gctgttgccg cactgattct aatcgtggtg    3720
ctatgcgtgt cgttcagcag gcactaa                                        3747
```

<210> SEQ ID NO 64
<211> LENGTH: 3765
<212> TYPE: DNA
<213> ORGANISM: Venezuelan equine encephalitis virus

<400> SEQUENCE: 64

```
atgttcccgt ccagccaat gtatccgatg cagccaatgc cctatcgcaa cccgttcgcg      60
gccccgcgca ggccctggtt ccccagaacc gaccctttc tggcgatgca ggtgcaggaa     120 ttaaccgct cgatggctaa cctgacgttc aagcaacgcc gggacgcgcc acctgagggg     180
ccatccgcta taaaccgaa gaaggaggcc tcgcaaaaac agaaagggg aggccaaggg      240 aagaagaaga gaaccaagg gaagaagaag gctaagacag ggccgcctaa tcgaaggca      300 cagaatggaa acaagaagaa gaccaacaag aaaccaggca agacacagcg catggtcatg     360
aaattggaat ctgacaagac gttcccaatc atgttggaag ggaagataaa cggctacgct    420
tgtgtggtcg gagggaagtt attcaggccg atgcatgtgg aaggcaagat cgacaacgac    480
gttctggccg cgcttaagac gaagaaagca tccaaatacg atcttgagta tgcagatgtg    540
ccacagaaca tgcgggccga tacattcaaa tacacccatg agaaacccca aggctattac    600
```

```
agctggcatc atggagcagt ccaatatgaa aatgggcgtt tcacggtgcc gaaaggagtt      660
ggggccaagg gagacagcgg acgacccatt ctggataacc agggacgggt ggtcgctatt      720
gtgctgggag gtgtgaatga aggatctagg acagcccttt cagtcgtcat gtggaacgag      780
aagggagtta ccgtgaagta tactccggag aactgcgagc aatggtcact agtgaccacc      840
atgtgtctgc tcgccaatgt gacgttccca tgtgctcaac caccaatttg ctacgacaga      900
aaaccagcag agactttggc catgctcagc gttaacgttg acaacccggg ctacgatgag      960
ctgctggaag cagctgttaa gtgccccgga aggaaaagga gatccaccga ggagctgttt     1020
aatgagtata agctaacgcg cccttacatg gccagatgca tcagatgtgc agttgggagc     1080
tgccatagtc caatagcaat cgaggcagta aagagcgacg ggcacgacgg ttatgttaga     1140
cttcagactt cctcgcagta tggcctggat tcctccggca acttaaaggg caggaccatg     1200
cggtatgaca tgcacgggac cattaaagag ataccactac atcaagtgtc actctataca     1260
tctcgcccgt gtcacattgt ggatgggcac ggttatttcc tgcttgccag gtgcccggca     1320
ggggactcca tcaccatgga atttaagaaa gattccgtca gacactcctg ctcggtgccg     1380
tatgaagtga aatttaatcc tgtaggcaga gaactctata ctcatccccc agaacacgga     1440
gtagagcaag cgtgccaagt ctacgcacat gatgcacaga acagaggagc ttatgtcgag     1500
atgcacctcc cgggctcaga agtggacagc agtttggttt ccttgagcgg cagttcagtc     1560
accgtgacac ctcctgatgg gactagcgcc ctggtggaat gcgagtgtgg cggcacaaag     1620
atctccgaga ccatcaacaa gacaaaacag ttcagccagt gcacaaagaa ggagcagtgc     1680
agagcatatc ggctgcagaa cgataagtgg gtgtataatt ctgacaaact gcccaaagca     1740
gcgggagcca ccttaaaagg aaaactgcat gtcccattct tgctggcaga cggcaaatgc     1800
accgtgcctc tagcaccaga acctatgata accttcggtt tcagatcagt gtcactgaaa     1860
ctgcaccctg agaatcccac atatctaatc cccgccaac ttgctgatga gcctcactac     1920
acgcacgagc tcatatctga accagctgtt aggaatttta ccgtcaccga aaaagggtgg     1980
gagtttgtat ggggaaacca cccgccgaaa aggttttggg cacaggaaac agcacccgga     2040
aatccacatg ggctaccgca cgaggtgata actcattatt accacagata ccctatgtcc     2100
accatcctgg gtttgtcaat ttgtgccgcc attgcaaccg tttccgttgc agcgtctacc     2160
tggctgtttt gcagatctag agttgcgtgc ctaactcctt accggctaac acctaacgct     2220
aggataccat tttgtctggc tgtgcttgc tgcgcccgca ctgcccgggc cgagaccacc     2280
tgggagtcct ggatcaccct atggaacaat aaccaacaga tgttctggat tcaattgctg     2340
atccctctgg ccgccttgat cgtagtgact cgcctgctca ggtgcgtgtg ctgtgtcgtg     2400
ccttttttag tcatggccgg cgccgcaggc gccggcgcct acgagcacgc gaccacgatg     2460
ccgagccaag cgggaatctc gtataacact atagtcaaca gagcaggcta cgcaccactc     2520
cctatcagca taacaccaac aaagatcaag ctgataccta cagtgaactt ggagtacgtc     2580
acctgccact acaaaacagg aatggattca ccagccatca atgctgcgg atctcaggaa     2640
tgcactccaa cttacaggcc tgatgaacag tgcaaagtct tcacaggggt ttacccgttc     2700
atgtggggtg gtgcatattg ctttgcgac actgagaaca cccaagtcag caaggcctac     2760
gtaatgaaat ctgacgactg ccttgcggat catgctgaag catataaagc gcacacagcc     2820
tcagtgcagg cgttcctcaa catcacagtg ggagaacact ctattgtgac taccgtgtat     2880
gtgaatggag aaactcctgt gaatttcaat ggggtcaaaa taactgcagg tccgcttccc     2940
acagcttgga caccctttga tcgcaaaatc gtgcagtatg ccggggagat ctataattat     3000
```

-continued

```
gattttcctg agtatggggc aggacaacca ggagcatttg gagatataca atccagaaca      3060
gtctcaagct ctgatctgta tgccaatacc aacctagtgc tgcagagacc caaagcagga      3120
gcgatccacg tgccatacac tcaggcacct tcgggttttg agcaatggaa gaaagataaa      3180
gctccatcat tgaaatttac cgccccttc ggatgcgaaa tatatacaaa ccccattcgc       3240
gccgaaaact gtgctgtagg gtcaattcca ttagcctttg acattcccga cgccttgttc      3300
accagggtgt cagaaacacc gacactttca gcggccgaat gcactcttaa cgagtgcgtg      3360
tattcttccg actttggtgg gatcgccacg gtcaagtact cggccagcaa gtcaggcaag      3420
tgcgcagtcc atgtgccatc agggactgct accctaaaag aagcagcagt cgagctaacc      3480
gagcaagggt cggcgactat ccatttctcg accgcaaata tccacccgga gttcaggctc      3540
caaatatgca catcatatgt tacgtgcaaa ggtgattgtc acccccgaa agaccatatt       3600 gtgacacacc ctcagtatca cgcccaaaca tttacagccg cggtgtcaaa aaccgcgtgg      3660
acgtggttaa catccctgct gggaggatca gccgtaatta ttataattgg cttggtgctg      3720
gctactattg tggccatgta cgtgctgacc aaccagaaac ataat                      3765
```